(12) United States Patent
Huang et al.

(10) Patent No.: US 7,501,125 B2
(45) Date of Patent: Mar. 10, 2009

(54) VIVO CTL ELICITATION BY HEAT SHOCK PROTEIN FUSION PROTEINS MAPS TO A DISCRETE DOMAIN AND IS CD4+ T CELL-INDEPENDENT

(75) Inventors: Qian Huang, Arlington, MA (US); Joan F. L. Richmond, Arlington, MA (US); Bryan K. Cho, San Leandro, CA (US); Deborah Pallister, Cambridge, MA (US); Jianzhu Chen, Brookline, MA (US); Herman N. Eisen, Waban, MA (US); Richard A. Young, Weston, MA (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 59 days.

(21) Appl. No.: 10/885,523

(22) Filed: Jul. 1, 2004

(65) Prior Publication Data

US 2005/0048079 A1    Mar. 3, 2005

Related U.S. Application Data

(60) Division of application No. 09/761,534, filed on Jan. 16, 2001, now Pat. No. 6,875,435, which is a continuation of application No. PCT/US00/32831, filed on Dec. 1, 2000.

(60) Provisional application No. 60/176,143, filed on Jan. 14, 2000.

(51) Int. Cl.
*A61K 38/00* (2006.01)
*A61K 39/00* (2006.01)
*A61K 39/385* (2006.01)
*C07K 14/00* (2006.01)
*C07K 14/005* (2006.01)
*C07K 14/195* (2006.01)

(52) U.S. Cl. ............ 424/192.1; 424/184.1; 424/196.11; 424/197.11; 514/2; 530/350; 530/402; 530/403

(58) Field of Classification Search ............. 424/184.1, 424/185.1, 186.1, 188.1, 190.1, 192.1, 193.1, 424/197.11, 201.1, 204.1, 203.1, 234.1, 248.1, 424/278.1, 282.1; 435/67.1, 69.7, 440; 530/300, 530/350, 402, 403
See application file for complete search history.

(56) References Cited

U.S. PATENT DOCUMENTS

| 4,557,931 | A | 12/1985 | Irie et al. |
|---|---|---|---|
| 4,666,847 | A | 5/1987 | Alford et al. |
| 4,716,038 | A | 12/1987 | Stanford et al. |
| 4,724,144 | A | 2/1988 | Rook et al. |
| 4,734,362 | A | 3/1988 | Hung et al. |
| 4,784,941 | A | 11/1988 | Watanabe et al. |
| 4,797,359 | A | 1/1989 | Finkelstein |
| 4,918,164 | A | 4/1990 | Hellstrom et al. |
| 4,918,166 | A | 4/1990 | Kingsman et al. |
| 5,114,844 | A | 5/1992 | Cohen et al. |
| 5,204,259 | A | 4/1993 | Helting et al. |
| 5,256,767 | A | 10/1993 | Salk et al. |
| 5,504,005 | A | 4/1996 | Bloom et al. |
| 5,580,563 | A | 12/1996 | Tam |
| 5,925,362 | A | 7/1999 | Spitler et al. |
| 6,030,618 | A | 2/2000 | Srivastava |
| 6,335,183 | B1 | 1/2002 | Young |
| 6,338,952 | B1 | 1/2002 | Young |
| 6,403,099 | B1 | 6/2002 | Rappuoli et al. |
| 6,455,493 | B1 | 9/2002 | Wallen et al. |
| 6,482,614 | B1 | 11/2002 | Young |
| 6,495,347 | B1 | 12/2002 | Siegel et al. |
| 6,875,435 | B2 | 4/2005 | Huang et al. |
| 2001/0005713 | A1 | 6/2001 | Young |
| 2002/0146426 | A1 | 10/2002 | Huang et al. |
| 2003/0073094 | A1 | 4/2003 | Young et al. |
| 2004/0204363 | A1 | 10/2004 | Young |
| 2005/0048079 | A1 | 3/2005 | Huang et al. |
| 2005/0163792 | A1 | 7/2005 | Young et al. |

FOREIGN PATENT DOCUMENTS

| EP | 0 118 393 | A2 | 9/1984 |
|---|---|---|---|
| EP | 0 230 222 | A1 | 7/1987 |
| EP | 0 262 710 | | 9/1987 |
| EP | 0 322 990 | | 7/1989 |
| EP | 0 521 220 | A1 | 1/1993 |
| GB | 2 251 186 | | 7/1992 |

(Continued)

OTHER PUBLICATIONS

Ballard et al., "Anthrax Toxin-Mediated Delivery In Vivo and In Vitro of a Cytotoxic T-Lymphocyte Epitope from Ovalbumin," Infection and Immunity, vol. 66 No. 2, pp. 615-619 (Feb. 1998).*

(Continued)

*Primary Examiner*—Zachariah Lucas
(74) *Attorney, Agent, or Firm*—Hamilton, Brook, Smith and Reynolds, P.C.

(57) ABSTRACT

The present invention relates to a method of inducing a $CD8^+$ CTL response to a molecule in an individual deficient in $CD4^+$ T cells comprising administering to the individual an hsp or a portion of an ATP binding domain of an hsp joined to the molecule. In one embodiment, the present invention relates to a method of treating HIV in an individual deficient in $CD4^+$ T cells comprising administering to the individual an hsp or a portion of an ATP binding domain of an hsp joined to the molecule. Also encompassed by the present invention is a method of inducing a $CD4^+$ independent CTL response in an individual comprising administering to the individual a portion of an ATP binding domain of an hsp joined to the molecule. The present invention also relates to a method of inducing a $CD8^+$ CTL response in an individual comprising administering to the individual a portion of an ATP binding domain of an hsp joined to the molecule. In addition, the present invention relates to a composition characterized by a portion of an ATP biding domain of an hsp joined to a molecule.

24 Claims, 15 Drawing Sheets

FOREIGN PATENT DOCUMENTS

| | | |
|---|---|---|
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO 90/12030 | 9/1990 |
| WO | WO 90/15873 | 12/1990 |
| WO | WO 91/02542 | 3/1991 |
| WO | WO 91/15572 | 10/1991 |
| WO | WO 92/08484 | 5/1992 |
| WO | WO 92/08488 | 5/1992 |
| WO | WO 93/17712 | 9/1992 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 96/10421 | 4/1996 |
| WO | WO 97/06821 | 2/1997 |
| WO | WO 97/26910 | 7/1997 |
| WO | WO 98/23735 | 6/1998 |
| WO | WO 98/35705 | 8/1998 |
| WO | WO 99/07860 | 2/1999 |
| WO | WO 01/51081 | 7/2001 |

OTHER PUBLICATIONS

Belz et al., "A Previously Unrecognized H-2Db-Restricted Peptide Prominent in the Primary Influenza A Virus-Specific CD8+ T-Cell Response Is Much Less Apparent following Secondary Challenge," Journal of Virology, vol. 74 No. 8, pp. 3486-3493 (Apr. 2000).*

Bowie et al., "Deciphering the Message in Protein Sequences: Tolerance to Amino Acid Substitutions." Science, vol. 247 No. 4948, pp. 1306-1310 (Mar. 1990).*

Li et al., "Generation of Murine CTL by a Hepatitis B Virus-Specific Peptide and Evaluation of the Adjuvant Effect of Heat Shock Protein Glycoprotein 96 and Its Terminal Fragments," Journal of Immunology, vol. 174 No. 1, pp. 195-204 (2005).*

Agranovsky, A.A., et al., "Putative 65 kDa Protein of Beet Yellows Closterovirus is a Homologue of HSP70 Heat Shock Proteins," *J. Mol. Biol.*, 217:603-610 (1991).

Agterberg, M., et al., "Outer Membrane Protein PhoE as a Carrier for the Exposure of Foreign Antigenic Determinants at the Bacterial Cell Surface," *Antonie van Leeuwenhock* 59:249-262 (1991).

Agterberg, M., et al., "Outer Membrane PhoE Protein of *Escherichia coli* as a Carrier for Foreign Antigenic Determinants: Immunogenicity of Epitopes of Foot-and-Mouth Disease Virus," *Vaccine* 8:85-91 (Feb. 1990).

Agterberg, M., et al., "Protection of Guinea-pigs Against Foot-and-Mouth Disease Virus by Immunization with a PhoeE FMDV Hybrid Protein," *Vaccine* 8:438-440 (Oct. 1990).

Aldovini, et al., "Humoral and Cell-Mediated Immune Responses to Live Recombinant BCG-HIV Vaccines," Jun. 1991, *Nature* 351(6326):479-482.

Allen, P.M., et al., "T-Cell Recognition of Lysozyme: The Biochemical Basis of Presentation," *Immunological Reviews* 98:171-187 (1987).

Amadori, M., et al., "Chaperonin 10 o fMycobacterium tuberculosis Induces a Protective Immune Response to Foot-and-Mouth Disease Virus," *Arch Virol.* 144:905-919 (1999).

Amory Siosson, L.M., et al., "Induction of Protective Immunity in Mice Using A 62-kDa Recombinant Fragment of a *Schistosoma mansoni* Surface Antigen," *J. of Immunol.*, 149(11):3612-3620 (1992).

Anthony, L.S.D., et al., "Induction of HbcAg-Specific CTL Responses by a Heat Shock Protein Fused to the Core Antigen of the Hepatitis B Virus," Abstract S16 in the Final Program and Abstracts Book for The Fifth Annual Conference on Vaccine Research, held May 6-8, 2002.

Anthony, L.S.D., et al., "Priming of CD8+ CTL Effector Cells In Mice By Immunization With A Stress Protein-Influenza Virus Nucleoprotein Fusion Molecule," *Vaccine* 17:373-383 (1999).

Ardeshir, et al., "A 75 Kd Merozoite Surface Protein of Plasmodium Falciparum which is Related to the 70 kd Heat-Shock Proteins," *EMBO J.*, 6(2):493-499 (1987).

Arnosti, et al., "Characterization of Heat Shock," J. Bact. 168(3):1243-1249 (Dec. 1986).

Arrigo, A. and Welch, W.J., "Characterization and Purification of the Small 28,000-Dalton Mammalian Heat Shock Protein," *J. Biol. Chem.*, 262(32):15359-15369 (1987).

Babbitt, et al., "Binding of Immunogenic Peptides to Ia Histocompatibility Molecules," *Nature* 317:359-361 (1985).

Bardwell, et al., "The Nucleotide Sequence of the *Escherichia coli* K12 dnaJ+ Gene," Feb. 1986, *Journal of Biological Chemistry*, 261(4):1782-1785.

Barouch, et al., "Eventual AIDS Vaccine Failure in a Rhesus Monkey By Viral Escape From Cytotoxic Lymphocytes," *Nature* 415:335-339 (2002).

Barrios, C., et al., "Mycobacterial heat-shock proteins as carrier Molecules. II: The use of the 70-kDa mycobacterial heat-shock protein as carrier for conjugated vaccines can circumvent the need for adjuvants and Bacillus Calmette Guerin priming," *Eur. J. Immunol.*, 22:1365-1372 (1992).

Barrios, C. et al., "Heat shock proteins as carrier molecules: in vivo helper effect mediated by *Escherichia coli* GroE1 and DnaK proteins requires cross-linking with antigen," *Clin. Exp. Immunol.*, 98:229-233 (1994).

Bayliss, C.D., et al., "A Recombinant Fowlpox Virus That Expresses the VP2 Antigen of Infectious Bursal Disease Virus Induces Protection Against Mortality Caused by the Virus," *Arch Virol.* 120:193-205 (1991).

Bennett, S.R.M., et al., "Help for Cytotoxic-T-cell Repsonses is Mediated by CD40 Signalling," *Nature* 393:478-480 (Jun. 4, 1998).

Bertelli, M.S., et al., "BCG-Induced Resistance in *Trypanosoma cruzi* Experimental Infections," Tropenmed Parasitol, 32:93-96 (1981).

Billman-Jacobe, H., et al., "Mapping of the T and B Cell Epitopes of the *Mycobacterium bovis* Protein, MPB70," *Immunol. Cell Biol.* 68:359-365 (1990).

Blachere, N.E., et al., "Heat Shock Protein-Peptide Complexes, Reconstituted In Vitro, Elicit Peptide-specific Cytotoxic T Lymphocyte Response and Tumor Immunity," *J. Exp. Med.* 186(8):1315-1322 (Oct. 20, 1997).

Blachere, N.E., et al., "Heat Shock Protein Vaccines Against Cancer," *J. Immunotherapy* 14(4):352-356 (1993).

Blander, S.J. and Horwitz, M.A., "Major Cytoplasmic Membrane Protein of *Legionella pneumophila*, a Genus Common Antigen and Member of the hsp 60 Family of Heat Shock Proteins, Induces Protective Immunity in a Guinea Pig Model of Legionnaires' Disease," *J. Clin. Invest.*, 91:717-723 (1993).

Breloer, M., et al., "In Vivo and In Vitro Activation of T Cells After Administration of Ag-Negative Heat Shock Proteins," *J. of Immunl.* 162:3141-3147 (1999).

Brett, et al., "Differential Pattern of T Cell Recognition of the 65-kDA Mycobacterial Antigen Following Immunization with the Whole Protein or Peptides, " *Euro. J. Immunol.* 19:1303-1310 (1989).

Brett, S.J., et al., "Influences of Antigen Processing on the Expression of the T Cell Repertoire," *J. Exp. Med.* 168:357-373 (Jul. 1988).

Brewer, S.J., et al., "Engineering Proteins to Enable Their Isolation in a Biologically Active Form," Purification and Analysis of Recombinant Proteins, Seltharam and Sharma (Eds.), Marcel Dekker, Inc., NY (1991).

Britton, et al., "The Characterization and Immunoreactivity of a 70 KD Protein Common to *Mycobacterium leprae* and *Mycobacterium bovis* (BCG)," 1986, *Leprosy Review*, 57 Supp. 2:67-75.

Burrows, P.D., et al., "B-Cell Development in Man," *Curr. Opinion Biol.* 5:201-206 (1993).

Butini, et al., "Comparative Analysis of . . .," *J. Cell. Biochem., Suppl.* 18B, Abstract J306 (1994).

Cane, P.A., et al., "Reduction of Yellow Fever Virus Mouse Neurovirulence by Immunization with a Bacterially Synthesized Non-structural Protein (NS1) Fragment," *J. Gen. Virol.* 269:1241-1246 (1988).

Cassell, W.A. et al., "Viral Oncolysate in the Management of Malignant Melanoma, I. Preparation of the Oncolysate and Measurement of Immunologic Responses" *Cancer*, 40:672-679 (Aug. 1977).

Cassell, W.A., et al., "A Phase II Study on the Postsurgical Management of Stage Malignant Melanoma With a Newcastle Disease Virus Oncolysate," *Cancer*, 52:856-860 (Sep. 1983).

Catelli, M.G., et al., "The common 90-kd protein component of non-transformed '8S' steroid receptors is a heat-shock protein," *EMBO J.*, 4(12):3131-3135 (1985).

Chandrasekhar, G.N., et al., "Purification and Properties of the groES Morphogenetic Protein of *Escherichia coli*," *J. Biol. Chem.* 261(26):12414-12419 (1986).

Chen, W., et al., "Human 60-kDa Heat-Shock Protein: A Danger Signal to the Innate Immune System," *J. of Immun.* 162:3212-3219 (1999).

Chong, P., et al., "Identification of a Potent Synthetic HIV1 Immunogen Comprising gag-P24 Tandem T-and B-Cell Epitopes," *FEBS* 264(2):231-234 (May 1990).

Chu, N.R., et al., "Immunotherapy of a Human Papillomavirus (HPV) Type 16 E7-Expressing Tumour by Administration of Fusion Protein Comprising *Mycobacterium bovis* Bacille Calmette-Guérin (BCG) hsp65 and HPV16 E7," *Clin. Exp. Immunol.* 121:216-225 (2000).

Ciborowski, P., et al., "Immunological response to a *Staphylococcus aureus* fibronectin-binding protein," *J. Med. Microbiol.*, 37:376-381 (1992).

Ciupitu, A.T., et al., "Immunization with a Lymphocytic Choriomeningitis Virus Peptide Mixed with Heat Shock Protein 70 Results in Protective Antiviral Immunity and Specific Cytotoxic T Lymphocytes," *J. Exp. Med.* 187(5):685-691 (Mar. 2, 1998).

Clarke, B.E., et al., "Presentation and immunogenicity of viral epitopes on the surface of hybrid hepatitis B virus core particles produced in bacteria," *J. of General Virology*, 71:1109-1117 (1990).

Clarke, B.E., et al., "Improved Immunogenicity of a Peptide Epitope After Fusion to Hepatitis B Core Protein," *Nature* 330:381-384 (Nov. 1987).

Clough, E.R., et al., "Production of Anti-Sporozoite Antibodies in Absence of Response to Carrier By Coupling and MDP Derivative to a Malaria Peptide-Tetanus Toxoid Conjugate," Biochemical and Biophysical Research Communications, 131(1):70-75 (1985).

Cohen, J., "Jitters Jeopardize AIDS Vaccine Trials," *Science* 262:980-981 (1993).

Cox, et al., "Orientation of Epitopes Influences the Immunogenicity of Synthetic Peptide Dimers," *Euro. J. Immunol.* 18:2015-2019 (1988).

Crane, M.S., et al., "Cross-Protection Against Four Species of Chicken Coccidia with a Single Recombinant Antigen," Infection and Immunity 59(4):1271-1277 (Apr. 1991).

Davis, et al., "Immune Response to Human Influenza Virus Hemagglutinin Expressed in *Escherichia coli*," Mar. 1983, *Gene*, 21(3):273-284.

Davis, B.D., et al., Microbiology, second edition, Harper & Row, Publishers, pp. 600 & 622.

De Valesco, E.A., et al., "Synthetic Peptides Representing T-Cell Epitopes Act as Carriers in Pneumococcal Polysaccharide Conjugate Vaccines," *Infect. & Immun.*, 63(3):961-968 (1955).

Decision Revoking European Patent EP-B-0419569.

Del Giudice, et al., "Heat Shock Proteins as "Super"-Carriers for Sporozite Peptide Vaccines?," *Research in Immunology*, 142(8):703-707 (1991).

Del Giudice, G.D., et al., "Priming to Heat Shock Proteins in Infants Vaccinated against Pertussis," *J. Immunol.*, 150(5):2025-2032 (1993).

Delmas, A., et al., "Studies of the Influence of Different Cross-Linking Reagents on the Immune Response against a B-Epitope," *Bioconjugate Chemistry* 3(1):80-84 (1992).

DeNagel, D.C. and Pierce, S.K., "Heat Shock Proteins in Immune Responses," *Crit. Rev. Immunol.*, 13(1):71-81 (1993).

Derkay, C.S.I., et al., "Hsp E7 Treatment of Pediatric Recurrent Respiratory Papillomatosis (RRP): Final Results of an Open-Label Trial," Abstract 633 on p. 443 of the Final Program for the 21$^{st}$ International Papillomavirus Conference & Clinical Workshop (2004).

Dintzis, R.Z., "Rational Design of Conjugate Vaccines," Pediatric Research 32(4):376-385 (1992).

Doherty, et al., Evasion of host immune responses by tumours and viruses, "Vaccines against virally induced cancers", Wiley, Chicester (Ciba Foundation Symposium 187), pp. 245-260. See p. 245, Abstract.

Drew, M.D. et al., "Vaccination By Cholera Toxin Conjugated to a Herpes Simplex Virus Type 2 Glycoprotein D Peptide," *J. General Virol.* 73:2357-2366 (1992).

DuBois, G.C., et al., "Isolation of a Tumor-Associated Transplantation Antigen (TATA) From an SV40-Induced Sarcoma. Resemblance to the TATA of Chemically Induced Neoplasms," *Int. J. Cancer*, 34:561-566 (1984).

Einstein, M.H., et al., Heat Shock Protein (HSP)-Based Immunotherapy (HspE7) for Treatment of CIN III (NCI 5850, NYGOG), Abstract 8 in the Abstract Book and Final Program for The Annual Meeting on Women's Cancer™; The Society of Gynecologic Oncologists' 36$^{th}$ Annual Meeting, Mar. 19-23, 2005.

Elias, D., et al, "Induction and therapy of autoimmune diabetes in the non-obese diabetic (NOD/Lt) mouse by a 65-kDa heat shock protein," *Proc. Natl. Acad. Sci. USA*, 87:1576-1580 (1990).

Emmrich, F., et al., "A Recombinant 64 Kilodalton Protein of *Mycobacterium bovis* Bacillus Calmette-Guerin Specifically Stimulates Human T4 Clones Reactive to Mycobacterial Antigens," *J. Exp. Med.*163:1024-1029 (Apr. 1986).

Engel, et al., "Generation of Antibodies Against Human hsp27 and Murine hsp25 by Immunization with a Chimeric Small Heat Shock Protein," *Biomed. Biochim. Acta 50*:1065-1071 (1991).

Etlinger, H.M., et al., "Antibody Responses to a Synthetic Peptide-Based Malaria Vaccine Candidate: Influence of Sequence Variants of the Peptide," *Eur. J. Immunol.* 21:1505-1511 (1991).

European Patent No. 0700445 B1; Opposition By Antigenics, Inc.: Statement of Grounds of Opposition.

Falk, R.E., et al., "Cell Mediated Immunity to Human Tumors," *Arch. Surg.*, 107:261-265 (Aug. 1973).

Farrelly, et al., "Complete Sequence of the Heat Shock-Inducible HSP90 Gene of *Saccharomyces cerevisiae*," May 1984, *Journal of Biological Chemistry*, 259(9):5745-5751.

Ferrero, R.L. et al., "The GroES homolog of *Helicobacter pylori* confers protective immunity against mucosal infection in mice," Proc. Natl. Acad. Sci. USA, 92:6499-6503 (1995).

Finnegan, A., et al., "The T Cell Repertoire For Recognition of a Phylogenetically Distant Protein Antigen—Peptide Specificity and MHC Restriction of Staphylococcal Nuclease-specific T Cell Clones," *J. Exp. Med.* 164:897-910 (Sep. 1986).

Flaherty, K., et al., "Three-dimensional Structure of the ATPase Fragment of a 70K Heat-Shock Cognate Protein," *Nature* 346:623-628 (Aug. 16, 1990).

Francis, et al., "Peptide Vaccines Based on Enhanced Immunogenicity of Peptide Epitopes Presented with T-Cell Determinants or Hepatitis B Core Protein," *Meth. Enzymol.* 178:659-676 (1989).

Francis, M.J., et al., "Non-Responsiveness to a Foot-and-Mouth Disease Virus Peptide Overcome by Addition of Foreign Helper T-Cell Determinants," *Nature* 330:168-170 (Nov. 1987).

Freimuth, P., et al., "Insertion of Myoglobin T-Cell Epitopes Into the *Escherichia coli* Alkaline Phosphatase," *Res. Microbiol.* 141:995-1001 (1990).

Friedland, J.S. et al., "Mycobacterial 65-kD heat shock protein induces release of proinflammatory cytokines from human monocytic cells," *Clin. Exp. Immunol.*, 91:58-62 (1993).

Fuqua, S.A.W. et al., "Induction of the Estrogen-regulated "24K" Protein by Heat Shock," *Cancer Research 49*:4126-4129 (Aug. 1, 1989).

Fyfe, et al., "Murine Immune Response to HIV-1 p24 Core Protein Following Subcutaneous, Intraperitoneal and Intravenous Immunization," *Immunology* 74:467-472 (1991).

Gammon, G., et al., "The Choice of T-Cell Epitopes Utilized on a Protein Antigen Depends on Multiple Factors Distant from, as well as at the Determinant Site," Immunological Reviews 98:53-73 (1987).

Gariepy, J., et al., "Vectorial Delivery of Macromolecules Into Cells Using Peptide-Based Vehicles," *Trends Biotechnol.* 19(1):21-28 (2001).

Garsia, et al., "Homology of the 70-Kilodalton Antigens from *Mycobacterium leprae* and *Mycobacterium bovis* with the Mycobacterium tuberculosis 71-Kilodalton Antigen and with the Conserved Heat Shock Protein 70 of Eucaryotes," Jan. 1989, *Infection and Immunity*, 57(1):204-212.

Gelber, R.H., et al., "Vaccination With Pure *Mycobacterium leprae* Proteins Inhibits *M. leprae* Multiplication in Mouse Footpads," *Infection and Immunity* 62(10):4250-4255 (Oct. 1994).

Geluk, A., et al., "Functional Analysis of DR17(DR3)-Restricted Mycobacterial T Cell Epitopes Reveals DR17-Binding Motif and Enables The Design of Allele-Specific Competitor Peptides," *J. Immunology* 149(9):2864-2871 (Nov. 1, 1992).

Goldstone, S.E., et al., "Activity of HspE7, a Novel Immunotherapy, in Patients with Anogenital Warts," *Dis. Colon Rectum* 45:502-507 (2002).

Gomes, et al., "Heat Shock Protein Synthesis During Development . . . ," *J. Bact.* 168(3):923-930 (Nov. 1986).

Gomez, F.J., et al., "Vaccination with Recombinant Heat Shock Protein 60 from *Histoplasma capsulatum* Protects Mice against Pulmonary Histoplasmosis," *Infect. & Immun.*, 63:2587-2595 (1995).

Gomez, et al., "An 80-Kilodlaton Antigen from *Histoplasma capsulatum* That Has Homology to Heat Shock Protein 70 Induces Cell-Mediated Immune Responses and Protection in Mice," Jul. 1992, *Infection and Immunity*, 60(7):2565-2571.

Good, M.F., et al., "Construction of Synthetic Immunogen: Use of New T-Helper Epitope on Malaria Circumsporozoite Protein," *Science* 235:1059-1062 (Feb. 1987).

Grange, J.M., et al., "Tuberculosis and Cancer: Parallels in Host Responses and Therapeutic Approaches?," *The Lancet* 345:1350-1352 (1995).

Gupta, R.K., et al., "Adjuvants—a Balance Between Toxicity and Adjuvanticity," *Vaccine* 11:293-306 (2002).

Haghbin, M., et al., "Immunotherapy with Oral BCG and Serial Immune Evaluation in Childhood Lymphoblastic Leukemia Following Three Years of Chemotherapy," *Cancer*, 46:2577-2586 (Dec. 1980).

Handman, E., et al., "Leishmania major: Production of Recombinant gp63, Its Antigenicity and Immunogenicity in Mice," Experimental Parasitology 70:427-435 (1990).

Hawiger, J., "Noninvasive Intracellular Delivery of Functional Peptides and Proteins," *J. Curr. Opin. Chem. Biol.* 3:89-94 (1999).

Haynes, B.F., "Scientific and Social Issues of Human Immunodeficiency Virus Vaccine Development," *Science* 260:1279-1286 (1993).

Hearn, M.T.W., et al., "Applications of Novel Affinity Cassette Methods: Use of Peptide Fusino Handles for the Purification of Recombinant Proteins," *J. Mol. Recognition* 14:323-369 (2001).

Hedstrom, R., et al., "A Major Immunogen in *Schistosoma mansoni* Infections is Homologous to the Heat-Shock Protein Hsp70," *J. Exp. Med.* 165:1430-1435 (1987).

Hinuma, S., et al., "A Novel Strategy For Converting Recombinant Viral Protein Into High Immunogenic Antigen," *FEBS* 288(1,2):138-142 (Aug. 1991).

Hird, et al., Immunotherapy with Monoclonal Antibodies, Genes and Cancer, Edited by Carney, et al., pp. 183-189, see p. 185, first paragraph.

Hogervorst, E.M., et al., "Efficient Recognition by Rat T Cell Clones of an Epitope of Mycobacterial hsp 65 Inserted in *Escherichia coli* Outer Membrane Protein PhoE," *Eur. J. Immunol.* 20:2763-2768 (1990).

Horwitz, M.A., et al., "Protective Immunity Against Tuberculosis Induced by Vaccination With Major Extracellular Proteins of Mycobacterium tuberculosis," *Microbiology* 92:1530-1534 (Feb. 1995).

Horwitz, M.S., et al., "Diabetes induced by Coxsackie virus: Initiation by bystander damage and not molecular mimicry," *Nature Med.* 4:781-785 (1998).

Huang, Q., et al., "In Vivo Cytotoxic T Lymphocyte Elicitation by Mycobacterial Heat Shock Protein 70 Fusion Proteins Maps to a Discrete Domain and Is CD4+ T Cell Independent," *J. Exp. Med.* 191(2):403-408 (Jan. 17, 2000).

Hudson, C.N., et al., "Active Specific Immunotherapy for Ovarian Cancer," *The Lancet*, 2:877-879 (Oct. 23, 1976).

Hughes, L.E., et al., "A Study in Clinical Cancer Immunotherapy," *Cancer*, 26:269-278 (Aug. 1970).

Humphrey, L.J., et al., "Adjuvant Immunotherapy for Melanoma," *J. of Sur. Oncol.*, 25:303-305 (1984).

Hunt, C. and Calderwood, S., "Characterization and Sequence of a Mouse hsp70 Gene and Its Expression in Mouse Cell Lines," *Gene* 87:199-204 (1990).

Husson, R.N. and Young, R.A., "Genes for the major protein antigens of Mycobacterium tuberculosis: The etiologic agents of tuberculosis and leprosy share an immunodominant antigen," *Proc. Natl. Acad. Sci. USA*, 84:1679-1683 (1987).

Jacobs, et al., "Introduction of Foreign DNA into Mycobacteria Using a Shuttle Phasmid," Jun. 1987, *Nature*, 327(6122):532-535.

Janeway, et al., *Immunobiology*, 5th Ed., 2001, Garland Publishing, sections 1-5 to 1-13 (10 pages).

Janvier, B., et al., "Immune Response to a Major Epitope of p24 During Infection with Human Immunodeficiency Virus Type 1 and Implications for Diagnosis and Prognosis," *J. Clinical Microbiol.* 29(3):488-492 (Mar. 1991).

Jarecki-Black, J.C., et al., "The Effect of BCG-Vaccine Upon Experimental Visceral Leishmaniasis in Hampsters," *Ann. Clin. Lab. Sci.*, 14:464-466 (1984).

Jarrett, W.F.H., et al., "Studies on Vaccination against Papillomaviruses: Prophylactic and Therapeutic Vaccination with Recombinant Structural Proteins," *Virology*, 184:33-42 (1991).

Jin, X.W., et al., "Bovine Serological Response to a Recombinant BPV-1 Major Caspid Protein Vaccine," *Intervirology* 31:345-354 (1990).

Jindal, S., "Heat Shock Proteins: Applications in health and disease," Trends in Biotech., 14(1):17-20, 1996.

Johnston, J.M., et al., "Antigenic and Immunogenic Properties of a Hepatitis A Virus Capsid Protein Expressed in *Escherichia coli*," *J. Infect. Diseases* 157(6):1203-1211 (Jun. 1988).

Jondal, M., et al., "MHC Class I-Restricted CTL Responses to Exogenous Antigens," Immunity 5:295-203 (Oct. 1996).

Kaufmann, S.H.E., et al., "Enumeration of T cells reactive with Mycobacterium tuberculosis organisms and specific for the recombinant mycobacterial 64-kDa protein," *Eur. J. Immunol.* 17:351-357 (1987).

Kazura, J.W., et al., "Protective Efficacy of a Cloned Brugia malayi Antigen in a Mouse Model of Microfilaremia," *J. Immunol.* 145(7):2260-2264 (Oct. 1990).

Kimmig, P. and Wenk, P., "Suppression of Parasitaemia from *Litomosoides carinii* by Immunisation with BCG and Microfilariae," *Z Parasitenkd*, 67:317-327 (1982).

Kit, M., et al., "Bovine Herpesvirus-1 (Infectious Bovine Rhinotracheitis Virus)-Based Viral Vector Which Expresses Foot-and-Mouth Disease Epitopes," *Vaccine* 9: 564-572 (Aug. 1991).

Klinkert, M., et al., "Surface Proteins of *Mycoplasma hyopneumoniae* Identified from an *Escherichia coli* Expression Plasmid Library," *Infection and Immunity* 49(2): 329-335 (1985).

Knapp, B., et al., "A Histidin Alanine Rich Recombinant Antigen Protects Aotus Monkeys from *P. Falciparium* Infection," *Behring Inst. Mitt.82*:349-359 (1988).

Kol, A., et al., "Chlamydial and Human Heat Shock Protein 60s Activate Human Vascular Endothelium, Smooth Muscle Cells, and Macrophages," *J. Clin. Invest.* 103:571-577 (1999).

Könen-Waisman, S., et al., "Self Heat-Shock Protein (hsp60) Peptide Serves in a Conjugate Vaccine against a Lethal Pneumococcal Infection," *J. Infect. Diseases* 179:403-413 (1999).

Könen-Waisman, S., et al., "Self and Foreign 60 Kilodation Heat Shock Protein T Cell Epitope Peptides Serve As Immunogenic Carriers for a T Cell-Independent Sugar Antigen," *J. Immunol.*, 154:5977-5985 (1995).

Krska, J., et al., "Monoclonal Antibody Recognition and Function of a DnaK (HSP70) Epitope Found in Gram-Negative Bacteria," *J. Bacteriology* 175(20):6433-6440 (1993).

Krzych, U., et al., "Repertoires of T Cells Directed Against A Large Protein Antigen, -Galactosidase," *J. Immunol.* 128(4):1529-1534 (Apr. 1982).

La Thangue, N.B. and Latchman, D.S., "A Cellular Protein Related to Heat-Shock Protein 90 Accumulates during Herpes Simplex Virus Infection and Is Overexpressed in Transformed Cells," *Experimental Cell Research*, 178:169-179 (1988).

Lamb, F.I., et al., "Heterologous Expression of the 65-Kilodalton Antigen of *Mycobacterium leprae* and Murine T-Cell Responses to the Gene Product," *Infection and Immunity* 56(5):1237-1241 (May 1988).

Lamb, J.R., et al., "Stress Proteins May Provide a Link Between the Immune Response to Infection and Autoimmunity," *Int'l Immun.*, 1(2): 191-196 (1989).

Lamb, J.R., et al., "Mapping of T Cell Epitopes Using Recombinant Antigens and Synthetic Peptides," *The EMBO J.* 6(5):1245-1249 (1987).

Lawrence, R.M., et al., "Expression of the Cloned Gene for Enterotoxin Stb of *Escherichia coli*," *Infection and Immunity*, 58(4):970-977 (1990).

Layton, et al., "Induction of HIV-Specific Cytotoxic . . . ," *J. Immun.* 151(2):1097-1107 (Jul. 1993).

Leclerc, C., et al., "A Synthetic Vaccine Constructed by Copolymerization of B and T Cell Determinants," *Eur. J. Immunol.* 17:269-273 (1987).

Lee, A.C.J., et al., "A Method for Preparing -hCG Cooh Peptide-Carrier Conjugates of Predictable Composition," *Molecular Immunology*, 17:749-756 (1980).

Lehner, T., et al., "Heat Shock Proteins Generate ?-Chemokines Which Function as Innate Adjuvants Enhancing Adaptive Immunity," *Eur. J. Immunol.* 30:594-603 (2000).

Lehner, T., et al., "Identification of T- and B-CellEpitopes in Synthetic Peptides Derived From a Streptococcus Mutans Proteins and Characterization of Their Antigenicity and Immunogenicity," *Archs oral Biol. 35*, Suppl.:39S-45S (1990).

Li, Z. and Srivastava, P.K., "Tumor Rejection Antigen gp96/grp94 is an ATPase: Implications for Protein Folding and Antigen Presentation," *The EMBO Journal*, 12(8):3143-3151 (1993).

Lindgren, M., et al., "Cell-Penetrating Peptides," *TiPS 21*(3):99-103 (Mar. 2000).

Lindquist, S. and Craig, E.A., "The Heat-Shock Proteins," *Annu. Rev. Genet.*, 22:631-677 (1988).

Lindquist, S., "The Heat-Shock Response," Jul. 1986, *Annual Review of Biochemistry*, 55:1151-1191.

Linsley, P.S., et al., "T-Cell Antigen CD28 Mediates Adhesion With B Cells By Interacting With Activation Antigen B7/BB-1," *Proc. Natl. Acad. Sci. USA 87*:5031-5035 (Jul. 1990).

Liu, H., et al., Abstract Th25.22 in *Clin. Invest. Med.* 27:73D (2004).

Löwenadler, B., et al., "T and B Cell Responses To Chimeric Proteins Containing Heterologous T Helper Epitopes Inserted At Different Positions," *Molecular Immunology 29*(10):1185-1190 (1992).

Löwenadler, B., et al., "Enhanced Immunogenicity of Recombinant Peptide Fusions Containing Multiple Copies of a Heterologous T Helper Epitope," *Eur. Immunol. 20*:1541-1545 (1990).

Löwenadler, B., et al., "A recombinant *Escherichia coli* heat-stable enterotoxin (Sta) fusion protein eliciting anti-STa neutralizing antibodies," *FEMS Microbiology Letters*, 82:271-277 (1991).

Lussow, A.R., et al., "Mycobacterial heat-shock proteins as carrier molecules", *Eur. J. Immunol.*, 21:2297-2302 (1991).

Matthews, R.C., et al., "Autoantibody to Heat-Shock Protein 90 Can Mediate Protection Against Systemic Candidosis," *Immunology* 74:20-24 (1991).

McCulloch, P.B., et al., "Recurrent Malignant Melanoma: Effect of Adjuvant Immunotherapy on Survival," *Can. Med. Assoc. J.*, 117:33-36 (1977).

McKenzie, K.R., et al., "Sequence and Immunogenicity of the 70-kDa Heat Shock Protein of *Mycobacterium leprae*," *J. Immunol.* 147(1):312-319 (1991).

Mehra, V., et al., "Efficient Mapping of Protein Antigenic Determinants," *Proc. Natl. Acad. Sci. USA 83*:7013-7017 (1986).

Merrick, R.M., et al., "The Use of -Galactosidase Fusion Proteins Encoding the Early Region 1 Transforming Proteins of Adenovirus Type 12 to Examine the Humoral Response in Tumor-Bearing Animals," *J. Gen. Virol.* 72:955-960 (1991).

Miller, G.A., et al., "Characterization and Vaccine Potential of a Novel Recombinant Coccidial Antigen," *Infection and Immunity*, 57(7):2014-2020 (1989).

Miller, A., et al., "Immunotherapy in autoimmune diseases," *Curr. Opinion in Immun.*, 3:936-940 (1991).

Moore, S.K., et al., "Murine 86- and 84-kDa Heat Shock Proteins, cDNA Sequences, Chromosome Assignments, and Evolutionary Origins," *J. Biol. Chem.* 264(10):5343-5351 (1989).

More, et al., "Activation of Cytotoxic T Cells In Vitro . . . ," *Immunology Letters* 69:275-282 (1999).

Morgan, D.O., et al., "Protection of Cattle and Swine Against Foot-and-Mouth Disease, Using Biosynthetic Peptide Vaccines," *Am. J. Vet. Res.* 51(1):40-45 (1990).

Morimoto, R.I., "Cells in Stress: Transcriptional Activation of Heat Shock Genes," *Science 259*:1409-1410 (1993).

Morris, M.C., et al., "Translocating Peptides and Proteins and Their Use for Gene Delivery," *Curr. Opin. Biotechnol.* 11(5):461-466 (2000).

Moser, D., et al., "The Humoral Response to Heat Shock Protein 70 in Human and Murine *Schistosomiases mansoni*," *Parasite Immunol.* 12:341-352 (1990).

Multhoff, G., et al., "The Role of Heat Shock Proteins in the Stimulation of an Immune Response," *Biol. Chem. 379*:295-300 (1998).

Murphy, J.R. and Lefford, M.J., "Host Defenses in Murine Malaria: Induction of a Protracted State of Immunity with a Formalin-Killed *Plasmodium berghei* Blood Parasite Vaccine," *Infec. Immun.*, 22:798-803 (1978).

Murray, D.R., et al., "Viral Oncolysate in the Management of Malignant Melanoma, II. Clinical Studies" *Cancer*, 40:680-686 (1977).

Myers, "Role of B Cell Antigen Processing and Presentation in the Humoral Immune Response," *FASEB J. 5*:2547-2553 (1991).

Nadler, S.G., et al., "Interaction of the Immunosupressant Deoxyspergualin with a Member of the Hsp70 Family of Heat Shock Proteins," *Science*, 258:484-486 (1992).

Nair, S., et al., "Calreticulin Displays In Vivo Peptide-Binding Activity and Can Elicit CTL Responses Against Bound Peptides," *J. Immun. 162*:6426-6432 (1999).

NCBI Accession CAD93221, Probable Chaperone Protein DNAK . . . , Apr. 2005.

NCBI Accession NP_854111, 60 KDA Chaperonin . . . , Apr. 2005.

Noll, A. and Autenrieti, I.B., "Immunity against *Yersinia enterocolitica* by Vaccination with Yersinia HSP60 Immunostimulating Complexes or Yersinia HSP60 plus Interleukin-12," *Infect. & Immun.*, 64:2955-2961 (1996).

Nov. 2000 Printout of a Web Page of Stressgen Biotechnologies (http//stressgen.com).

Oberg, L.A., et al., "Bacterially Expressed Nucleoprotein of Infectious Hematopoietic Necrosis Virus Augments Protective Immunity Induced by the Glycoprotein Vaccine in Fish," *J. Virol.* 65:4486-4489 (Aug. 1991).

Oettgen, H.F. and Old, L.J., "Chapter 6: The History of Cancer Immunotherapy." In Biologic Therapy of Cancer, De Vita, V.T., Hellman, S. and Rosenberg, S.A., eds., (London: J.B. Lippincott) pp. 98-103 (1991).

Oftung, et al., "Mapping of Multiple HLA Class II-Restricted T-Cell Epitopes of the Mycobacterial 70-Kilodalton Heat Shock Protein," 1994, *Infection and Immunity*, 62(12):5411-5418.

Oftung, F., et al., "Human T Cell Clones Recognize Two Abundant Mycobacterium tuberculosis Protein Antigens Expressed in *Escherichia coli*," *J. Immunol.* 138(3):927-931 (1987).

Owens, T., et al., "The Cell Biology of T-dependent B Cell Activation," Leucocytes: Functions and Pathogenesis, Biochem. Cell Biol. 67:481-489 (1989).

Palladino, M.A., et al., "Expression of a Shared Tumor-Specific Antigen by Two Chemically Induced BALB/c Sarcomas," *Cancer Research*, 47:5074-5079 (1987).

Palliser, D., et al., "Multiple Intracellular Routes in the Cross-Presentation of a Soluble Protein by Murine Dendritic Cells," *J. Immunol.* 174:1879-1887 (2005).

Parker, "T-Cell Dependent B Cell Activiation," *Annu. Rev. Immunol.* 11:331-360 (1993).

Partidos, C.D., et al., "Immune Responses in Mice Following Immunization With Chimeric Synthetic Peptides Representing B and T Cell Epitopes of Measles Virus Proteins," *J. Gen. Virol.* 72:1293-1299 (1991).

Pedersen, J., et al., "Removal of N-Terminal Polyhistidine Tags from Recombinant Proteins Using Engineered Aminopeptidases," *Protein Expression and Purification* 15:389-400 (1991).

Peeters, J.M., et al., "Comparison of four bifunctional reagents for coupling peptides to proteins and the effect of the three moieties on the immunogenicity of the conjugates," *J. of Immunol. Methods*, 120:133-143 (1989).

Phalipon, A., et al., "Expression of a poliovirus type 1 neutralization epitope on a diphtheria toxin fusion protein," *Vaccine*, 7

Thanavala, Y.M., et al., "Affinity, cross-reactivity and biological effectiveness of rabbit antibodies against a synthetic 37 amino acid C-terminal peptide of human chorionic gonadotrophin," *Clin. Exp. Immunol.*, 39:112-118 (1980).

Thole, J.E.R., et al., "Use of Recombinant Antigens Expressed in *Escherichia coli* K-12 To Map B-Cell and T-Cell Epitopes on the Immunodominant 65-Kilodalton Protein of *Mycobacterium bovis* BCG," *Infection and Immunity* 56(6):1633-1640 (Jun. 1988).

Thole, J.E.R., et al., "Antigenic relatedness of a strongly immunogenic 65 kDa mycobacterial protein antigen with a similarly sized ubiquitous bacterial common antigen," *Microbial Pathogenesis*, 4:71-83 (1988).

Thole, J.E.R., et al., "Characterization, Sequence Determination, and Immunogenicity of a 64-Kilodalton Protein of *Mycobacterium bovis* BCG Expressed in *Escherichia coli* K-12," *Infection & Immunol.*, 55(6):1466-1475 (1987).

Tommassen, J., et al., "Molecular Analysis of the Promoter Region of the *Escherichia coli* K-12 phoE Gene—Identification of an Element, Upstream from the Promoter, Required for Efficient Expression of PhoE Protein," *Mol. Biol. 198*:633-641 (1987).

Townsend, et al., "Antigen Recognition by Class I-Restricted T Lymphocytes," *Ann. Rev. Immunol. 7*:601-624 (1989).

Traversari, C., et al., "A Nonapeptide Encoded by Human Gene MAGE-1 Is Recognized on HLA-A1 by Cytolytic T Lymphocited Directed Against Tumor Antigen MZ2-E," *J. Exp. Med. 176*:1453-1457 (1992).

Udono, H., et al., "Comparison of Tumor-Specific Immunogenicities of Stress-Induced Proteins gp96, hsp90, and hsp70," *J. Immunol. 152*: 5398-5403 (1994).

Udono, H., et al., "Cellular Requirements For Tumor-Specific Immunity Elicited By Heat Shock Proteins: Tumor Rejection Antigen gp96 Primes CD8+ T Cells in vivo," *Proc. Natl. Acad. Sci. USA 91*:3077-3081 (1994).

Udono, H. and Srivastava, P.K., "Heat Shock Protein 70-associated Peptides Elicit Specific Cancer Immunity," *J. Exp. Med.*, 178:1391-1396 (1993).

Ullrich, S.J., et al., "A Mouse Tumor-Specific Transplantation Antigen is a Heat Shock-Related Protein," *Proc. Natl. Acad. Sci.*, USA, 83:3121-3125 (1986).

Ullrich, S.J., et al., "Transcriptional and Translational Analysis of the Murine 84- and 86-kDa Heat Shock Proteins," *J. Biol. Chem. 264*(12):6810-6816 (1989).

van Eden, W., et al., "Cloning of the mycobacterial epitope recognized by T lynmphocytes in adjuvant arthritis," *Nature*, 331(14):171-173 (1988).

Verdegaal, E.M.E. et al., "Heat Shock Protein 65 Induces CD62e, CD106, and CD54 on Cultured Human Endothelial Cells and Increases Their Adhesiveness for Monocytes and Granulocytes," *J. Immunol.*, 157:369-376 (1996).

Vodkin, M.H. and Williams, J.C., "A Heat Shock Operon in *Coxiella burnetii* Produces a Major Antigen Homologous to a Protein in both Mycobacteria and *Escherichia coli*," *J. of Bacteriology*, 170(3):1227-1234 (1988).

Voellmy, et al., "Isolation and Functional Analysis . . . ," *PNAS*, 82:4949-4953 (1985).

Vogt, G., et al., "An Assessment of Amino Acid Exchange Matrices In Aligning Protein Sequences: The Twilight Zone Revisited," *J. Molec. Biol. 249*:816-831 (1995).

Vreden, S.G.S., et al., "Phase I Clinical Trial of a Recombinant Malaria Vaccine Consisting of the Circumsporozoite Repeat Region of Plasmodium Falciparum Coupled to Hepatitis B Surface Antigen," *Am. J. Trop. Med. Hyg.*, 45(5):533-538 (1991).

Walker, et al., "Escape From the Immune System," *Nature 407*:313-314 (2000).

Wang, T., et al., "Identification of the Peptide Biding Domain of hsc70," *J. Biol. Chem.*, 268(35):26049-26051 (1993).

Welch, W.J., et al., "Biochemical Characterization of the Mammalian Stress Proteins and Identification of Two Stress Proteins as Glucose—and $CA2+$—Ionophore-regulated Proteins," *J. Biol. Chem.*, 258(11): 7102-7111 (1983).

Welch, W.J. and Feramisco, J.R., "Rapid Purification of Mammalian 70,000-Dalton Stress Proteins: Affinity of the Proteins for Nucleotides," *Mol. & Cell. Biol.*, 3:1229-1237 (1985).

Welch, W.J. and Feramisco, J.R., "Purification of the Major Mammalian Heat Shock Proteins," *J. Biol. Chem. 257*(24):14949-14959 (1982).

Xu, L., et al., "Epitope Mapping and Characterization of the Infectious Hematopoietic Necrosis Virus Glycoprotein, Using Fusion Proteins Synthesized in *Escherichia coli*,", *J. Virol. 65*(3):1611-1615 (Mar. 1991).

Yewdell, et al., "The Binary Logic of Antigen Processing and Presentation to T Cells," *Cell 62*:203-206 (1990).

Young, D.B., et al., "The 65kDa antigen of mycobacteria—a common bacterial protein?," *Immunol. Today*, 8(7-8):215-219 (1987).

Young, R.A., "Stress Proteins and Immunology," *Annu. Rev. Immunol.*, 8:401-420 (1990).

Young, R.A., et al., "Genes for the major protein antigens of the leprosy parasite *Mycobacterium leprae*," *Nature*, 316:450-452 (1985).

Young, D., et al., "Stress proteins are immune targets in leprosy and tuberculosis," *Proc. Natl. Acad. Sci. USA*, 85:4267-4270 (1988).

Zavala, F., et al., "Synthetic Peptide Vaccine Confers Protection Against Murine Malaria," *J. Exp. Med.*, 166:1591-1596 (1987).

Zhu, X., et al., "Structural Analysis of Substrate Binding by the Molecular Chaperone DnaK," *Science 272*:1606-1614 (Jun. 14, 1996).

Zylicz, M., et al., "The grpE Protein of *Escherichia coli*," *J. Biol. Chem.*, 262(36):17437-17442 (1987).

Zylicz, M. and Georgopoulos, C., "Purification and Properties of the *Escherichia coli* dnaK Replication Protein," *J. Biol. Chem. 259*(14):8820-8825 (1984).

* cited by examiner

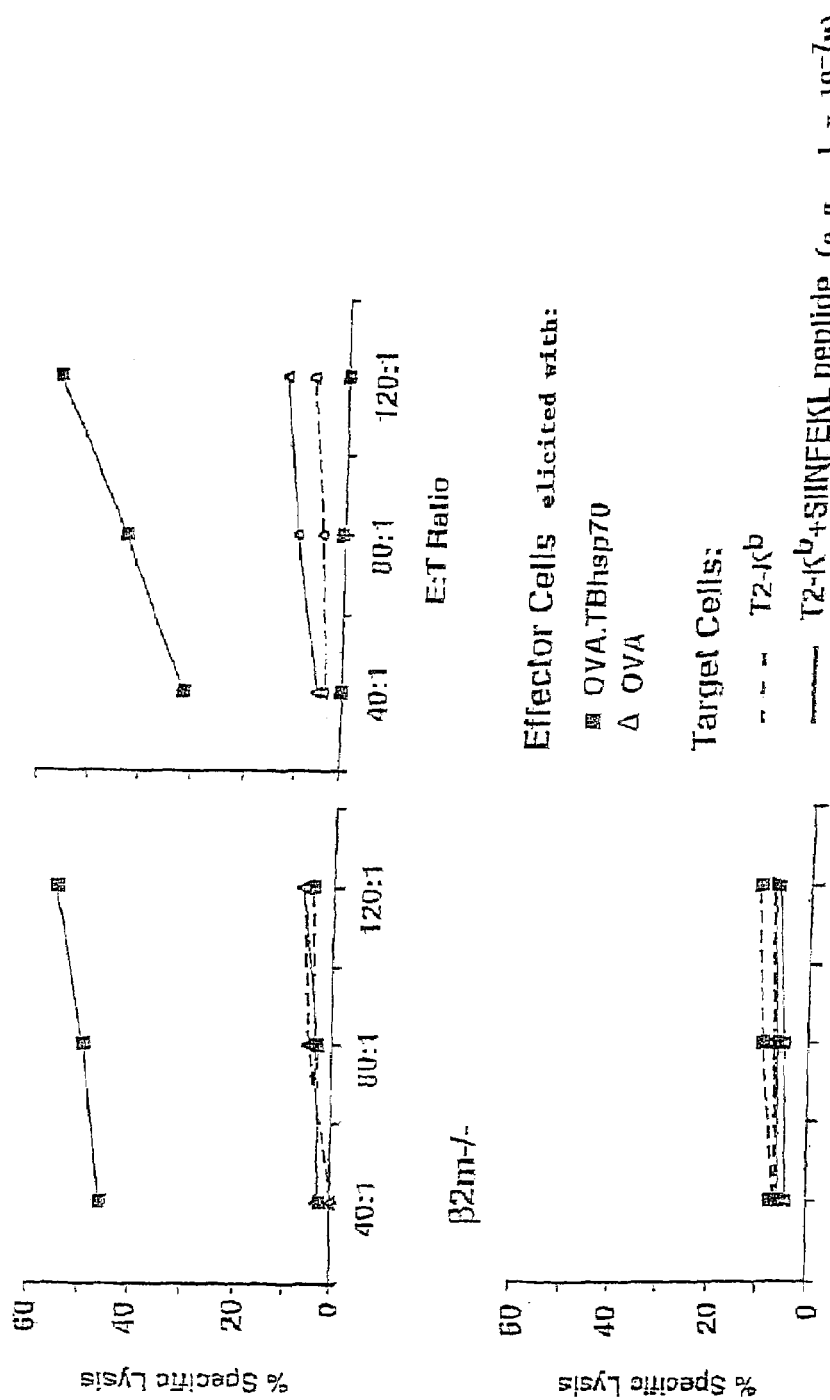
Figure 1A C57BL/6 (Wild Type)
Figure 1B CD4-/-
Figure 1C β2m-/-
Effector Cells elicited with:
■ OVA.TBhsp70
△ OVA
Target Cells:
- - - T2-K$^b$
——— T2-K$^b$+SIINFEKL peptide (e.g., 1 × 10$^{-7}$ M)

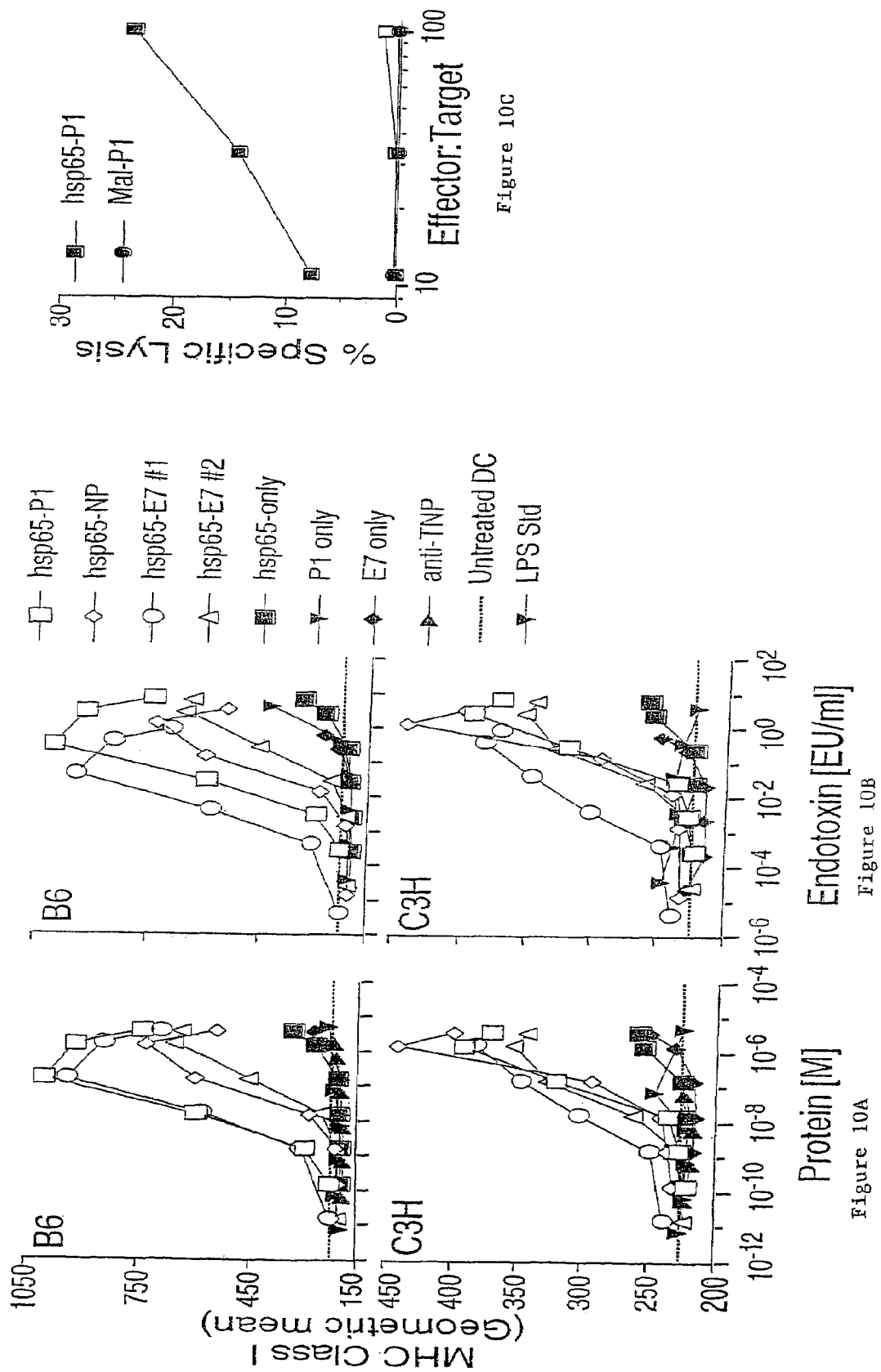

TBhsp70 (cDNA) -> Translate · 1-frame

DNA sequence   1879 bp   ATGGCTCGTGCG ... AGGCCAAGTGAC   linear

```
1/1                                                     31/11
ATG GCT CGT GCG GTC GGG ATC GAC CTC GGC ACC ACC AAC TCC GTC GTC TCG GTT CTC GAA
 M   A   R   A   V   G   I   D   L   G   T   T   N   S   V   V   S   V   L   E
61/21                                                   91/31
GGT GGC GAC CCG GTC CTC CTC CCC AAC TCC GAG GGC TCC AGG ACC ACC CCG TCA ATT GTC
 G   G   D   P   V   L   L   P   N   S   E   G   S   R   T   T   P   S   I   V
121/41                                                  151/51
GCC TTC GCC CGC AAC GGT GAG GTG CTG CTC GGC CAG CCC GCC AAG AAC CAG GCA GTG ACC
 A   F   A   R   N   G   E   V   L   L   G   Q   P   A   K   N   Q   A   V   T
181/61                                                  211/71
AAC GTC GAT CGC ACC GTG CGC TCG GTC AAG CGA CAC ATG GGC AGC GAC TGG TCC ATA GAG
 N   V   D   R   T   V   R   S   V   K   R   H   M   G   S   D   W   S   I   E
241/81                                                  271/91
ATT GAC GGC AAG AAA TAC ACC GCG CCG GAG ATC AGC GCC CGC ATT CTG ATG AAG CTC AAG
 I   D   G   K   K   Y   T   A   P   E   I   S   A   R   I   L   M   K   L   K
301/101                                                 331/111
CGC GAC GCC GAG GCC TAC CTC GGT GAG GAC ATT ACC GAC GCG GTT ATC ACG ACC CCC GCC
 R   D   A   E   A   Y   L   G   E   D   I   T   D   A   V   I   T   T   P   A
361/121                                                 391/131
TAC TTC AAT GAC GCC CAG CGT CAG GCC ACC AAG GAC GCC GGC CAG ATC GCC GGC CTC AAC
 Y   F   N   D   A   Q   R   Q   A   T   K   D   A   G   Q   I   A   G   L   N
421/141                                                 451/151
GTG CTG CGG ATC GTC AAC GAG CCG ACC GCG GCC GCG CTG GCC TAC GGC CTC GAC AAG GGC
 V   L   R   I   V   N   E   P   T   A   A   A   L   A   Y   G   L   D   K   G
481/161                                                 511/171
GAG AAG GAG CAG CGA ATC CTG GTC TTC GAC TTG GGT GGC GGC ACT TTC GAC GTT TCC CTG
 E   K   E   Q   R   I   L   V   F   D   L   G   G   G   T   F   D   V   S   L
541/181                                                 571/191
CTG GAG ATC GGC GAG GGT GTG GTT GAG GTC CGT GCC ACT TCG GGT GAC AAC CAC CTC GGC
 L   E   I   G   E   G   V   V   E   V   R   A   T   S   G   D   N   H   L   G
601/201                                                 631/211
GGC GAC GAC TGG GAC CAG CGG GTC GTC GAT TGG CTG GTG GAC AAG TTC AAG GGC ACC AGC
 G   D   D   W   D   Q   R   V   V   D   W   L   V   D   K   F   K   G   T   S
661/221                                                 691/231
GGC ATC GAT CTG ACC AAG GAC AAG ATG GCG ATG CAG CGG CTG CGG GAA GCC GCC GAG AAG
 G   I   D   L   T   K   D   K   M   A   M   Q   R   L   R   E   A   A   E   K
721/241                                                 751/251
GCA AAG ATC GAG CTG AGT TCG AGT CAG TCC ACC TCC ATC AAC CTG CCC TAC ATC ACC GTC
 A   K   I   E   L   S   S   S   Q   S   T   S   I   N   L   P   Y   I   T   V
781/261                                                 811/271
GAC GCC GAC AAG AAC CCG TTG TTC TTA GAC GAG CAG CTG ACC CGC GCC GAG TTC CAA CGG
 D   A   D   K   N   P   L   F   L   D   E   Q   L   T   R   A   E   F   Q   R
841/281                                                 871/291
ATC ACT CAG GAC CTG CTG GAC CGC ACT CGC AAG CCG TTC CAG TCG GTG ATC GCT GAC ACC
 I   T   Q   D   L   L   D   R   T   R   K   P   F   Q   S   V   I   A   D   T
901/301                                                 931/311
GGC ATT TCG GTG TCG GAG ATC GAT CAC GTT GTG CTC GTG GGT GGT TCG ACC CGG ATG CCC
 G   I   S   V   S   E   I   D   H   V   V   L   V   G   G   S   T   R   M   P
961/321                                                 991/331
GCG GTG ACC GAT CTG GTC AAG GAA CTC ACC GGC GGC AAG GAA CCC AAC AAG GGC GTC AAC
 A   V   T   D   L   V   K   E   L   T   G   G   K   E   P   N   K   G   V   N
1021/341                                                1051/351
CCC GAT GAG GTT GTC GCG GTG GGA GCC GCT CTG CAG GCC GGC GTC CTC AAG GGC GAG GTC
 P   D   E   V   V   A   V   G   A   A   L   Q   A   G   V   L   K   G   E   V
1081/361                                                1111/371
AAA GAC GTT CTG CTG CTT GAT GTT ACC CCG CTG ACC CTG GGT ATC GAG ACC AAG GGC GGG
 K   D   V   L   L   L   D   V   T   P   L   T   L   G   I   E   T   K   G   G
1141/381                                                1171/391
GTG ATG ACC AGG CTC ATC GAG CGC AAC ACC ACG ATC CCC ACC AAG CGG TCG CAG ACT TTC
 V   M   T   R   L   I   E   R   N   T   T   I   P   T   K   R   S   Q   T   F
1201/401                                                1231/411
ACC ACC GCC GAC GAC AAC CAA CCG TCG GTG CAG ATC CAG GTC TAT CAG GGC GAG CGT GAG
 T   T   A   D   D   N   Q   P   S   V   Q   I   Q   V   Y   Q   G   E   R   E
```

Figure 11

TBhsp70 (cDNA) -> Translate • 1-frame

DNA sequence    1979 bp    ATGGCTCGTCCG ... AGGCCAAGTGAC    linear

```
481/161                              511/171
GAG AAG GAG CAG CGA ATC CTG GTC TTC GAC TTC GGT GGT GGC ACT TTC GAC GTT TCC CTG
 E   K   E   Q   R   I   L   V   F   D   L   G   G   G   T   F   D   V   S   L
541/181                              571/191
CTG GAG ATC GGC GAG GGT GTC GTT GAG GTC CGT GCC ACT TCG GGT GAC AAC CAC CTC GGC
 L   E   I   G   E   G   V   V   E   V   R   A   T   S   G   D   N   H   L   G
601/201                              631/211
GGC GAC GAC TGG GAC CAG CGG GTC GTC GAT TGG CTC GTC GAC AAG TTC AAG GGC ACC AGC
 G   D   D   W   D   Q   R   V   V   D   W   L   V   D   K   F   K   G   T   S
661/221                              691/231
GGC ATC GAT CTG ACC AAG GAC AAG ATG GCG ATG CAG CGG CTC CGG GAA GCC GCC GAG AAG
 G   I   D   L   T   K   D   K   M   A   M   Q   R   L   R   E   A   A   E   K
721/241                              751/251
GCA AAG ATC GAG CTG AGT TCG AGT CAG TCC ACC TCG ATC AAC CTG CCC TAC ATC ACC GTC
 A   K   I   E   L   S   S   S   Q   S   T   S   I   N   L   P   Y   I   T   V
781/261                              811/271
GAC GCC GAC AAG AAC CCG TTG TTC TTA GAC GAG CAG CTG ACC CGG GCG GAG TTC CAA CGG
 D   A   D   K   N   P   L   F   L   D   E   Q   L   T   R   A   E   F   Q   R
841/281                              871/291
ATC ACT CAG GAC CTG CTG GAC CGC ACT CGC AAG CCG TTC CAG TCG GTG ATC GCT GAC ACC
 I   T   Q   D   L   L   D   R   T   R   K   P   F   Q   S   V   I   A   D   T
901/301                              931/311
GGC ATT TCG GTG TCG GAG ATC GAT CAC GTT GTG CTC GTG GGT GGT TCG ACC CGG ATG CCC
 G   I   S   V   S   E   I   D   H   V   V   L   V   G   G   S   T   R   M   P
961/321                              991/331
GCG GTG ACC GAT CTG GTC AAG GAA CTC ACC GGC GGC AAG GAA CCC AAG AAG GGC GTC AAC
 A   V   T   D   L   V   K   E   L   T   G   G   K   E   P   N   K   G   V   N
1021/341                             1051/351
CCC GAT GAG GTT GTC GCC GTG GGA GCC GCT CTG CAG GCC GGC GTC CTC AAG GGC GAG GTC
 P   D   E   V   V   A   V   G   A   A   L   Q   A   G   V   L   K   G   E   V
1081/361                             1111/371
AAA GAC GTT CTG CTG CTT GAT GTT ACC CCG
 K   D   V   L   L   L   D   V   T   P
```

Figure 12

```
murine hsp70.1 -> Translate · 1-frame

DNA sequence      1929 bp   ATGGCCAAGAAC ... GAGGTCGATTAG   linear

1/1                                  31/11
ATG GCC AAG AAC ACG GCG ATC GGC ATC GAC CTG GGT ACC ACC TAC TCG TGC GTG GGC GTG
 M   A   K   N   T   A   I   G   I   D   L   G   T   T   Y   S   C   V   G   V
61/21                                91/31
TTC CAG CAC GGC AAG GTG GAG ATC ATC GCC AAC GAC CAG GGC AAC CGC ACG ACC CCC AGC
 F   Q   H   G   K   V   E   I   I   A   N   D   Q   G   N   R   T   T   P   S
121/41                               151/51
TAC GTG GCC TTC ACC GAC ACC GAG CGC CTC ATC GGC GAC GCC GCC AAG AAC CAG GTG GCC
 Y   V   A   F   T   D   T   E   R   L   I   G   D   A   A   K   N   Q   V   A
181/61                               211/71
CTG AAC CCG CAG AAC ACC GTG TTC GAC GCG AAG CGG CTG ATC GGC CGC AAG TTC GGC GAT
 L   N   P   Q   N   T   V   F   D   A   K   R   L   I   G   R   K   F   G   D
241/81                               271/91
GCG GTG GTG CAG TCC GAC ATG AAG CAC TGG CCC TTC CAG GTG GTG AAC GAC GGC GAC AAG
 A   V   V   Q   S   D   M   K   H   W   P   F   Q   V   V   N   D   G   D   K
301/101                              331/111
CCC AAG GTG CAG GTG AAC TAC AAG GGC GAG AGC CGG TCG TTC TTC CCG GAG GAC ATC TCG
 P   K   V   Q   V   N   Y   K   G   E   S   R   S   F   F   P   E   E   I   S
361/121                              391/131
TCC ATG GTG CTG ACG AAG ATG AAG GAG ATC GCT GAG GCG TAC CTG GGC CAC CCG GTG ACC
 S   M   V   L   T   K   M   K   E   I   A   E   A   Y   L   G   H   P   V   T
421/141                              451/151
AAC GCG GTG ATC ACG GTG CCC GCC TAC TTC AAC GAC TCT CAG CGG CAG GCC ACC AAG GAC
 N   A   V   I   T   V   P   A   Y   F   N   D   S   Q   R   Q   A   T   K   D
481/161                              511/171
GCG GGC GTG ATC GCC GGT CTA AAC GTG CTG CGG ATC ATC AAC GAG CCC ACG GCG GCC GCC
 A   G   V   I   A   G   L   N   V   L   R   I   I   N   E   P   T   A   A   A
541/181                              571/191
ATC GCC TAC GGC CTG GAC CGG ACC GGC AAG GGC GAG CGC AAC GTG CTC ATC TTC GAC CTG
 I   A   Y   G   L   D   R   T   G   K   G   E   R   N   V   L   I   F   D   L
601/201                              631/211
GGG GGC GGC ACG TTC GAC GTG TCC ATC CTG ACG ATC GAC GAC GGC ATC TTC GAG GTG AAG
 G   G   G   T   F   D   V   S   I   L   T   I   D   D   G   I   F   E   V   K
661/221                              691/231
GCC ACG GCG GGC GAC ACG CAC CTG GGA GGG GAG GAC TTC GAC AAC CGG CTG GTG AGC CAC
 A   T   A   G   D   T   H   L   G   G   E   D   F   D   N   R   L   V   S   H
721/241                              751/251
TTC GTG GAG GAG TTC AAG AGG AAG CAC AAG AAG GAC ATC AGC CAG AAC AAG CGC GCC GTG
 F   V   E   E   F   K   R   K   H   K   K   D   I   S   Q   N   K   R   A   V
781/261                              811/271
CGG CGG CTG CGC ACG GCG TGT GAG AGG GCC AAG AGG ACG CTG TCG TCC AGC ACC CAG GCC
 R   R   L   R   T   A   C   E   R   A   K   R   T   L   S   S   S   T   Q   A
841/281                              871/291
AGC CTG GAG ATC GAC TCT CTG TTC GAG GGC ATC GAC TTC TAC ACA TCC ATC ACG CGG GCG
 S   L   E   I   D   S   L   F   E   G   I   D   F   Y   T   S   I   T   R   A
901/301                              931/311
CGG TTC GAA GAG CTG TGC TCG GAC CTC TTC CGC GGC ACG CTG GAG CCC GTC GAG AAG GCC
 R   F   E   E   L   C   S   D   L   F   R   G   T   L   E   P   V   E   K   A
961/321                              991/331
CTG CGC GAC GCC AAG ATG GAC AAG GCC CAG ATC CAC GAC CTG GTG CTG GTG GGC GGC TCG
 L   R   D   A   K   M   D   K   A   Q   I   H   D   L   V   L   V   G   G   S
1021/341                             1051/351
ACG CGC ATC CCC AAG GTG CAG AAG CTG CTG CAG GAC TTC TTC AAC GGG CGC GAC CTG AAC
 T   R   I   P   K   V   Q   K   L   L   Q   D   F   F   N   G   R   D   L   N
1081/361                             1111/371
AAG AGC ATC AAC CCG GAC GAG GCG GTG GCC TAC GGG GCG GCG GTG CAG GCG GCC ATC CTG
 K   S   I   N   P   D   E   A   V   A   Y   G   A   A   V   Q   A   A   I   L
1141/381                             1171/391
ATG GGG GAC AAG TCG GAG AAC GTG CAG GAC CTG CTG CTG CTG GAC GTG GCC CCG CTG TCC
 M   G   D   K   S   E   N   V   Q   D   L   L   L   L   D   V   A   P   L   S
1201/401                             1231/411
CTG GGC CTG GAG ACT GCC GGC GGC GTG ATG ACC GCC CTC ATC AAG CGC AAC TCC ACC ATC
 L   G   L   E   T   A   G   G   V   M   T   A   L   I   K   R   N   S   T   I
1261/421                             1291/431
CCC ACC AAG CAG ACC CAG ACC TTC ACC ACC TAC TCG GAC AAC CAG CCC GGC GTG CTG ATC
 P   T   K   Q   T   Q   T   F   T   T   Y   S   D   N   Q   P   G   V   L   I
```

Figure 13A murine hsp70.1 -> Translate • 1-frame

```
1321/441                              1351/451
CAG GTG TAC GAG GGC GAG AGG GCC ATG ACG CGC GAC AAC AAC CTG CTG GGG CGC TTC GAG
 Q   V   Y   E   G   E   R   A   M   T   R   D   N   N   L   L   G   R   F   E
1381/461                                      1411/471
CTG AGC GGC ATC CCG CCG GCG CCC ACG GGC GTC CCG CAG ATC GAG GTG ACC TTC GAC ATC
 L   S   G   I   P   P   A   P   T   G   V   P   Q   I   E   V   T   F   D   I
1441/481
GAC GCC AAC GGC ATC CTG AAC GTC ACG GCC ACC GAC AAG AGC ACC GGC AAG GCC AAC AAG
 D   A   N   G   I   L   N   V   T   A   T   D   K   S   T   G   K   A   N   K
1501/501                                      1531/511
ATC ACC ATC ACC AAC GAC AAG GGC CGC CTG AGC AAG GAG GAG ATC GAG CGC ATG GTG CAG
 I   T   I   T   N   D   K   G   R   L   S   K   E   E   I   E   R   M   V   Q
1561/521                                      1591/531
GAG GCC GAG CGC TAC AAG GCC GAG GAC GAG GTG CAG CGC GAC AGG GTG GCC GCC AAG AAC
 E   A   E   R   Y   K   A   E   D   E   V   Q   R   D   R   V   A   A   K   N
1621/541                                      1651/551
GCG CTC GAG TCC TAT GCC TTC AAC ATG AAG AGC GCC GTG GAG GAC GAG GGT CTC AAG GGC
 A   L   E   S   Y   A   F   N   M   K   S   A   V   E   D   E   G   L   K   G
1681/561                                      1711/571
AAG CTC AGC GAG GCT GAC AAG AAG AAG GTC CTG GAC AAG TGC CAG GAG GTC ATC TCC TGG
 K   L   S   E   A   D   K   K   K   V   L   D   K   C   Q   E   V   I   S   W
1741/581                                      1771/591
CTG GAC TCC AAC ACG CTG GCC GAC AAG GAG GAG TTC GTG CAC AAG CGG GAG GAG CTG GAG
 L   D   S   N   T   L   A   D   K   E   E   F   V   H   K   R   E   E   L   E
1801/601                                      1831/611
CGG GTG TGC AGC CCC ATC ATC AGT GGG CTG TAC CAG GGT GCG GGT GCT CCT GGG GCT GGG
 R   V   C   S   P   I   I   S   G   L   Y   Q   G   A   G   A   P   G   A   G
1861/621                                      1891/631
GGC TTC GGG GCC CAG GCG CCG CCG AAA GGA GCC TCT GGC TCA GGA CCC ACC ATC GAG GAG
 G   F   G   A   Q   A   P   P   K   G   A   S   G   S   G   P   T   I   E   E
1921/641
GTG GAT TAG
 V   D   *
```

Figure 13B murine hsp70.1 -> Translate · 1-frame

DNA sequence    1929 bp   ATGGCCAAGAAC ... GAGGTGGATTAG   linear

```
                                571/191
                              AAG GGC GAG CGC AAC GTG CTC ATC TTC GAC CTG
                               K   G   E   R   N   V   L   I   F   D   L
601/201                                       631/211
GGG GGC GGC ACG TTC GAC GTG TCC ATC CTG ACG ATC GAC GAC GGC ATC TTC GAG GTG AAG
 G   G   G   T   F   D   V   S   I   L   T   I   D   D   G   I   F   E   V   K
661/221                                       691/231
GCC ACG GCG GGC GAC ACG CAC CTG GGA GGG GAG GAC TTC GAC AAC CGG CTG GTG AGC CAC
 A   T   A   G   D   T   H   L   G   G   E   D   F   D   N   R   L   V   S   H
721/241                                       751/251
TTC GTG GAG GAG TTC AAG AGG AAG CAC AAG AAG GAC ATC AGC CAG AAC AAG CGC GCC GTG
 F   V   E   E   F   K   R   K   H   K   K   D   I   S   Q   N   K   R   A   V
781/261                                       811/271
CGG CGG CTG CGC ACG GCG TGT GAG AGG GCC AAG AGG ACG CTG TCG TCC AGC ACC CAG GCC
 R   R   L   R   T   A   C   E   R   A   K   R   T   L   S   S   S   T   Q   A
841/281                                       871/291
AGC CTG GAG ATC GAC TCT CTG TTC GAG GGC ATC GAC TTC TAC ACA TCC ATC ACG CGG GCG
 S   L   E   I   D   S   L   F   E   G   I   D   F   Y   T   S   I   T   R   A
901/301                                       931/311
CGG TTC GAA GAG CTG TGC TCG GAC CTC TTC CGC GGC ACG CTG GAG CCC GTG GAG AAC CCC
 R   F   E   E   L   C   S   D   L   F   R   G   T   L   E   P   V   E   N   P
961/321                                       991/331
CTG CGC GAC GCC AAG ATG GAC AAG GCC CAG ATC CAC GAC CTG GTG CTG GTG GGC GGC TCG
 L   R   D   A   K   M   D   K   A   Q   I   H   D   L   V   L   V   G   G   S
1021/341                                      1051/351
ACG CGC ATC CCC AAG GTG CAG AAG CTG CTC CAG GAC TTC TTC AAC GGG CGC GAC CTG AAC
 T   R   I   P   K   V   Q   K   L   L   Q   D   F   F   N   G   R   D   L   N
1081/361                                      1111/371
AAG AGC ATC AAC CCG GAC GAG GCG GTG GCC TAC GGG GCG GCG GTG CAG GCG GCC ATC CTG
 K   S   I   N   P   D   E   A   V   A   Y   G   A   A   V   Q   A   A   I   L
1141/381                                      1171/391
ATG GGG GAC AAG TCG GAG AAC GTG CAG GAC CTG CTG CTG CTG GAC GTG GCC CCC
 M   G   D   K   S   E   N   V   Q   D   L   L   L   L   D   V   A   P
```

Figure 14

SEQUENCE LISTING

<160> NUMBER OF SEQ ID NOS: 25

<210> SEQ ID NO 1
<211> LENGTH: 8
<212> TYPE: PRT
<213> ORGANISM: Unknown
<220> FEATURE:
<223> OTHER INFORMATION: Peptide Liberated From P1

<400> SEQUENCE: 1

Ser Ile Tyr Arg Tyr Tyr Gly Leu
1               5

<210> SEQ ID NO 2
<211> LENGTH: 8
<212> TYPE: PRT
<213> ORGANISM: Unknown
<220> FEATURE:
<223> OTHER INFORMATION: Ova Peptide

<400> SEQUENCE: 2

Ser Ile Ile Asn Phe Glu Lys Leu
1               5

<210> SEQ ID NO 3
<211> LENGTH: 8
<212> TYPE: PRT
<213> ORGANISM: Unknown
<220> FEATURE:
<223> OTHER INFORMATION: Alpha KG Peptide

<400> SEQUENCE: 3

Leu Ser Pro Phe Pro Phe Asp Leu

<210> SEQ ID NO 4
<211> LENGTH: 5
<212> TYPE: PRT
<213> ORGANISM: Unknown
<220> FEATURE:
<223> OTHER INFORMATION: Octapeptide

<400> SEQUENCE: 4

Ser Tyr Arg Gly Leu
 1               5

<210> SEQ ID NO 5
<211> LENGTH: 1260
<212> TYPE: DNA
<213> ORGANISM: Unknown
<220> FEATURE:
<223> OTHER INFORMATION: Mycobacterium Tuberculosis hsp70 cDNA
<220> FEATURE:
<221> NAME/KEY: CDS
<222> LOCATION: (1)...(1260)

<400> SEQUENCE: 5

| | |
|---|---|
| atg gct cgt gcg gtc ggg atc gac ctc ggg acc acc aac tcc gtc gtc<br>Met Ala Arg Ala Val Gly Ile Asp Leu Gly Thr Thr Asn Ser Val Val<br>1               5                  10                  15 | 48 |
| tcg gtt ctg gaa ggt ggc gac ccg gtc gtc gtc gcc aac tcc gag ggc<br>Ser Val Leu Glu Gly Gly Asp Pro Val Val Val Ala Asn Ser Glu Gly<br>            20                  25                  30 | 96 |
| tcc agg acc acc ccg tca att gtc gcg ttc gcc cgc aac ggt gag gtg<br>Ser Arg Thr Thr Pro Ser Ile Val Ala Phe Ala Arg Asn Gly Glu Val<br>        35                  40                  45 | 144 |
| ctg gtc ggc cag ccc gcc aag aac cag gca gtg acc aac gtc gat cgc<br>Leu Val Gly Gln Pro Ala Lys Asn Gln Ala Val Thr Asn Val Asp Arg<br>    50                  55                  60 | 192 |
| acc gtg cgc tcg gtc aag cga cac atg ggc agc gac tgg tcc ata gag<br>Thr Val Arg Ser Val Lys Arg His Met Gly Ser Asp Trp Ser Ile Glu<br>65                  70                  75                  80 | 240 |
| att gac ggc aag aaa tac acc gcg ccg gag atc agc gcc cgc att ctg<br>Ile Asp Gly Lys Lys Tyr Thr Ala Pro Glu Ile Ser Ala Arg Ile Leu<br>                85                  90                  95 | 288 |
| atg aag ctg aag cgc gac gcc gag gcc tac ctc ggt gag gac att acc<br>Met Lys Leu Lys Arg Asp Ala Glu Ala Tyr Leu Gly Glu Asp Ile Thr<br>            100                 105                 110 | 336 |
| gac gcg gtt atc acg acg ccc gcc tac ttc aat gac gcc cag cgt cag<br>Asp Ala Val Ile Thr Thr Pro Ala Tyr Phe Asn Asp Ala Gln Arg Gln<br>        115                 120                 125 | 384 |
| gcc acc aag gac gcc ggc cag atc gcc ggc ctc aac gtg ctg cgg atc<br>Ala Thr Lys Asp Ala Gly Gln Ile Ala Gly Leu Asn Val Leu Arg Ile<br>    130                 135                 140 | 432 |
| gtc aac gag ccg acc gcg gcc gcg ctg gcc tac ggc ctc gac aag ggc<br>Val Asn Glu Pro Thr Ala Ala Ala Leu Ala Tyr Gly Leu Asp Lys Gly<br>145                 150                 155                 160 | 480 |
| gag aag gag cag cga atc ctg gtc ttc gac ttg ggt ggt ggc act ttc<br>Glu Lys Glu Gln Arg Ile Leu Val Phe Asp Leu Gly Gly Gly Thr Phe<br>                165                 170                 175 | 528 |
| gac gtt tcc ctg ctg gag atc ggc gag ggt gtg gtt gag gtc cgt gcc<br>Asp Val Ser Leu Leu Glu Ile Gly Glu Gly Val Val Glu Val Arg Ala<br>            180                 185                 190 | 576 |
| act tcg ggt gac aac cac ctc ggc ggc gac gac tgg gac cag cgg gtc<br>Thr Ser Gly Asp Asn His Leu Gly Gly Asp Asp Trp Asp Gln Arg Val<br>        195                 200                 205 | 624 |

```
gtc gat tgg ctg gtg gac aag ttc aag ggc acc agc ggc atg gat ctg       672
Val Asp Trp Leu Val Asp Lys Phe Lys Gly Thr Ser Gly Met Asp Leu
210                 215                 220 acc aag gac aag atg gcg atg cag cgg ctg cgg gaa gcc gcc gag aag       720
Thr Lys Asp Lys Met Ala Met Gln Arg Leu Arg Glu Ala Ala Glu Lys
225                 230                 235                 240 gca aag atc gag ctg agt tcg agt cag tcc acc tcg atc aac ctg ccc       768
Ala Lys Ile Glu Leu Ser Ser Ser Gln Ser Thr Ser Ile Asn Leu Pro
                245                 250                 255 tac atc acc gtc gac gcc gac aag aac ccg ttg ttc tta gac gag cag       816
Tyr Ile Thr Val Asp Ala Asp Lys Asn Pro Leu Phe Leu Asp Glu Gln
            260                 265                 270 ctg acc cgc gcg gag ttc caa cgg atc act cag gac ctg ctg gac cgc       864
Leu Thr Arg Ala Glu Phe Gln Arg Ile Thr Gln Asp Leu Leu Asp Arg
        275                 280                 285 act cgc aag ccg ttc cag tcg gtg atc gct gac acc ggc att tcg gtg       912
Thr Arg Lys Pro Phe Gln Ser Val Ile Ala Asp Thr Gly Ile Ser Val
    290                 295                 300 tcg gag atc gat cac gtt gtg ctc gtg ggt ggt tcg acc cgg atg ccc       960
Ser Glu Ile Asp His Val Val Leu Val Gly Gly Ser Thr Arg Met Pro
305                 310                 315                 320 gcg gtg acc gat ctg gtc aag gaa ctc acc ggc ggc aag gaa ccc aac      1008
Ala Val Thr Asp Leu Val Lys Glu Leu Thr Gly Gly Lys Glu Pro Asn
                325                 330                 335 aag ggc gtc aac ccc gat gag gtt gtc gcg gtg gga gcc gct ctg cag      1056
Lys Gly Val Asn Pro Asp Glu Val Val Ala Val Gly Ala Ala Leu Gln
            340                 345                 350 gcc ggc gtc ctc aag ggc gag gtg aaa gac gtt ctg ctg ctt gat gtt      1104
Ala Gly Val Leu Lys Gly Glu Val Lys Asp Val Leu Leu Leu Asp Val
        355                 360                 365 acc ccg ctg agc ctg ggt atc gag acc aag ggc ggg gtg atg acc agg      1152
Thr Pro Leu Ser Leu Gly Ile Glu Thr Lys Gly Gly Val Met Thr Arg
    370                 375                 380 ctc atc gag cgc aac acc acg atc ccc acc aag cgg tcg gag act ttc      1200
Leu Ile Glu Arg Asn Thr Thr Ile Pro Thr Lys Arg Ser Glu Thr Phe
385                 390                 395                 400 acc acc gcc gac gac aac caa ccg tcg gtg cag atc cag gtc tat cag      1248
Thr Thr Ala Asp Asp Asn Gln Pro Ser Val Gln Ile Gln Val Tyr Gln
                405                 410                 415 ggg gag cgt gag                                                      1260
Gly Glu Arg Glu
            420

<210> SEQ ID NO 6
<211> LENGTH: 420
<212> TYPE: PRT
<213> ORGANISM: Unknown
<220> FEATURE:
<223> OTHER INFORMATION: Mycobacterium Tuberculosis hsp70 cDNA

<400> SEQUENCE: 6

Met Ala Arg Ala Val Gly Ile Asp Leu Gly Thr Thr Asn Ser Val Val
 1               5                  10                  15

Ser Val Leu Glu Gly Gly Asp Pro Val Val Ala Asn Ser Glu Gly
            20                  25                  30

```
Thr Val Arg Ser Val Lys Arg His Met Gly Ser Asp Trp Ser Ile Glu
 65                  70                  75                  80

Ile Asp Gly Lys Lys Tyr Thr Ala Pro Glu Ile Ser Ala Arg Ile Leu
                 85                  90                  95

Met Lys Leu Lys Arg Asp Ala Glu Ala Tyr Leu Gly Glu Asp Ile Thr
            100                 105                 110

Asp Ala Val Ile Thr Thr Pro Ala Tyr Phe Asn Asp Ala Gln Arg Gln
            115                 120                 125

Ala Thr Lys Asp Ala Gly Gln Ile Ala Gly Leu Asn Val Leu Arg Ile
130                 135                 140

Val Asn Glu Pro Thr Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
            195                 200                 205

Val Asp Trp Leu Val Asp Lys Phe Lys Gly Thr Ser Gly Met Asp Leu
210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
            260                 265                 270

Leu Thr Arg Ala Glu Phe Gln Arg Ile Thr Gln Asp Leu Leu Asp Arg
            275                 280                 285

Thr Arg Lys Pro Phe Gln Ser Val Ile Ala Asp Thr Gly Ile Ser Val
290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Lys Glu Pro Asn
                325                 330                 335

Lys Gly Val Asn Pro Asp Glu Val Val Ala Val Gly Ala Ala Leu Gln
            340                 345                 350

Ala Gly Val Leu Lys Gly Glu Val Lys Asp Val Leu Leu Leu Asp Val
            355                 360                 365

Thr Pro Leu Ser Leu Gly Ile Glu Thr Lys Gly Gly Val Met Thr Arg
370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu
            420

<210> SEQ ID NO 7
<211> LENGTH: 630
<212> TYPE: DNA
<213> ORGANISM: Unknown
<220> FEATURE:
<223> OTHER INFORMATION: Segment II of TBhsp70
<220> FEATURE:
<221> NAME/KEY: CDS
<222> LOCATION: (1)...(630)
```

-continued

<223> OTHER INFORMATION: Segment II of TBhsp70

<400> SEQUENCE: 7

```
gag aag gag cag cga atc ctg gtc ttc gac ttg ggt ggt ggc act ttc      48
Glu Lys Glu Gln Arg Ile Leu Val Phe Asp Leu Gly Gly Gly Thr Phe
 1               5                  10                  15 gac gtt tcc ctg ctg gag atc ggc gag ggt gtg gtt gag gtc cgt gcc      96
Asp Val Ser Leu Leu Glu Ile Gly Glu Gly Val Val Glu Val Arg Ala
             20                  25                  30 act tcg ggt gac aac cac ctc ggc ggc gac gac tgg gac cag cgg gtc     144
Thr Ser Gly Asp Asn His Leu Gly Gly Asp Asp Trp Asp Gln Arg Val
         35                  40                  45 gtc gat tgg ctg gtg gac aag ttc aag ggc acc agc ggc atg gat ctg     192
Val Asp Trp Leu Val Asp Lys Phe Lys Gly Thr Ser Gly Met Asp Leu
     50                  55                  60 acc aag gac aag atg gcg atg cag cgg ctg cgg gaa gcc gcc gag aag     240
Thr Lys Asp Lys Met Ala Met Gln Arg Leu Arg Glu Ala Ala Glu Lys
 65                  70                  75                  80 gca aag atc gag ctg agt tcg agt cag tcc acc tcg atc aac ctg ccc     288
Ala Lys Ile Glu Leu Ser Ser Ser Gln Ser Thr Ser Ile Asn Leu Pro
                 85                  90                  95 tac atc acc gtc gac gcc gac aag aac ccg ttg ttc tta gac gag cag     336
Tyr Ile Thr Val Asp Ala Asp Lys Asn Pro Leu Phe Leu Asp Glu Gln
            100                 105                 110 ctg acc cgc gcg gag ttc caa cgg atc act cag gac ctg ctg gac cgc     384
Leu Thr Arg Ala Glu Phe Gln Arg Ile Thr Gln Asp Leu Leu Asp Arg
        115                 120                 125 act cgc aag ccg ttc cag tcg gtg atc gct gac acc ggc att tcg gtg     432
Thr Arg Lys Pro Phe Gln Ser Val Ile Ala Asp Thr Gly Ile Ser Val
    130                 135                 140 tcg gag atc gat cac gtt gtg ctc gtg ggt ggt tcg acc cgg atg ccc     480
Ser Glu Ile Asp His Val Val Leu Val Gly Gly Ser Thr Arg Met Pro
145                 150                 155                 160 gcg gtg acc gat ctg gtc aag gaa ctc acc ggc ggc aag gaa ccc aac     528
Ala Val Thr Asp Leu Val Lys Glu Leu Thr Gly Gly Lys Glu Pro Asn
                165                 170                 175 aag ggc gtc aac ccc gat gag gtt gtc gcg gtg gga gcc gct ctg cag     576
Lys Gly Val Asn Pro Asp Glu Val Val Ala Val Gly Ala Ala Leu Gln
            180                 185                 190 gcc ggc gtc ctc aag ggc gag gtg aaa gac gtt ctg ctg ctt gat gtt     624
Ala Gly Val Leu Lys Gly Glu Val Lys Asp Val Leu Leu Leu Asp Val
        195                 200                 205 acc ccg                                                              630
Thr Pro
    210
```

<210> SEQ ID NO 8
<211> LENGTH: 210
<212> TYPE: PRT
<213> ORGANISM: Unknown
<220> FEATURE:
<223> OTHER INFORMATION: Segment II of TBhsp70

<400> SEQUENCE: 8

```
Glu Lys Glu Gln Arg Ile Leu Val Phe Asp Leu Gly Gly Gly Thr Phe
 1               5                  10                  15

Asp Val Ser Leu Leu Glu Ile Gly Glu Gly Val Val Glu Val Arg Ala
             20                  25                  30

Thr Ser Gly Asp Asn His Leu Gly Gly Asp Asp Trp Asp Gln Arg Val
         35                  40                  45
```

```
Val Asp Trp Leu Val Asp Lys Phe Lys Gly Thr Ser Gly Met Asp Leu
 50                  55                  60

Thr Lys Asp Lys Met Ala Met Gln Arg Leu Arg Glu Ala Ala Glu Lys
 65                  70                  75                  80

Ala Lys Ile Glu Leu Ser Ser Ser Gln Ser Thr Ser Ile Asn Leu Pro
                 85                  90                  95

Tyr Ile Thr Val Asp Ala Asp Lys Asn Pro Leu Phe Leu Asp Glu Gln
             100                 105                 110

Leu Thr Arg Ala Glu Phe Gln Arg Ile Thr Gln Asp Leu Leu Asp Arg
         115                 120                 125

Thr Arg Lys Pro Phe Gln Ser Val Ile Ala Asp Thr Gly Ile Ser Val
     130                 135                 140

Ser Glu Ile Asp His Val Val Leu Val Gly Gly Ser Thr Arg Met Pro
145                 150                 155                 160

Ala Val Thr Asp Leu Val Lys Glu Leu Thr Gly Gly Lys Glu Pro Asn
                165                 170                 175

Lys Gly Val Asn Pro Asp Glu Val Val Ala Val Gly Ala Ala Leu Gln
            180                 185                 190

Ala Gly Val Leu Lys Gly Glu Val Lys Asp Val Leu Leu Leu Asp Val
        195                 200                 205

Thr Pro
    210

<210> SEQ ID NO 9
<211> LENGTH: 1929
<212> TYPE: DNA
<213> ORGANISM: Unknown
<220> FEATURE:
<223> OTHER INFORMATION: Murine hsp70
<220> FEATURE:
<221> NAME/KEY: CDS
<222> LOCATION: (1)...(1929)
<223> OTHER INFORMATION: Murine hsp70

<400> SEQUENCE: 9 atg gcc aag aac acg gcg atc ggc atc gac ctg ggc acc acc tac tcg      48
Met Ala Lys Asn Thr Ala Ile Gly Ile Asp Leu Gly Thr Thr Tyr Ser
  1               5                  10                  15 tgc gtg ggc gtg ttc cag cac ggc aag gtg gag atc atc gcc aac gac      96
Cys Val Gly Val Phe Gln His Gly Lys Val Glu Ile Ile Ala Asn Asp
                 20                  25                  30 cag ggc aac cgc acg acc ccc agc tac gtg gcc ttc acc gac acc gag     144
Gln Gly Asn Arg Thr Thr Pro Ser Tyr Val Ala Phe Thr Asp Thr Glu
             35                  40                  45 cgc ctc atc ggg gac gcc gcc aag aac cag gtg gcg ctg aac ccg cag     192
Arg Leu Ile Gly Asp Ala Ala Lys Asn Gln Val Ala Leu Asn Pro Gln
         50                  55                  60 aac acc gtg ttc gac gcg aag cgg ctg atc ggc cgc aag ttc ggc gat     240
Asn Thr Val Phe Asp Ala Lys Arg Leu Ile Gly Arg Lys Phe Gly Asp
 65                  70                  75                  80 gcg gtg gtg cag tcc gac atg aag cac tgg ccc ttc cag gtg gtg aac     288
Ala Val Val Gln Ser Asp Met Lys His Trp Pro Phe Gln Val Val Asn
                 85                  90                  95 gac ggc gac aag ccc aag gtg cag gtg aac tac aag ggc gag agc cgg     336
Asp Gly Asp Lys Pro Lys Val Gln Val Asn Tyr Lys Gly Glu Ser Arg
            100                 105                 110 tcg ttc ttc ccg gag gag atc tcg tcc atg gtg ctg acg aag atg aag     384
Ser Phe Phe Pro Glu Glu Ile Ser Ser Met Val Leu Thr Lys Met Lys
        115                 120                 125
```

-continued

```
gag atc gct gag gcg tac ctg ggc cac ccg gtg acc aac gcg gtg atc        432
Glu Ile Ala Glu Ala Tyr Leu Gly His Pro Val Thr Asn Ala Val Ile
    130                 135                 140 acg gtg ccc gcc tac ttc aac gac tct cag cgg cag gcc acc aag gac        480
Thr Val Pro Ala Tyr Phe Asn Asp Ser Gln Arg Gln Ala Thr Lys Asp
145                 150                 155                 160 gcg ggc gtg atc gcc ggt cta aac gtg ctg cgg atc atc aac gag ccc        528
Ala Gly Val Ile Ala Gly Leu Asn Val Leu Arg Ile Ile Asn Glu Pro
                165                 170                 175 acg gcg gcc gcc atc gcc tac ggg ctg gac cgg acc ggc aag ggc gag        576
Thr Ala Ala Ala Ile Ala Tyr Gly Leu Asp Arg Thr Gly Lys Gly Glu
            180                 185                 190 cgc aac gtg ctc atc ttc gac ctg ggg ggc ggc acg ttc gac gtg tcc        624
Arg Asn Val Leu Ile Phe Asp Leu Gly Gly Gly Thr Phe Asp Val Ser
        195                 200                 205 atc ctg acg atc gac gac ggc atc ttc gag gtg aag gcc acg gcg ggc        672
Ile Leu Thr Ile Asp Asp Gly Ile Phe Glu Val Lys Ala Thr Ala Gly
    210                 215                 220 gac acg cac ctg gga ggg gag gac ttc gac aac cgg ctg gtg agc cac        720
Asp Thr His Leu Gly Gly Glu Asp Phe Asp Asn Arg Leu Val Ser His
225                 230                 235                 240 ttc gtg gag gag ttc aag agg aag cac aag aag gac atc agc cag aac        768
Phe Val Glu Glu Phe Lys Arg Lys His Lys Lys Asp Ile Ser Gln Asn
                245                 250                 255 aag cgc gcg gtg cgg cgg ctg cgc acg gcg tgt gag agg gcc aag agg        816
Lys Arg Ala Val Arg Arg Leu Arg Thr Ala Cys Glu Arg Ala Lys Arg
            260                 265                 270 acg ctg tcg tcc agc acc cag gcc agc ctg gag atc gac tct ctg ttc        864
Thr Leu Ser Ser Ser Thr Gln Ala Ser Leu Glu Ile Asp Ser Leu Phe
        275                 280                 285 gag ggc atc gac ttc tac aca tcc atc acg cgg gcg cgg ttc gaa gag        912
Glu Gly Ile Asp Phe Tyr Thr Ser Ile Thr Arg Ala Arg Phe Glu Glu
    290                 295                 300 ctg tgc tcg gac ctg ttc cgc ggc acg ctg gag ccc gtg gag aag gcc        960
Leu Cys Ser Asp Leu Phe Arg Gly Thr Leu Glu Pro Val Glu Lys Ala
305                 310                 315                 320 ctg cgc gac gcc aag atg gac aag gcc cag atc cac gac ctg gtg ctg       1008
Leu Arg Asp Ala Lys Met Asp Lys Ala Gln Ile His Asp Leu Val Leu
                325                 330                 335 gtg ggc ggc tcg acg cgc atc ccc aag gtg cag aag ctg ctg cag gac       1056
Val Gly Gly Ser Thr Arg Ile Pro Lys Val Gln Lys Leu Leu Gln Asp
            340                 345                 350 ttc ttc aac ggg cgc gac ctg aac aag agc atc aac ccg gac gag gcg       1104
Phe Phe Asn Gly Arg Asp Leu Asn Lys Ser Ile Asn Pro Asp Glu Ala
        355                 360                 365 gtg gcc tac ggg gcg gcg gtg cag gcg gcc atc ctg atg ggg gac aag       1152
Val Ala Tyr Gly Ala Ala Val Gln Ala Ala Ile Leu Met Gly Asp Lys
    370                 375                 380 tcg gag aac gtg cag gac ctg ctg ctg ctg gac gtg gcg ccc ctg tcg       1200
Ser Glu Asn Val Gln Asp Leu Leu Leu Leu Asp Val Ala Pro Leu Ser
385                 390                 395                 400 ctg ggc ctg gag act gcg ggc ggc gtg atg acg gcg ctc atc aag cgc       1248
Leu Gly Leu Glu Thr Ala Gly Gly Val Met Thr Ala Leu Ile Lys Arg
                405                 410                 415 aac tcc acc atc ccc acc aag cag acg cag acc ttc acc acc tac tcg       1296
Asn Ser Thr Ile Pro Thr Lys Gln Thr Gln Thr Phe Thr Thr Tyr Ser
            420                 425                 430 gac aac cag ccc ggg gtg ctg atc cag gtg tac gag ggc gag agg gcc       1344
Asp Asn Gln Pro Gly Val Leu Ile Gln Val Tyr Glu Gly Glu Arg Ala
        435                 440                 445
```

-continued

```
atg acg cgc gac aac aac ctg ctg ggg cgc ttc gag ctg agc ggc atc     1392
Met Thr Arg Asp Asn Asn Leu Leu Gly Arg Phe Glu Leu Ser Gly Ile
    450                 455                 460 ccg ccg gcg ccc agg ggc gtg ccg cag atc gag gtg acc ttc gac atc     1440
Pro Pro Ala Pro Arg Gly Val Pro Gln Ile Glu Val Thr Phe Asp Ile
465                 470                 475                 480 gac gcc aac ggc atc ctg aac gtc acg gcc acc gac aag agc acc ggc     1488
Asp Ala Asn Gly Ile Leu Asn Val Thr Ala Thr Asp Lys Ser Thr Gly
                485                 490                 495 aag gcc aac aag atc acc atc acc aac gac aag ggc cgc ctg agc aag     1536
Lys Ala Asn Lys Ile Thr Ile Thr Asn Asp Lys Gly Arg Leu Ser Lys
            500                 505                 510 gag gag atc gag cgc atg gtg cag gag gcc gag cgc tac aag gcc gag     1584
Glu Glu Ile Glu Arg Met Val Gln Glu Ala Glu Arg Tyr Lys Ala Glu
        515                 520                 525 gac gag gtg cag cgc gac agg gtg gcc gcc aag aac gcg ctc gag tcc     1632
Asp Glu Val Gln Arg Asp Arg Val Ala Ala Lys Asn Ala Leu Glu Ser
    530                 535                 540 tat gcc ttc aac atg aag agc gcc gtg gag gac gag ggt ctc aag ggc     1680
Tyr Ala Phe Asn Met Lys Ser Ala Val Glu Asp Glu Gly Leu Lys Gly
545                 550                 555                 560 aag ctc agc gag gct gac aag aag aag gtc ctg gac aag tgc cag gag     1728
Lys Leu Ser Glu Ala Asp Lys Lys Lys Val Leu Asp Lys Cys Gln Glu
                565                 570                 575 gtc atc tcc tgg ctg gac tcc aac acg ctg gcc gac aag gag gag ttc     1776
Val Ile Ser Trp Leu Asp Ser Asn Thr Leu Ala Asp Lys Glu Glu Phe
            580                 585                 590 gtg cac aag cgg gag gag ctg gag cgg gtg tgc agc ccc atc atc agt     1824
Val His Lys Arg Glu Glu Leu Glu Arg Val Cys Ser Pro Ile Ile Ser
        595                 600                 605 ggg ctg tac cag ggt gcg ggt gct cct ggg gct ggg ggc ttc ggg gcc     1872
Gly Leu Tyr Gln Gly Ala Gly Ala Pro Gly Ala Gly Gly Phe Gly Ala
    610                 615                 620 cag gcg ccg ccg aaa gga gcc tct ggc tca gga ccc acc atc gag gag     1920
Gln Ala Pro Pro Lys Gly Ala Ser Gly Ser Gly Pro Thr Ile Glu Glu
625                 630                 635                 640 gtg gat tag                                                          1929
Val Asp *
```

<210> SEQ ID NO 10
<211> LENGTH: 642
<212> TYPE: PRT
<213> ORGANISM: Unknown
<220> FEATURE:
<223> OTHER INFORMATION: Murine hsp70

<400> SEQUENCE: 10

```
Met Ala Lys Asn Thr Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Ala Val Val Gln Ser Asp Met Lys His Trp Pro Phe Gln Val Val Asn
                85                  90                  95
```

```
Asp Gly Asp Lys Pro Lys Val Gln Val Asn Tyr Lys Gly Glu Ser Arg
            100                 105                 110

Ser Phe Phe Pro Glu Glu Ile Ser Ser Met Val Leu Thr Lys Met Lys
        115                 120                 125

Glu Ile Ala Glu Ala Tyr Leu Gly His Pro Val Thr Asn Ala Val Ile
        130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
            195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Ser His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
        290                 295                 300

Leu Cys Ser Asp Leu Phe Arg Gly Thr Leu Glu Pro Val Glu Lys Ala
305                 310                 315                 320

Leu Arg Asp Ala Lys Met Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
            435                 440                 445

Met Thr Arg Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510
```

```
Glu Glu Ile Glu Arg Met Val Gln Glu Ala Glu Arg Tyr Lys Ala Glu
            515                 520                 525

Asp Glu Val Gln Arg Asp Arg Val Ala Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Leu Ser Glu Ala Asp Lys Lys Val Leu Asp Lys Cys Gln Glu
            565                 570                 575

Val Ile Ser Trp Leu Asp Ser Asn Thr Leu Ala Asp Lys Glu Glu Phe
        580                 585                 590

Val His Lys Arg Glu Glu Leu Glu Arg Val Cys Ser Pro Ile Ile Ser
            595                 600                 605

Gly Leu Tyr Gln Gly Ala Gly Ala Pro Gly Ala Gly Gly Phe Gly Ala
        610                 615                 620

Gln Ala Pro Pro Lys Gly Ala Ser Gly Ser Gly Pro Thr Ile Glu Glu
625                 630                 635                 640

Val Asp

<210> SEQ ID NO 11
<211> LENGTH: 627
<212> TYPE: DNA
<213> ORGANISM: Unknown
<220> FEATURE:
<223> OTHER INFORMATION: Murine hsp70 -Segment II
<220> FEATURE:
<221> NAME/KEY: CDS
<222> LOCATION: (1)...(627)
<223> OTHER INFORMATION: Murine hsp70 -Segment II

<400> SEQUENCE: 11 aag ggc gag cgc aac gtg ctc atc ttc gac ctg ggg ggc ggc acg ttc      48
Lys Gly Glu Arg Asn Val Leu Ile Phe Asp Leu Gly Gly Gly Thr Phe
  1               5                  10                  15 gac gtg tcc atc ctg acg atc gac gac ggc atc ttc gag gtg aag gcc     96
Asp Val Ser Ile Leu Thr Ile Asp Asp Gly Ile Phe Glu Val Lys Ala
             20                  25                  30 acg gcg ggc gac acg cac ctg gga ggg gag gac ttc gac aac cgg ctg    144
Thr Ala Gly Asp Thr His Leu Gly Gly Glu Asp Phe Asp Asn Arg Leu
         35                  40                  45 gtg agc cac ttc gtg gag gag ttc aag agg aag cac aag aag gac atc    192
Val Ser His Phe Val Glu Glu Phe Lys Arg Lys His Lys Lys Asp Ile
 50                  55                  60 agc cag aac aag cgc gcg gtg cgg cgg ctg cgc acg gcg tgt gag agg    240
Ser Gln Asn Lys Arg Ala Val Arg Arg Leu Arg Thr Ala Cys Glu Arg
 65                  70                  75                  80 gcc aag agg acg ctg tcg tcc agc acc cag gcc agc ctg gag atc gac    288
Ala Lys Arg Thr Leu Ser Ser Ser Thr Gln Ala Ser Leu Glu Ile Asp
             85                  90                  95 tct ctg ttc gag ggc atc gac ttc tac aca tcc atc acg cgg gcg cgg    336
Ser Leu Phe Glu Gly Ile Asp Phe Tyr Thr Ser Ile Thr Arg Ala Arg
         100                 105                 110 ttc gaa gag ctg tgc tcg gac ctg ttc cgc ggc acg ctg gag ccc gtg    384
Phe Glu Glu Leu Cys Ser Asp Leu Phe Arg Gly Thr Leu Glu Pro Val
     115                 120                 125 gag aag gcc ctg cgc gac gcc aag atg gac aag gcc cag atc cac gac    432
Glu Lys Ala Leu Arg Asp Ala Lys Met Asp Lys Ala Gln Ile His Asp
130                 135                 140 ctg gtg ctg gtg ggc ggc tcg acg cgc atc ccc aag gtg cag aag ctg    480
Leu Val Leu Val Gly Gly Ser Thr Arg Ile Pro Lys Val Gln Lys Leu
145                 150                 155                 160
```

```
ctg cag gac ttc ttc aac ggg cgc gac ctg aac aag agc atc aac ccg      528
Leu Gln Asp Phe Phe Asn Gly Arg Asp Leu Asn Lys Ser Ile Asn Pro
            165                 170                 175 gac gag gcg gtg gcc tac ggg gcg gcg gtg cag gcg gcc atc ctg atg      576
Asp Glu Ala Val Ala Tyr Gly Ala Ala Val Gln Ala Ala Ile Leu Met
        180                 185                 190 ggg gac aag tcg gag aac gtg cag gac ctg ctg ctg ctg gac gtg gcg      624
Gly Asp Lys Ser Glu Asn Val Gln Asp Leu Leu Leu Leu Asp Val Ala
    195                 200                 205 ccc                                                                   627
Pro
```

<210> SEQ ID NO 12
<211> LENGTH: 209
<212> TYPE: PRT
<213> ORGANISM: Unknown
<220> FEATURE:
<223> OTHER INFORMATION: Murine hsp70 - Segment II

<400> SEQUENCE: 12

```
Lys Gly Glu Arg Asn Val Leu Ile Phe Asp Leu Gly Gly Gly Thr Phe
  1               5                  10                  15

Asp Val Ser Ile Leu Thr Ile Asp Gly Ile Phe Glu Val Lys Ala
             20                  25                  30

Thr Ala Gly Asp Thr His Leu Gly Gly Glu Asp Phe Asp Asn Arg Leu
         35                  40                  45

Val Ser His Phe Val Glu Glu Phe Lys Arg Lys His Lys Lys Asp Ile
 50                  55                  60

Ser Gln Asn Lys Arg Ala Val Arg Arg Leu Arg Thr Ala Cys Glu Arg
 65                  70                  75                  80

Ala Lys Arg Thr Leu Ser Ser Ser Thr Gln Ala Ser Leu Glu Ile Asp
                 85                  90                  95

Ser Leu Phe Glu Gly Ile Asp Phe Tyr Thr Ser Ile Thr Arg Ala Arg
            100                 105                 110

Phe Glu Glu Leu Cys Ser Asp Leu Phe Arg Gly Thr Leu Glu Pro Val
        115                 120                 125

Glu Lys Ala Leu Arg Asp Ala Lys Met Asp Lys Ala Gln Ile His Asp
    130                 135                 140

Leu Val Leu Val Gly Gly Ser Thr Arg Ile Pro Lys Val Gln Lys Leu
145                 150                 155                 160

Leu Gln Asp Phe Phe Asn Gly Arg Asp Leu Asn Lys Ser Ile Asn Pro
                165                 170                 175

Asp Glu Ala Val Ala Tyr Gly Ala Ala Val Gln Ala Ala Ile Leu Met
            180                 185                 190

Gly Asp Lys Ser Glu Asn Val Gln Asp Leu Leu Leu Leu Asp Val Ala
        195                 200                 205

Pro
```

<210> SEQ ID NO 13
<211> LENGTH: 47
<212> TYPE: DNA
<213> ORGANISM: Unknown
<220> FEATURE:
<223> OTHER INFORMATION: PCR Primer oQH025

<400> SEQUENCE: 13
gcagtactca tatgatcctg gagcttccat tgccagtgg gacaatg      47

-continued

<210> SEQ ID NO 14
<211> LENGTH: 63
<212> TYPE: DNA
<213> ORGANISM: Unknown
<220> FEATURE:
<223> OTHER INFORMATION: PCR Primer oQH027

<400> SEQUENCE: 14
ctccgacctc acctacgacg ttcgcagaga cttcttaaaa ttatccgatc gcctagacct     60
agt                                                                  63

<210> SEQ ID NO 15
<211> LENGTH: 44
<212> TYPE: DNA
<213> ORGANISM: Unknown
<220> FEATURE:
<223> OTHER INFORMATION: PCR Primer oQH001

<400> SEQUENCE: 15
atagtactgg atccatggct cgtgcggtcg ggatcgacct cggg                     44

<210> SEQ ID NO 16
<211> LENGTH: 36
<212> TYPE: DNA
<213> ORGANISM: Unknown
<220> FEATURE:
<223> OTHER INFORMATION: PCR Primer oJR061

<400> SEQUENCE: 16
ggaattccta tctagtcact tgccctcccg gccgtc                              36

<210> SEQ ID NO 17
<211> LENGTH: 49
<212> TYPE: DNA
<213> ORGANISM: Unknown
<220> FEATURE:
<223> OTHER INFORMATION: PCR Primer oQH011

<400> SEQUENCE: 17
gtcgacgaat tcatcatcag attcgctgct ccttctcgcc cttgtcgag                49

<210> SEQ ID NO 18
<211> LENGTH: 48
<212> TYPE: DNA
<213> ORGANISM: Unknown
<220> FEATURE:
<223> OTHER INFORMATION: PCR Primer oQH012

<400> SEQUENCE: 18
gtcgacggat ccatggagaa ggagcagcga atcctggtct tcgacttg                 48

<210> SEQ ID NO 19
<211> LENGTH: 48
<212> TYPE: DNA
<213> ORGANISM: Unknown
<220> FEATURE:
<223> OTHER INFORMATION: PCR Primer oQH014

<400> SEQUENCE: 19
gtcgacggat ccatggtgaa agacgttctg ctgcttgatg ttaccccg                 48

<210> SEQ ID NO 20
<211> LENGTH: 48
<212> TYPE: DNA
<213> ORGANISM: Unknown

-continued

```
<220> FEATURE:
<223> OTHER INFORMATION: PCR Primer oQH016

<400> SEQUENCE: 20
gtcgacggat ccatgcgtaa tcaagccgag acattggtct accagacg                48

<210> SEQ ID NO 21
<211> LENGTH: 49
<212> TYPE: DNA
<213> ORGANISM: Unknown
<220> FEATURE:
<223> OTHER INFORMATION: PCR Primer oQH013

<400> SEQUENCE: 21
gtcgacgaat tcatcacggg gtaacatcaa gcagcagaac gtctttcac               49

<210> SEQ ID NO 22
<211> LENGTH: 49
<212> TYPE: DNA
<213> ORGANISM: Unknown
<220> FEATURE:
<223> OTHER INFORMATION: PCR Primer oQH015

<400> SEQUENCE: 22
gtcgacgaat tcatcagacc aatgtctcgg cttgattacg aacatcggc               49

<210> SEQ ID NO 23
<211> LENGTH: 33
<212> TYPE: DNA
<213> ORGANISM: Unknown
<220> FEATURE:
<223> OTHER INFORMATION: PCR Primer oJR12

<400> SEQUENCE: 23
tctagaggat ccatggccaa gaacacggcg atc                                33

<210> SEQ ID NO 24
<211> LENGTH: 39
<212> TYPE: DNA
<213> ORGANISM: Unknown
<220> FEATURE:
<223> OTHER INFORMATION: PCR Primer oJR103

<400> SEQUENCE: 24
tctagagaat tcctaatcca cctcctcgat ggtgggtcc                          39

<210> SEQ ID NO 25
<211> LENGTH: 24
<212> TYPE: PRT
<213> ORGANISM: Unknown
<220> FEATURE:
<223> OTHER INFORMATION: P1 Peptide

<400> SEQUENCE: 25

Ile Lys Val Ser Gly Leu Glu Gln Leu Glu Ser Ile Tyr Arg Tyr Tyr
 1               5                  10                  15

Gly Leu Leu Leu Lys Glu Ala Tyr
            20
```

VIVO CTL ELICITATION BY HEAT SHOCK PROTEIN FUSION PROTEINS MAPS TO A DISCRETE DOMAIN AND IS CD4+ T CELL-INDEPENDENT

RELATED APPLICATIONS

This application is a divisional of U.S. application Ser. No. 09/761,534, filed on Jan. 16, 2001 (now U.S. Pat. No. 6,875, 435), which is a continuation of International Application No. PCT/US00/32831, which designated the United States and was filed on Dec. 1, 2000, which is published in English, and which claims the benefit of U.S. Provisional Application No. 60/176,143, filed on Jan. 14, 2000. The entire teachings of the above applications are incorporated herein by reference.

GOVERNMENT SUPPORT

The invention was supported, in part, by National Institutes of Health (NIH) training grant 5T32-AI-07463, NIH Cancer Center core grant CA-14051 and NIH research grants AI44476 and AI44478. The Government has certain rights in the invention.

BACKGROUND OF THE INVENTION

When injected into an individual with diverse adjuvants, protein antigens usually stimulate the production of high-affinity IgG antibodies, indicating that they activate CD4 T helper cells, as well as B cells. These procedures generally fail, however, to elicit effective CD8 T cell responses. The reason, according to current views, is that the short peptides needed, in association with MHC class I molecules, to stimulate CD8 T cells arise from proteolytic cleavage of cytosolic proteins. Since injected protein antigens are generally unable to cross cellular lipid membranes, they fail to gain entry to the proper cytosolic "MHC class I processing pathway" and are thus unable to stimulate the production of CD8 T cells. Although there is evidence for alternative cellular pathways for processing some exogenous proteins to form peptide MHC class I complexes (Sigal, L. J., et al., *Nature*, 398:77-80 (1999) and Gromme, M., et al., *Proc. Natl. Acad. Sci. USA*, 96:10326-10331 (1999)) it remains generally true that protein antigens normally fail to stimulate significant CD8 CTL responses (Rock, K., *Today*, 17:131-137 (1996)).

There is now substantial evidence that heat shock proteins (hsps) isolated from tumors can be used as adjuvant-free anti-tumor vaccines in animals; hsp70 and the distantly related chaperones gp96 and calreticulin share this immunostimulatory activity (Udono, H. and Srivastava, P. K., *J. Exp. Med.*, 178:1391-1396 (1993); Udono, H., et al., *Proc. Natl. Acad. Sci. USA*, 91:3077-3081 (1994); Suto, R. and Srivastava, P. K., *Science*, 269:1585-1588 (1995); Blanchere, N. E., et al., *J. Exp. Med.*, 186:1315-1322 (1997); Tamura, Y., et al., *Science*, 278:117-120 (1997) and Nair, S., et al., *J. Immunol.*, 162:6426-6432 (1999)). The fusion of large polypeptides (80-110 amino acids in length) to mycobacterial hsp70 (TBhsp70) creates potent immunogens that can elicit MHC class I-restricted, CD8+ cytotoxic T cell responses sufficient to mediate rejection of tumors expressing the fusion partner (Suzue, K., et al., *Proc. Natl. Acad. Sci. USA*, 94:13146-13151 (1997)).

The means by which soluble hsp70 fusion proteins stimulate CD8 cytotoxic T cell (CTL) responses are unknown. Among the possible mechanisms are: 1) strong hsp-specific CD4+ helper cell responses that enhance what might otherwise be a minimal response to the soluble proteins (Barrios, C., et al., *Eur. J. Immunol.*, 22:1365-1372 (1992); Suzue, K. and Young, R. A., *J. Immunol.*, 156:873-876 (1996); Horwitz, M. S., et al., *Nature Med.*, 4:781-785 (1998) and Könen-Waisman, S., et al., *J. Infect. Dis.*, 179:403-413 (1999)); and 2) chaperone function of hsps delivers the fusion protein to intracellular compartments of antigen-presenting cells for processing into short peptides and loading onto MHC class I (Young, R. A., *Ann. Rev. Immunol.*, 8:401-420 (1990) and Schild, H., et al., *Curr. Opinion Imm.*, 11:109-113 (1999)). An understanding of the ability of hsp70 to stimulate CD8+ CTL responses is needed to provide for more effective immunological prophylaxis and therapy for cancer and infectious diseases caused by intracellular pathogens.

SUMMARY OF THE INVENTION

The present invention is based on the discovery that a heat shock protein (hsp; hsps are also known in the art as stress proteins), or a discrete domain thereof, that is joined to a heterologous molecule can produce a CD8+ cytotoxic (cytolytic) lymphocyte (CTL) response in a host to which it is administered. The domain can be, for example, about half (e.g., 40, 45, 50, 55, or 60%) of the adenosinetriphosphate (ATP) binding domain of an hsp. Moreover, the response is independent of CD4+ CTLs. Accordingly, the invention features compositions that include an hsp, or all or a portion of an hsp ATP binding domain, joined to a heterologous molecule and methods of inducing a CD8+ CTL response to a molecule in an individual (e.g., a patient, such as a human patient, who has a deficiency of CD4+ T cells) by administering that composition to the individual. The method can be used to treat a patient who has an acquired immune deficiency syndrome (AIDS) by, for example, administering to the patient an hsp, or a portion of an ATP binding domain of an hsp, that is joined to a molecule associated with a human immunodeficiency virus (HIV), such as an HIV antigen.

The invention has numerous advantages. For example, the compositions and methods described herein provide for highly effective CD8+ CTL responses. These responses are useful in treating (i.e., preventing or reducing the length or severity of symptoms associated with a disease process or preventing or attenuating the cellular events through which those symptoms are made manifest; treatment may be effective without completely eradicating all symptoms) diseases that are caused by or otherwise associated with intracellular pathogens. Diseases or conditions that are characterized by a deficiency (or complete lack of) CD4+ T cells are particularly amenable to treatment.

BRIEF DESCRIPTION OF THE DRAWINGS

FIG. 1A is a graph of effector cell to target cell ratio (E:T) versus % specific lysis illustrating OVA-specific CTL elicited by immunization with OVA.TBhsp70 fusion protein without adjuvant in the splenocytes from wild-type C57/BL/6 mice.

FIG. 1B is a graph of E:T versus % specific lysis illustrating OVA-specific CTL elicited by immunization with OVA.T-Bhsp70 fusion protein without adjuvant in the splenocytes from CD4+ knockout mice (CD4 −/− mice).

FIG. 1C is a graph of E:T versus % specific lysis illustrating OVA-specific CTL elicited by immunization with OVA.T-Bhsp70 fusion protein without adjuvant in the splenocytes from mice which have very few CD8+ T cells (β2m −/− mice).

FIG. 10A is a pair of graphs of dendritic cell MHC class I expression plotted as a function of protein concentration of the added hsp fusion proteins and control proteins. Upper panel; dendritic cells from C57BL/6 mice. Lower panel; dendritic cells from C3H mice. Purified bone marrow derived dendritic cells were incubated for 24 hr with various concentrations of hsp65-P1 or other hsp65 fusion proteins, having as fusion partners influenza virus nucleoprotein (hsp65-NP) or human papilloma virus, type 16, E7 subunit (hsp65-E7 preparations #1 and #2) or with controls (hsp65 alone, P1 alone, E7 alone, an anti-TNP IgG antibody). MHC Class I protein levels on the dendritic cells were then determined by flow cytometry by gating on propidium iodide-negative CD11c⁺ cells and using the Y3 antibody which recognizes both H-2$^b$ ($K^b$) and H-2$^k$ MHC class I. MHC class I levels are shown as geometric mean fluorescence; the levels on untreated dendritic cells are represented by a dashed horizontal line.

FIG. 10B is a pair of graphs of the dendritic cell MHC class I expression values from FIG. 10A and are plotted as a function of endotoxin concentration (calculated from the endotoxin levels present in the added hsp fusion proteins and other proteins). Upper panel; dendritic cells from C57BL/6 mice. Lower panel: dendritic cells from C3H mice.

FIG. 10C is a graph showing that Hsp65-P1 stimulates production of CTL (anti-SYRGL) in CD4-deficient (CD4⁻/⁻) mice. As in FIG. 6A-6C the mice were injected s.c. twice, one wk apart, with 100 μg of hsp65-P1 or Ma1-P1 in PBS. One wk following the second injection, cells from spleen and draining lymph nodes were pooled and restimulated with 1 μM SYRGL peptide without addition of exogenous cytokines. Six days later the cells were used as effectors in a standard 4 hr cytolytic assay at various E:T ratios using ⁵¹Cr-labeled T2-K$^b$ cells as targets in the presence of 1 μM SYRGL. Lysis of T2-K$^b$ cells in absence of SYRGL is shown by unfilled symbols.

FIG. 11 is the nucleotide (cDNA) (SEQ ID NO: 5) and amino acid (SEQ ID NO: 6) sequences of *Mycobacterium tuberculosis* hsp70 (TBhsp70) wherein segment II (nucleotides 481-1110; amino acids 161-370) is highlighted.

FIG. 12 is the nucleotide (SEQ ID NO: 7) and amino acid (SEQ ID NO: 8) sequences of segment II of TBhsp70.

FIGS. 13A-13B are the nucleotide (SEQ ID NO: 9) and amino acid (SEQ ID NO: 10) sequences of murine hsp70 wherein segment II (nucleotides 568-1194; amino acids 190-398) is highlighted.

FIG. 14 is the nucleotide (SEQ ID NO: 11) and amino acid (SEQ ID NO: 12) sequences of segement II of murine hsp70.

DETAILED DESCRIPTION OF THE INVENTION

Figures 2A, 2B:
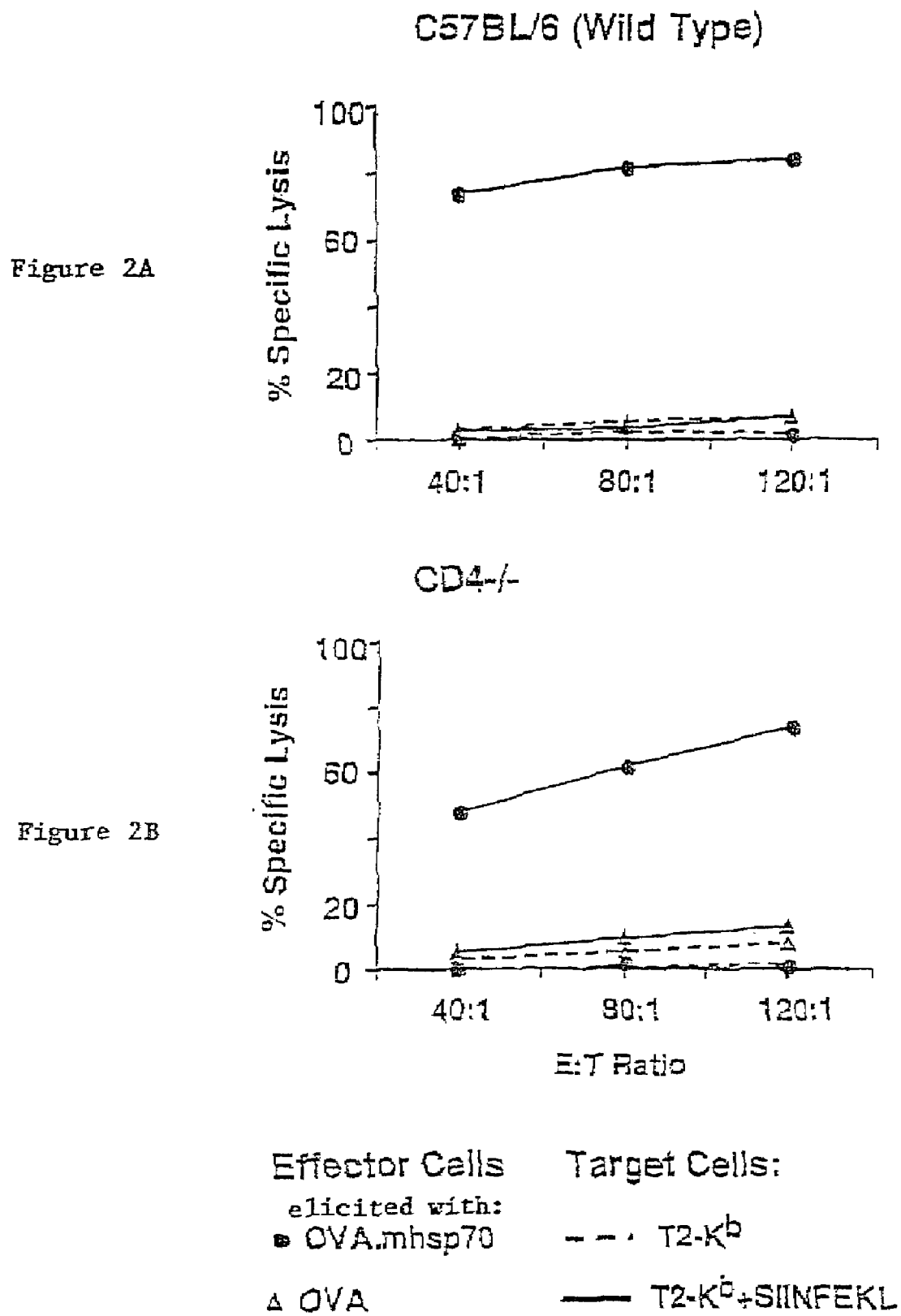
FIG. 2A is a graph of E:T versus % specific lysis illustrating murine hsp70 fusion protein elicits CTL responses in wild-type C57BL/6 mice.
FIG. 2B is a graph of E:T versus % specific lysis illustrating murine hsp70 fusion protein elicits CTL responses in CD4 −/− mice.

An immunological response to a molecule that, notably, includes a CD8⁺ CTL response, can be evoked in an individual by administering to that individual either an hsp joined to that molecule or a portion of an ATP binding domain of an hsp joined to that molecule (the molecule being virtually any biological substance, naturally- or nonnaturally-occurring with the exception of a portion of a stress protein). The CD8⁺ CTL response can be evoked in an individual who has a deficiency of CD4⁺ T cells (i.e. a CD4⁺ T cell count considered by any routinely used medical standard to be physiologically abnormal). Physicians and others having ordinary skill in the art can identify such individuals, which include patients infected with HIV. Accordingly, patients who are infected with HIV, or at risk of becoming so, can be treated with either an hsp joined to an HIV antigen (e.g., p24 or gp41) or a portion of an ATP binding domain of an hsp joined to an HIV antigen (e.g., p24 or gp41). Physicians and others having ordinary skill in the art can recognize and use other molecules associated with the HIV.

Heat shock proteins useful in the present invention are those that have an ATP binding domain and those that, when administered to an individual, induce a CD8⁺ T cell response to a molecule to which they are joined. Full length hsps (e.g., hsp70 and hsp65) can be used, as can the ATP binding domains of hsps (or portions thereof). For example, the hsp moiety joined to the molecule can be the amino-terminal portion of the ATP binding domain. For example, the hsp moiety joined to the molecule can include or consist of about half of the ATP binding domain. For example, the hsp moiety can include or consist of about 25 to about 365 consecutive amino acid residues (e.g. 25-350, 50-300, 110-275, 125-250, 130-225, 135-200, 150-200, 170-190, or 100-200 residues) of the ATP binding domain. More specifically, the hsp moiety can include or consist of amino acid residues 161-370 of *Mycobacterium tuberculosis* hsp70 or amino acid residues 190-398 of murine hsp70. Portions of hsp65 that are homologous to segment II of hsp70 (e.g. mycobacterial hsp65 such as *Mycobacterium bovis* BCG; mammalian hsp65, such as murine, canine, porcine, equine or human hsp65) can be used as described herein.

Those of ordinary skill in the art are well able to identify hsps and ATP binding domains within those proteins. Moreover, those artisans can make substitutions, if desired, in the sequences of these proteins or their domains that do not substantially reduce the abilities of those proteins or their domains to effectively induce CD8⁺ T cell responses. Amino acid substitutions can be made on the basis of similarity in polarity, charge, solubility, hydrophobicity, hydrophilicity, or the amphipathic nature of the residues involved. For example, the nonpolar (hydrophobic) amino acid residues alanine, leucine, isoleucine, valine, proline, phenylalanine, tryptophan, and methionine can be substituted one for another; polar neutral amino acid residues such as glycine, serine, threonine, cysteine, tyrosine, asparagine, and glutamine can be substituted one for another; positively charged (basic) amino acid residues such as arginine, lysine, and histidine can be substituted one for another; and negatively charged (acidic) amino acid residues such as aspartic acid and glutamic acid can be substituted one for another. For example, the hsp moiety used as described herein can include 1-25% conservative amino acid substitutions.

Any hsp or any portion of the hsp ATP binding domain can be purified from natural sources, recombinantly produced, or chemically synthesized. For example, an hsp or a portion thereof can be obtained from mycobacteria (e.g., *Mycobacterium tuberculosis, Mycobacterium bovis, Mycobacterium leprae*, or *Mycobacterium smegmatis*), mammals (e.g. a murine, canine, porcine, equine, or human), fungi, parasite, or bacteria. Methods for recombinantly producing hsps or portions thereof are also well known (production in bacteria such as *E. coli*) are described herein. In addition, the hsp or the portion thereof can be obtained from a commercial supplier.

Molecules useful in the present methods include any molecule against which a $CD4^+$ independent immune response is desired. A "molecule" includes, but is not limited to, proteins or fragments thereof (e.g., proteolytic fragments), peptides (e.g., synthetic peptides or polypeptides), antigens, glycoproteins, carbohydrates (e.g., polysaccharides and oligosaccharides), lipids, glycolipids, DNA (e.g., recombinant DNA), killed or attenuated whole organisms (e.g., viruses, bacteria, mycobacteria, parasites or fungi) or portions thereof, toxins, toxoids or any other organic molecule.

Molecules useful in the present methods can be obtained from a variety of sources using techniques routinely practiced in the art. For example, the molecule can be obtained from pathogens or organisms such as bacteria, mycobacteria, viruses, fungi or parasites. While the molecule can be isolated (e.g., purified or partially purified (e.g. physically separated from at least 50% of the biological substances with which it naturally associates), it can also be chemically synthesized, recombinantly produced, or purchased from a commercial supplier.

The hsp or portion thereof is "joined" to a molecule against which an immune response is desired. The term "joined" includes covalent attachment of the hsp, or a portion thereof, to the molecule. The conjugation can be carried out using techniques routinely practiced in the art (e.g., by forming a covalent bond between the hsp, or the portion thereof, and the molecule or by reductive amination). The term "joined" also includes fused proteins, such as those created by recombinant techniques or chemical synthesis. The fusion protein can include the molecule fused to the amino-terminal region or the C-terminal region of the hsp, or the portion thereof.

The $CD8^+$ CTL responses induced by the methods of the present invention can be used for prophylaxis and/or therapy of diseases or conditions, particularly those characterized by a lack or deficiency of $CD4^+$ T cells. That is, the hsp or portion thereof joined to the molecule against which an immune response is desired can be administered to an individual either before or after a disease or condition is manifested and can result in prevention, amelioration, elimination or delay in the onset or progression of the disease state. For example, the present invention can be used to prevent or treat an individual positive for human immunodeficiency virus (HIV) and the opportunistic infections associated with HIV. In one embodiment, the HIV positive individual is deficient in $CD4^+$ T cells.

In the methods of the present invention, an effective amount of the hsp or portion thereof joined to the molecule against which an immune response is desired is administered to an individual (e.g., mammal such as human). As used herein an "effective amount" is an amount that induces a $CD4^+$ T cell independent immune response to the molecule in an individual. In a particular embodiment, an "effective amount" is an amount such that when administered to an individual, it results in an enhanced $CD8^+$ CTL response to the molecule relative to the $CD8^+$ CTL response to the molecule in an individual to whom an effective amount was not administered. For example, an effective amount or dosage of the hsp or portion thereof joined to the molecule against which an immune response is desired is in the range of about 50 pmoles to about 5000 pmole. In one embodiment, the dosage range if from about 80 pmole to about 3500 pmoles; in another embodiment, the dosage range is from about 100 pmoles to about 2000 pmoles; and in a further embodiment the dosage range is from about 120 pmoles to about 1000 pmoles. The appropriate dosage of hsp or portion thereof joined to the molecule against which an immune response is desired for each individual will be determined by taking into consideration, for example, the particular hsp and/or molecule being administered, the type of individual to whom the composition is being administered, the age and size of the individual, the condition or disease being treated or prevented and the severity of the condition or disease. Those skilled in the art will be able to determine using no more than routine experimentation the appropriate dosage to administer to an individual.

The hsp or portion thereof joined to the molecule against which the immune response is desired can be administered to the individual in a variety of ways. The routes include intradermal, transdermal, (e.g., slow release polymers), intramuscular, intraperitoneal, intravenous, subcutaneous, oral, epidural and intranasal routes. Any other convenient route of administration can be used, for example, infusion or bolus injection, infusion of multiple injections over time, or absorption through epithelial or mucocutaneous linings. In addition, the hsp joined to the molecule can be administered with other components or biologically active agents, such as adjuvants, pharmaceutically acceptable surfactants (e.g., glycerides), excipients, (e.g., lactose), liposomes, carriers, diluents and vehicles.

Further, in the embodiment in which the molecule is a protein (peptide), the hsp or portion thereof joined to the molecule can be administered by in vivo expression of polynucleotides encoding such into an individual. For example, the hsp or portion thereof and/or the molecule can be administered to an individual using a vector, wherein the vector which includes the hsp or portion thereof joined to the molecule is administered under conditions in which the hsp or portion thereof and the molecule are expressed in vivo.

Several expression system vectors that can be used are available commercially or can be produced according to recombinant DNA and cell culture techniques. For example, vector systems such as yeast or vaccinia virus expression systems, or virus vectors can be used in the methods and compositions of the present invention (Kaufman, R. J., *J. Meth. Cell and Molec. Biol.*, 2:221-236 (1990)). Other techniques using naked plasmids or DNA, and cloned genes encapsulated in targeted liopsomes or in erythrocyte ghosts can be used to introduce the hsp or portion joined to the molecule into the host (Friedman, T., *Science*, 244:1275-1281 (1991); Rabinovich, N. R., et al., *Science*, 265:1410-1404 (1994)). The construction of expression vectors and the transfer of vectors and nucleic acids into various host cells can be accomplished using genetic engineering techniques, as described in manuals like *Molecular Cloning* and *Current Protocols in Molecular Biology*, which are incorporated by reference, or by using commercially available kits (Sambrook, J. et al., *Molecular Cloning*, Cold Spring Harbor Press, 1989; Ausubel, F. M., et al., *Current Protocols in Molecular Biology*, Greene Publishing Associates and Wiley-Interscience, 1989).

As demonstrated in Example 1, hsp70 fusion proteins elicit $CD8^+$ CTL in the absence of $CD4^+$ T lymphocytes and this function resides in a 200-amino acid segment of TBhsp70, indicating that chaperone activity is not required. To gain insights into the mechanisms by which soluble hsp fusions can elicit $CD8^+$ CTL against the fusion partner, hsp70 was dissected to ascertain whether a particular hsp domain is necessary, and knockout mice were used to determine whether the fusion protein's immunogenicity is dependent on $CD4^+$ T lymphocytes. It was found that the ability to elicit $CD8^+$ CTL depends on a discrete 200-amino acid protein domain, indicating that the fusion protein's immunogenicity for $CD8^+$ T cells does not require coupled chaperone function or peptide binding. Further, it was found that ovalbumin-.hsp70 fusion protein elicited anti-ovalbumin CD8+ CTL about equally well in CD4 knockout and wild-type C57BL/6 mice, and also when the hsp70 was of mycobacterial (*Mycobacterium tuberculosis*) or murine (self) origin. The ability of hsp70 fusion proteins to elicit CD4-independent CTL responses indicates that hsp70 fusion proteins can be used for immunological prophylaxis and therapy against disease in CD4+ T cell deficient individuals.

As demonstrated in Example 2, a mycobacterial heat shock protein, 65 kDa (hsp65), fused to a polypeptide (P1) that contains an octapeptide (SIYRYYGL (SEQ ID NO: 1)) agonist for a particular T cell receptor (2C TCR) stimulated C57BL/6 mice, as well as CD4-deficient mice, to produce CD8+ cytolytic T lymphocytes (CTL) to the fusion partner's octapeptide. This and other hsp65 fusion proteins, but not native hsp65 itself, stimulated dendritic cells, in vitro and in vivo, to upregulate the levels of MHC (class I and II) and costimulatory (B7.2) molecules. The results provide a mechanism for the general finding that hsp fusion proteins, having fusion partners of widely differing lengths and sequences, elicit CD8 CTL to peptides from the fusion partners, without requiring exogenous adjuvants or the participation of CD4+ T cells.

When mycobacterial hsp fused with large protein fragments, termed fusion partners, are injected into mice in saline solution (PBS) without added adjuvants several of them were previously shown to stimulate the production of CD8 CTL that recognize short peptide epitopes (8-10 amino acids in length) that arose from the fusion partners. The fusion partners varied from about 80 to 110 amino acids in length and were derived from ovalbumin (Suzue, K., et al., *Proc. Natl. Acad. Sci, USA*, 94:13146-13151 (1997)), influenza virus nucleoprotein (Anthony, L., et al., *Vaccine*, 17:373-383 (1999)), and an entire protein subunit of a human papilloma virus (N. R. Chu, personal communication). As described in Example 2, to explore the mechanisms that permit these hsp to be effective with such diverse fusion partners, and that enable the hsp fusion proteins to serve as effective immunogens for CD8 T cells without requiring adjuvants, the immunogenic activities of fusion proteins prepared from the 65 kDa hsp from *Mycobacterium bovis*, BCG strain (here called hsp65) were studied.

The principal fusion partner used in Example 2 was a polypeptide that contains an octapeptide sequence, SIYRYYGL (SEQ ID NO: 1) (hereafter called SYRGL, Udaka, K., et al., *Cell*, 69:989-998 (1992)), which together with $K^b$ serves as a potent stimulator of CD8 T cells having the TCR of a CTL clone called 2C (Kranz, D., et al., *Proc. Natl. Acad. Sci. USA*, 81:573-577 (1984)). This peptide was identified in a synthetic peptide library and, so far as is known, does not occur in nature. The use of various T cells that express the 2C TCR, particularly naive 2C T cells (Cho, B., et al., *Proc. Natl. Acad. Sci. USA*, 96:2976-2981 (1999)), were relied on as specific probes to obtain evidence that i) dendritic cells are more effective than macrophages in presenting the processed hsp fusion protein to naive CD8 T cells, ii) dendritic cells are stimulated directly by each of several hsp65 fusion proteins tested, but not by "native" hsp65 itself, to increase surface expression of MHC class I and II and costimulatory (B7.2) molecules, and iii) CD4 T cells are not required for the fusion protein's ability to elicit production of CD8 CTL in vivo. Taken together, the results described herein indicate that diverse soluble heat shock fusion proteins, regardless of the length or sequence of the fusion partners, stimulate CD8 T cell responses to peptides derived from the fusion partners without requiring exogenous adjuvants. The findings are of particular interest in view of the need to develop protective vaccines against intracellular pathogens for which current immunization strategies are inadequate (e.g., against HIV-1, human papilloma virus, various herpes viruses, malaria).

EXEMPLIFICATION

EXAMPLE 1

In Vivo CTL Elicitation by hsp70 Fusion Proteins Maps to a Discrete Domain and is CD4+ T Cell-Independent Materials and Methods Expression Vectors:

All constructs used to produce OVA.hsp70 fusion proteins were made in the bacterial expression plasmid pKS11h (Suzue, K., et al., *Proc. Natl. Acad. Sci. USA*, 94:13146-13151 (1997)). Fusion constructs, consisting of OVA fused to the N-terminus of various segments of hsp70, were inserted downstream of the histidine tag sequence. A portion of ovalbumin (amino acid 230-359, hereafter referred to as OVA) was amplified from pOV230 (McReynolds, L. A., et al., *Gene*, 2:217-231 (1977)) by PCR using upstream primer oQH025 and the downstream primer oQH027. Functional and structural domains of TBhsp70 based on crystal structures of ATP domain of bovine hsc70 (Flaherty, K. M., et al., *Nature*, 346:623-628 (1990)) and peptide-binding domain of *E. coli* DnaK (Zhu, X., et al., *Science*, 272:1606-1614 (1996)) were used. The full-length TBhsp70 were separated into four segments I, II, III and IV. The full-length TBhsp70 and each segment were fused to C-terminal of OVA to make OVA.TBhsp70 fusion proteins. (The sequences of these and other PCR primers are listed at the end of the Methods and Materials section).

The OVA expression vector pQH07 was constructed by subdloning OVA into the NdeI and NheI sites of pKS11h. Full-length TBhsp70 and four truncated TBhsp70 segments I (aa 1-166), II (aa 161-370), III (aa 360-517) and IV (aa 510-625) were amplified from plasmid pY3111/8 (kind gift of W. Wu, StressGen Biotechnologies, Vancouver Canada). The upstream primer for full-length TBhsp70 and segment I is oQH001, and the downstream primers are oJR061 and oQH011, respectively. The upstream primers for TBhsp70 II, III and IV are oQH012, oQH014 and oQH106, respectively. The downstream primers are oQH013, oQH015 and oJR061, respectively. The plasmids pQH06, pQH08, pQH09, pQH10 and pQH11, which express OVA fused to TBhsp70, TBhsp70 segment I, segment II, segment III and segment IV respectively, were constructed by subdloning the full-length and truncated TBhsp70 PCR products into the BamHI and EcoRI sites of pQH07 (at the C-terminus of OVA). Murine hsp70.1 coding sequence (referred to here as mhsp70) was amplified from plasmid pmhsp70.1 by PCR using the upstream primer oJR102 and the downstream primer oJR103. Plasmid pQH12, expressing OVA.mhsp70 fusion protein, was created by subcloning mhsp70 into the BamHI and EcoRI sites of pQH07. All plasmids were verified by sequencing in both directions with double-stranded DNA templates.

Recombinant Protein Purification:

OVA, OVA.TBhsp70, OVA.TBhsp70 II, OVA.TBhsp70 III, and OVA.TBhsp70 IV were induced in *E. coli* (BL21 (DE3)pLysS) for 9 hours at 25° in the presence of 0.5-1 mM isopropyl thiogalactoside (IPTG) and were purified as soluble proteins. The mycobacterial segment I and murine hsp70 fusion proteins were induced in *E. coli* for 4 hours at 37° with 1 mM IPTG and purified from inclusion bodies and then refolded as previously described (Suzue, K., et al., *Proc. Natl. Acad. Sci. USA*, 94:13146-13151 (1997) and Suzue, K. and Young, R. A., *J. Immunol.*, 156:873-876 (1996)). All proteins were purified using nitrilo-triacetic acid Ni+ column (Qiagen, Hilden Germany) and HiTrap-Q anion exchange chromatography (Pharmacia, Piscataway, N.J.) as previously described (Suzue, K., et al., *Proc. Natl. Acad. Sci. USA*, 94:13146-13151 (1997) and Suzue, K. and Young, R. A., *J. Immunol.*, 156:873-876 (1996)). Purity was assessed using 4-20% gradient SDS-PAGE gels stained with Coomassie Blue (Bio-Rad, Hercules Calif.). All proteins were dialyzed against phosphate-buffered saline (PBS), and sterile filtered at 0.2 µM. Protein concentrations were measured by Lowry assay (Bio-Rad) and expressed in molar terms to allow simple comparison of proteins of differing molecular weights.

Mice and Immunizations:

Six- to eight-week old female C57BL/6, CD4−/− and β2m−/− mice were obtained from the Jackson Laboratory (Bar Harbor, Me.) and Taconic Farms (Germantown, N.Y.). Both knockout mice have C57BL/6 (H-$2^b$) genetic backgrounds. Groups of 3 to 4 mice were injected intraperitoneally (i.p.) with 120 pmoles of recombinant protein in PBS; a second injection was performed subcutaneously (s.c.) two weeks later. The mice were sacrificed 10 days after the boost and splenocytes within groups were pooled (Suzue, K., et al., *Proc. Natl. Acad. Sci. USA*, 94:13146-13151 (1997)).

Cell Line:

EG7-OVA cells were cultured as previously described (Suzue, K., et al., *Proc. Natl. Acad. Sci. USA*, 94:13146-13151 (1997)). OVA-specific CTL elicited by immunization with OVA.TBhsp70 fusion protein without adjuvant were examined. The splenocytes from mice immunized with OVA (Δ) or OVA.TBhsp70 (■) were incubated with irradiated EG7-OVA cells for 6 days in the absence of added cytokines and then used as effector cells (E) in a standard 4 hour cytotoxicity assay. The $^{51}$Cr-labeled target cells (T) were: T2-$K^b$ (dashed line) and T2-$K^b$-pulsed with SIINFEKL peptide (SEQ ID NO: 2) (solid line) at 33 µg/ml. Splenocytes from wild-type C57/BL/6 mice are shown in FIG. 1A; splenocytes from CD4−/− mice are shown in FIG. 1B; and splenocytes from β2m−/− mice are shown in FIG. 1C.

CTL Assays:

CTL assays were performed as described (Suzue, K., et al., *Proc. Natl. Acad. Sci. USA*, 94:13146-13151 (1997)). Splenocyte cultures from mice primed with OVA (Δ), OVA.T-Bhsp70 (■), OVA.TBhsp70 I (□), II (♦), III (X) and IV (+) were used as effector cells in the cytotoxicity assay (See FIG. 4). Results shown are representative of experiments repeated two to five times.

```
PCR primers:
oQH025
(5'-GCAGTACTCATATGATCCTGGAGCTTCCA    (SEQ ID NO: 13)
TTTGCCAGTGGGACAATG-3')

oQH027
(5'-CTCCGACCTCACCTACGACGTTCGCAGAG    (SEQ ID NO: 14)
ACTTCTTAAAATTATCCGATCGCCTAGACCTAG
T-3')

oQH001
(5'-ATAGTACTGGATCCATGGCTCGTGCGGTC    (SEQ ID NO: 15)
GGGATCGACCTCGGG-3')

oJR061
(5'-GGAATTCCTATCTAGTCACTTGCCCTCCC   (SEQ ID NO: 16)
GGCCGTC-3')

oQH011
(5'-GTCGACGAATTCATCATCAGATTCGCTGC    (SEQ ID NO: 17)
TCCTTCTCGCCCTTGTCGAG-3')

oQH012
(5'-GTCGACGGATCCATGGAGAAGGAGCAGCG    (SEQ ID NO: 18)
AATCCTGGTCTTCGACTTG-3')

oQH014
(5'-GTCGACGGATCCATGGTGAAAGACGTTCT    (SEQ ID NO: 19)
GCTGCTTGATGTTACCCCG-3')

oQH016
(5'-GTCGACGGATCCATGCGTAATCAAGCCGA    (SEQ ID NO: 20)
GACATTGGTCTACCAGACG-3')

oQH013
(5'-GTCGACGAATTCATCACGGGGTAACATCA    (SEQ ID NO: 21)
AGCAGCAGAACGTCTTTCAC-3')

oQH015
(5'-GTCGACGAATTCATCAGACCAATGTCTCG    (SEQ ID NO: 22)
GCTTGATTACGAACATCGGC-3')

oJR102
(5'-TCTAGAGGATCCATGGCCAAGAACACGGC    (SEQ ID NO: 23)
GATC-3')

oJR103
(5'-TCTAGAGAATTCCTAATCCACCTCCTCGA    (SEQ ID NO: 24)
TGGTGGGTCC-3')
```

Results and Discussion

Previous studies demonstrated that soluble, adjuvant-free TBhsp70 fusion proteins elicit substantial immune responses, including CD8$^+$ CTLs, in mice (Suzue, K., et al., *Proc. Natl. Acad. Sci. USA*, 94:13146-13151 (1997) and Suzue, K. and Young, R. A., *J. Immunol*, 156:873-876 (1996)). The basis for the effectiveness of hsp70 fusions is unclear as most soluble proteins do not elicit significant CD8$^+$ T cell responses (reviewed in Braciale, T. J., et al., *Immunol. Rev.*, 98:95-114 (1987), Jondal, M., et al., *Immunity*, 5:295-302 (1996)). While there is evidence that the hsp moiety of mycobacterial hsp fusion proteins acts as an effective carrier in the classic sense, enhancing B cell responses to chemically conjugated pneumococcal polysaccharides (Könen-Waisman, S., et al.,*J. Infect. Dis.*, 179:403-413 (1999)) and malarial polypeptide (Barrios, C., et al., *Eur. J. Immunol.*, 22:1365-1372 (1992)), carriers are not known to stimulate CTL production. It was reasonable to expect that hsp70 fusion proteins provide hsp70-specific cognate CD4$^+$ T cell help to OVA-specific CD8$^+$ CTL by activating shared professional antigen presenting cells (APCs) as suggested by many, and demonstrated recently (Bennett, S. R. M., et al., *Nature*, 393:478-480 (1998); Ridge, J. P., et al., *Nature*, 393:474-478 (1998) and Schoenberger, S. P., et al., *Nature*, 393:480-483 (1998)).

As described herein, this cognate help hypothesis was tested using CD4 deficient (knockout) mice (CD4−/−). Wild-type C57BL/6, CD4−/−, and β2m−/− mice were each immunized with OVA or OVA.TBhsp70 fusion protein. As expected, immunization of wild-type mice with OVA.T-Bhsp70, but not OVA, generated CTL specific for the immunodominant epitope of OVA (SIINFEKL) (FIG. 1A). The same results were obtained when the CD4−/− mice were immunized with OVA.TBhsp70 (FIG. 1B). β2m−/− mice, which have very few CD8+ T cells, did not develop OVA-specific CTL after immunization with OVA.TBhsp70 or with OVA alone (FIG. 1C).

Previous efforts to determine whether CD4+ T cell help is necessary for generation of CD8+ CTL have drawn differing conclusions. CD4 knockout mice exhibit a range of CD8+ CTL responses: CD4-dependent, weakly dependent, or independent. CTL responses to minor histocompatibility antigens (Ridge, J. P., et al., *Nature*, 393:474-478 (1998), Guerder, S. and Matzinger, P., *J. Exp. Med.*, 176:553-564 (1992)) or to ovalbumin loaded into spleen cells (Bennett, S. R. M., et al., *J. Exp. Med.*, 186:65-70 (1997)) are CD4-dependent. Some potent CD8+ T cell immunogens including viruses (Bachmann, M. F., et al., *J. Immunol.*, 161:5791-5794 (1988)), such as lymphocytic choriomeningitis virus (Leist, T. P., et al., *J. Immunol.*, 138:2278-2281 (1987); Ahmed, R., et al., *J. Virol.*, 62:2102-2106 (1988); Rahemtulla, A., et al., *Nature*, 353: 180-184 (1991) and von Herrath, M., et al., *J. Virol.*, 70:1072-1079 (1996)), ectromelia virus (Buller, R. M., et al., *Nature*, 328:77-79 (1987)) and some influenza virus subtypes (Wu, Y. and Liu, Y., *Curr. Biol.*, 4:499-505 (1994)), as well as allogeneic cells (Krieger, N. R., et al., *J. Exp. Med.*, 184:2013-2018 (1996)) elicit strong CD8+ T cell responses in wild-type and CD4−/− mice. The similarity of CD8 CTL responses to OVA.TBhsp70 in CD4−/− and wild-type mice suggests that hsp70 fusion proteins are relatively potent CD8+ CTL immunogens. A similar result, showing that CD4+ T cells are not required for the CD8+ CTL response elicited by another mycobacterial heat shock fusion protein (hsp65 fused to a polypeptide containing an epitope for 2C CD8+ T cells) using CD4−/− mice is described in Example 2. In addition, the ability of a non-homologous hsp, gp96, to elicit tumor rejection requires CD4+ T cells at tumor challenge, but not during priming with tumor-derived gp96 (Udono, H. and Srivastava, P. K., *Proc. Natl. Acad. Sci. USA*, 91:3077-3081 (1994)).

It has been proposed that the immunostimulatory effects of certain hsp fusion proteins may be due to the bacterial origin of the hsp moiety (Schild, H., et al., *Curr. Opionon Imm.*, 11: 109-113 (1999)). This possibility was examined by making OVA.hsp70 fusion proteins with the murine homologue of TBhsp70 (Hunt, C. and Calderwood, S., *Gene*, 87:199-204 (1990)), here referred to as mhsp70. Immunization of wild-type C57BL/6 mice with OVA.mhsp70, but not OVA, elicited CTL responses equivalent to those generated by the TBhsp70 fusion protein (FIG. 2A). The response to OVA.mhsp70 was also independent of CD4 (FIG. 2B). Since a CD4+ T cell response to self (murine) hsp70 is unlikely, the effectiveness of the murine hsp70 fusion protein is in accord with the more direct evidence for CD4-independence obtained using CD4−/− mice (see above).

Figure 3:
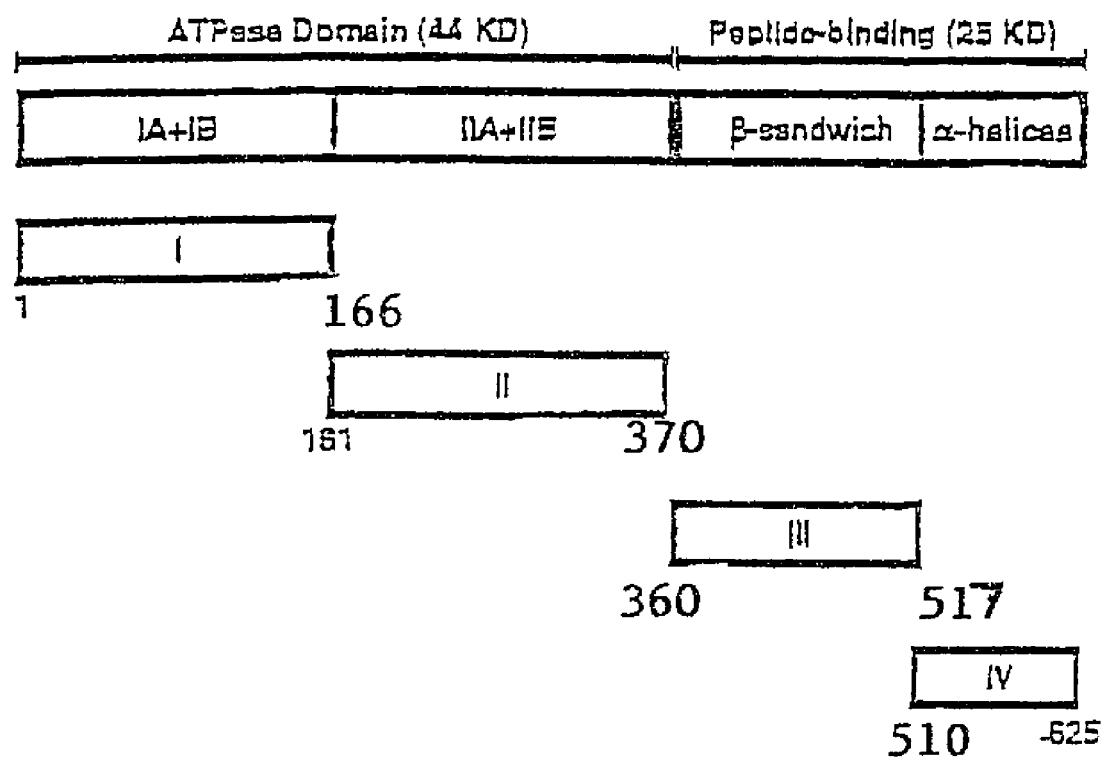
FIG. 3 is an illustration of the domains of the full length TBhsp70 which were separated into four segments I, II, III and IV and fused to C-terminal of OVA to make OVA.T-Bhsp70 fusion proteins; the numbers beneath each segment refer to the amino acid positions in TBhsp70.

The ability of hsp fusion proteins to elicit CTLs against the fusion partner may be a consequence of the hsp moieties' chaperone activity, assuming that this activity is preserved in the fusion protein. To investigate this issue, TBhsp70 was divided into four linear segments and OVA and a glycine/serine linker were fused to the amino-terminus of each segment, creating OVA.TBhsp70 s I-IV (FIG. 3). Each segment corresponds to a distinct structural domain of hsp70 as described by Flaherty, K. M., et al., *Nature*, 346:623-628 (1990) and Zhu, X., et al., *Science*, 272:1606-1614 (1996). As shown in FIG. 3A, the amino-terminal ATP-binding domain was divided into its two structural lobes: I (aa 1-160) and II (aa 161-362). The carboxy-terminal peptide-binding domain was divided into a β-sandwich domain, III (aa 364-512), and an α-helical domain, IV (aa 512-625).

Figure 4:
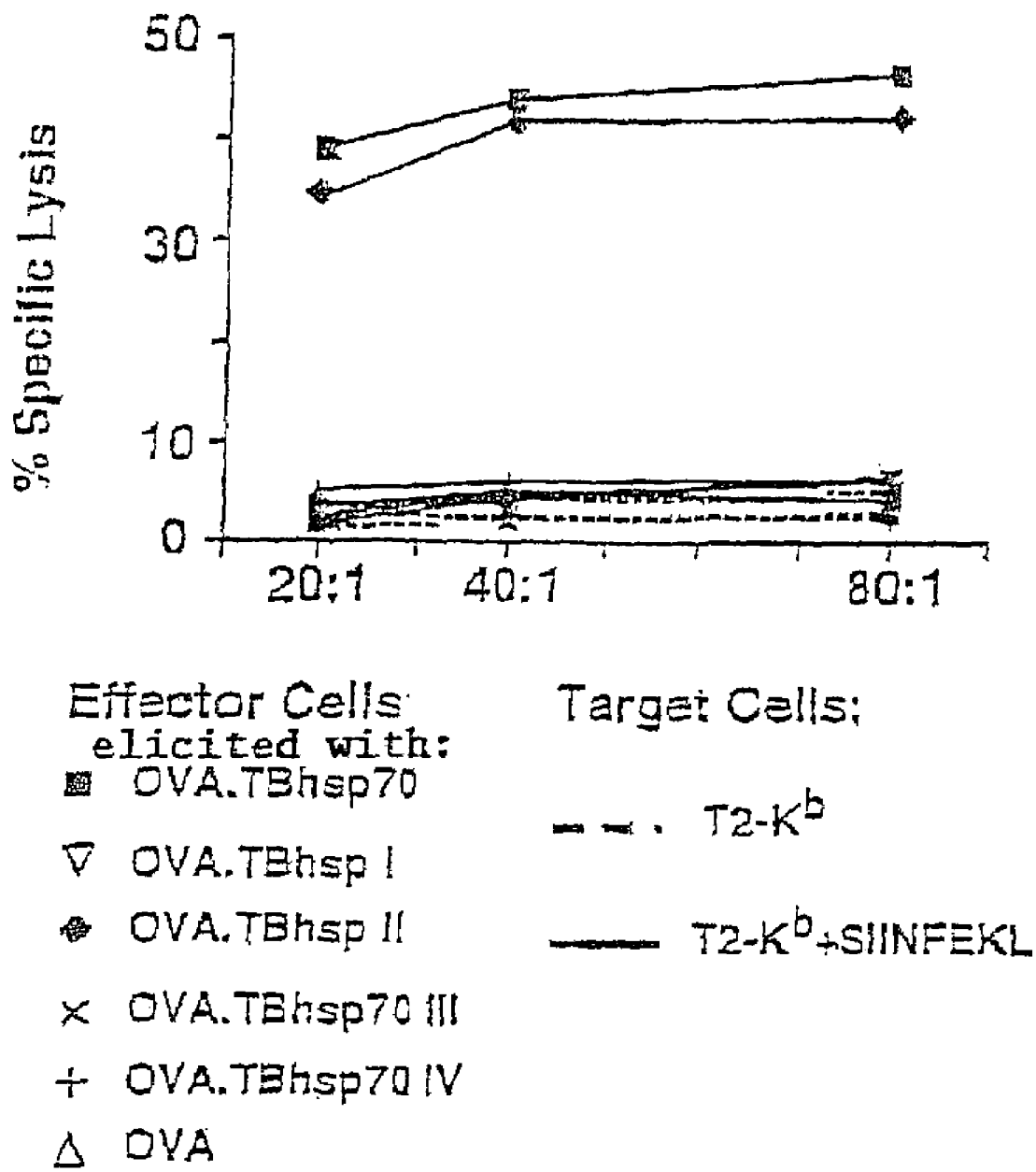
FIG. 4 is a graph of E:T versus % specific lysis illustrating OVA-specific T cell responses in mice immunized with OVA fused to domains of TBhsp70; splenocyte cultures from mice primed with OVA (Δ), OVA.TBhsp70 (■), OVA.TBhsp70 I (∇), II (◆), III (X) and IV (+) were used as effector cells in the cytotoxicity assay.

Six groups of three C57BL/6 mice were immunized with 120 pmoles of OVA, OVA.TBhsp70, and OVA fused to segments I, II, III and IV. CTL assays showed that splenocytes from mice immunized with OVA.TBhsp70 and OVA fused to segment II lysed T2-$K^b$ cells in the presence, but not absence, of the OVA $K^b$ epitope, SIINFEKL (FIG. 4). In contrast, cells from mice immunized with OVA and OVA fused to segments I, III and IV were ineffective, even at an E:T ratio of 80:1. Levels of cytolysis obtained with splenocytes from mice immunized with OVA.TBhsp70 and OVA fused to segment II were indistinguishable (FIG. 4). These results show that half of the ATP-binding domain of TBhsp70 (aa 161-362) is sufficient to stimulate substantial production of anti-OVA CTL response in the absence of adjuvant.

Since it is highly unlikely that segment II preserves chaperone activity we conclude that the ability of the fusion proteins to elicit CD8+ T cell does not depend on the hsp moieties' chaperone properties. The data described herein support a model in which hsp70 bypasses the need for CD4+ help by directly or indirectly activating or affecting the maturation state of APCs such as dendritic cells in a manner similar to some viruses (Ruedl, C., et al., *J. Exp. Med.*, 189:1875-1883 (1999)). According to this model, hsp70 fusion proteins likely activate few CD8+ T cells to release immunostimulatory cytokines in draining lymph nodes. These cytokines, in turn, provide the help required to upregulate expression of costimulatory molecules on APCs in the lymph node, leading to further CD8+ T cell activation (Ruedl, C., et al., *J. Exp. Med.*, 189:1875-1883 (1999)). Recent studies demonstrate that exposure of macrophages to bacterial and human hsp60 (Chen, W., et al., *J. Immunol.*, 162:3212-3210 (1999); Kol, A., et al., *J. Clin. Invest.* 103:571-577 (1990)), murine hsp70 and gp96 (Suto, R. and Srivastava, P. K., *Science*, 269:1585-1588 (1995); Breloer, M., et al., *J. Immunol.*, 162:3141-3147 (1999)) increases expression of adhesion molecules and cytokines.

The ability to hsp70 fusion proteins to elicit CTL responses in the absence of CD4+ cells indicates that hsp70 can be used as a vehicle for the development of prophylaxis and therapy of diseases or conditions characterized by a lack or deficiency of CD4+ cells, such as HIV-1 and its opportunistic infections. Infections by HIV and its simian cousin SIV can lead to a substantial reduction of CD4+ T cells, thereby crippling the host's immune response to HIV and other pathogens. This loss of CD4+ cells is thought to impair the development and maintenance of CD8+ CTL responses (Kalams, S. A., et al., *J. Virol.*, 73:6715-6720 (1999)). Recent studies conclude that strong HIV-specific CTL responses are required to keep HIV-1 infection in check and to destroy HIV-infected cells (Harrer, T., et al., *AIDS Res. Hum. Retro.*, 12:585-592 (1996); Harrer, T., et al., *J. Immunol.*, 156:2616-2623 (1996); Yang, O. O., et al., *J. Virol.*, 70:5799-5806 (1996); Yang, O. O., et al., *J. Virol.*, 71:3120-3128 (1997); Matano, T., et al., *J. Virol.*, 72:164-169 (1998) and Wagner, L., et al., *Nature*, 391:908-911 (1998)).

EXAMPLE 2

Heat Shock Fusion Proteins Stimulate Dendritic Cells and Elicit Production of Cytolytic T Lymphocytes Without Requiring Participation of CD4 T Cells Methods and Materials Mice, CTL Clones and Cell Lines C57BL/6 (H-$2^b$), Cd4-deficient (CD4 tm1Mak, H-$2^b$), and C3H/HeJ mice (H-$2^k$) were obtained from The Jackson Laboratories (Bar Harbor, Me.), maintained in barrier cages under specific pathogen free conditions, and immunized between 4- and 10-weeks of age. 2C TCR transgenic mice (H-2$^b$) contain the rearranged transgenes encoding the αβ TCR from a 2C CTL clone (Sha, W., et al., *Nature*, 335:271-274 (1988)). 2C TCR transgenic mice deficient for the recombination activating gene-1 (termed 2C/RAG) (Manning, T., et al., *J. Immunol.*, 159:4665-4675 (1997)) were used as a source of naive T cells for in vitro assays (Cho, B., et al., *Proc. Natl. Acad. Sci. USA*, 96:2976-2981 (1999)). 2C CTL clone. L3.100, has been previously described (Sykulev, Y., et al., Immunity, 9:475-483 (1998)). EL4 cells were obtained from the ATCC (Rockville, Md.) and T2-K$^b$ cells were a generous gift from Peter Creswell, Yale University.

Plasmids, Peptides, and Proteins

In the P1 polypeptide the sequences flanking the—and C-termini of the SYRGL octapeptide (FIG. 5A), from ovalbumin (ova251-257) and α-ketoglutaraldehyde dehydrogenase, respectively, were modified by addition of a lysine residue penultimate to the N-terminus (out of ubiquitination consideration) (Eisenlohr, L., et al., *J. Exp. Med.*, 175:481-487 (1992); York, I. A. and Rock, K. L., *Annu. Rev. Immunol.*, 14:369-396 (1996)), and an isoleucine and a tyrosine residue were added at the—and C-termini for cloning purposes. Complementary oligonucleotides encoding P1 were synthesized and cloned into a mammalian expression vector VR1055 (Vical, San Diego, Calif.), and subsequently subcloned as an in-frame fusion at the 3' end of *M. bovis* BCG hsp65 gene (hsp65-P1) into the bacterial expression vector pET28A+ (Novagen, Madison, Wis.). The P1 sequence was also subcloned into the 3' end of the gene encoding *E. coli* maltose binding protein in pMAL-p2, using the pMAL protein fusion system (New England Biolabs, Beverly, Mass.), as well as into the mammalian expression vector pClneo (Promega, Madison, Wis.). All hsp65 fusion proteins used in this example, as well as the unmodified hsp65, were produced as recombinant proteins in *E coli*. They were purified under denaturing conditions from the soluble fraction of bacterial lysates and fractionated successively on butyl-Sepharose, Q-Sepharose (and Ni-Sepharose when applicable), and finally by dialysis against PBS. Ma1-P1 was purified by amylose affinity chromatography (New England Biolabs, Beverly, Mass.).

SDS-PAGE analysis of purified hsp65-P1 revealed a major species at 67.5 kDa, which was shown to be hsp65-P1 by Western analysis, using anti-mycobacterial hsp65 specific antibody (StressGen, Victoria, Canada), and by electrospray mass spectrometry (M.I.T. Biopolymer Laboratory). Ma1-P1 was also subjected to amino acid analysis and SDS-PAGE to confirm molecular weight (48.1 kDa) and purity. P1 and SYRGL peptides were synthesized by the MIT Biopolymers Laboratory. Protein concentrations were estimated by bicinchoninic acid or amino acid analyses and were expressed in molar terms to facilitate comparisons between proteins and polypeptides of differing molecular masses. Endotoxin concentrations of recombinant protein preparations were determined by the Limulus assay, using reagents and conditions according to Associates of Cape Cod (Falmouth, Mass.). Peptide concentrations were estimated by W/V or based on amino acid analyses.

Antibodies and Flow Cytometry

Flow Cytometry was carried out on a FACSCaliber, using CellQuest software (Becton Dickinson, Franklin Lakes, N.J.). Unlabeled or FITC-, PE-, allophycocyanin- or biotin-labeled antibodies against CD69, CD4, CD8, CD11c, CD11b, GR.1, B7.2, B220 or MCH class I (H-2$^b$), as well as secondary antibodies and streptavidin labeled with allophycocyanin, or PE, were obtained from Pharmingen (San Diego, Calif.). 1B2, a clonotypic antibody that recognized 2C TCR (Kranz, D., et al., *Proc. Natl. Acad. Sci. USA*, 81:573-577 (1984)), was purified from the 1B2 hybridoma and biotinylated using biotinamidocaproate N-hydroxysuccinimide ester (Sigma, St. Louis, Mo.). The antibody, Y3, is cross-reactive with MCH class I from H-2$^b$ (K$^b$) and H-2$^k$ haplotypes. It is affinity purified from culture supernatants from the Y3 hybridoma (obtained from ATCC, Rockville, Md.) and labeled with fluorescein using fluorescein isothiocyanate.

Generation of Bone-marrow Derived Dendritic Cells and Isolation of Antigen Presenting Cells and Naive 2C T Cells To generate bone-marrow derived dendritic cells from C57BL/6 (or C3H) mice, bone marrow was flushed from the femur and tibia, red blood cells were lysed, and the remaining cells were cultured at 10$^6$ cells/ml in RPMI 1640 medium (supplemented with 10% heat-inactivated fetal calf serum, 2 mM L-glutamine, 10 mM HEPES, 50 μm β-mercaptoethanol, 100 U/ml penicillin and 100 μg/ml streptomycin) containing 20 ng/ml murine GM-CSF (R&D Systems, Minneapolis, Minn.). The medium was replaced on days 2 and 4, and on day 6 the cells (immature dendritic cells) were harvested for use.

In vitro assays were performed with purified cell populations unless otherwise noted. Magnetic cell sorting (MACS) was carried out according to the manufacturer's instructions (Miltenyi Biotec. Auburn, Calif.). Dendritic cells (splenic or bone marrow-derived) were isolated by positive sorting using anti-CD11c antibody (purity ranged from 70-97%). Peritoneal lavage macrophages were purified by treating them with biotinylated antibodies specific for CD11c, GR.1, and B220, followed by washing and incubating them with magnetic microbeads coated with anti-CD4 or anti-CD8 antibodies or with streptavidin and then passing them over a negative sorting column. Macrophage purity was typically >90%. For purification of 2C T cells from 2C/RAG transgenic mice, lymph node and spleen cells were coated with anti-CD8 magnetic beads (an average of 2 beads per cell) and positively sorted as above (purity >93%). The purification procedures did not activate APC or T cells as shown by flow cytometry: APC showed no increase in B7.2, MHC class I, or cell diameter, and T cells showed no CD69 upregulation after 24 hr in culture. There was also no significant $^3$H-thymidine incorporation by T cells after 48 hr incubation.

Cytolytic T Cell Assays

Unless otherwise noted, $^{51}$Cr-labeled T2-K$^b$ cells were used as target cells. They were incubated with effector cells derived from either fusion protein-injected mice or from cultured 2C T cell clones for 4 hr in the presence or absence of SYRGL (1 μM). Specific lysis was calculated as follows: [(experimental counts−spontaneous counts)/(total counts−spontaneous counts)]×100.

To assess the ability of various APC to process hsp65-P1, dendritic cells and macrophages were used as target cells. Each of these cell populations was purified by MACS and then $^{51}$Cr-labeled for 1 hr at 37° C. The labeled cells were then incubated with hsp65-P1 together with the 2C CTL clone (L3.100) at a CTL: target cell (E:T) ration of 5:1. Assays were performed in triplicate using 96-well round bottom plates and cell supernatants were counted in a γ spectrometer after 4 hr. Specific lysis was calculated as above.

Transient Transfection and Antigen Processing Assays

EL4 cells (5×10$^6$) were electroporated with 15 μg of the parent plasmids or plasmids containing the genes for P1 (in VR1055) or hsp65-P1 (in pClneo). 48 hr after transfection, the cells were subjected to centrifugation in Ficoll-Paque (Pharmacia Biotech., Piscataway, N.J.) (2200rpm, 20 min) and $10^6$ live cells were incubated with an equal number of splenocytes from naive 2C/RAG mice. After 18 hr the cells were stained with 1B2, anti-CD69, and anti-CD8 antibodies (labeled with FITC, PE, and allophycocyanin, respectively) and 2C T cells were evaluated for upregulation of CD69 by flow cytometry, gating on propidium iodide-negative, $1B2^+$, $CD8^+$ cells.

Naive 2C T Cell Responses to Dendritic Cells and Macrophages and Dendritic Cell Activation Assays Purified dendritic cells and macrophages were incubated with various concentrations of proteins or peptides in 96-well ($5 \times 10^4$ cells/well) flat bottom plates for 24 hr at 37° C. The following day an equal number of purified naive 2C T cells were added to each well (final volume: 200 µl for the 96-well plates, 600 µl for the 48-well plates). After 18 hr., the 48-well plates were separated into i) cell pellets to analyze 2C T cells for expression of the acute activation marker CD69 by flow cytometry, gating on propidium iodide-negative. $1B2^+ CD8^+$ cells, and ii) cell supernatants to measure IL-2 secretion (in triplicate, using HT2 cells in a standard bioassay) (Watson, J., *J. Exp. Med.*, 150:1510-1519 (1979)). After 48 hr, the 96-well plates were assayed for IFN-γ secretion (using 50 µl of cell supernatants and a capture ELISA assay (R&D Systems, Minneapolis, Minn.), and for T cell proliferation (1 mCi $^3$H-thymidine (NEN, Boston, Mass.) was added per well and 16 hr later the cells were harvested to measure $^3$H-thymidine-incorporation). Where indicated, 1B2 Fab fragments were added to naive 2C T cells at a final concentration of 25 µg/ml.

Immature bone marrow-derived dendritic cells (day 6 of culture) were purified by magnetic sorting (>95% $CD11b^+$ $CD11c^+$) and incubated ($2.5 \times 10^5$ cells/well in 96-well round bottomed plates) with various fusion proteins or control proteins. The following day, cells were analyzed by flow cytometry for expression of B7.2 and MHC class I and class II molecules, gating on propidium iodide-negative, $CD11c^+$ cells.

Results

Design and Characterization of Heat Shock Fusion Protein hsp65-P1

Figure 5A:
FIG. 5A illustrates the P1 peptide amino acid sequence (SEQ ID NO: 25), aligned over a diagram of the hsp65-P1 fusion protein (P1 is shown at the C-terminal of hsp65). When liberated from P1, SIYRYYGL (SEQ ID NO: 1) (demarked by arrows) binds to $K^b$ to form the peptide-MHC complex recognized by the 2C TCR. In P1, SIYRYYGL (SEQ ID NO: 1) is flanked 5' and 3' by sequences that lie immediately upstream and downstream, respectively, of peptide bonds that are cleaved (see arrows) in murine cells to liberate naturally occurring peptides (SIINFEKL (SEQ ID NO: 2) from ovalbumin (Ova) and LSPFPFDL (SEQ ID NO: 3) from α-ketoglutaraldehyde dehydrogenase (αKG) (Falk, K., et al., *Eur. J. Immunol.*, 22:1323-1326 (1992); Ukada, K., et al., *J. Immunol.*, 157:670-678 (1996)).
Figure 5B:
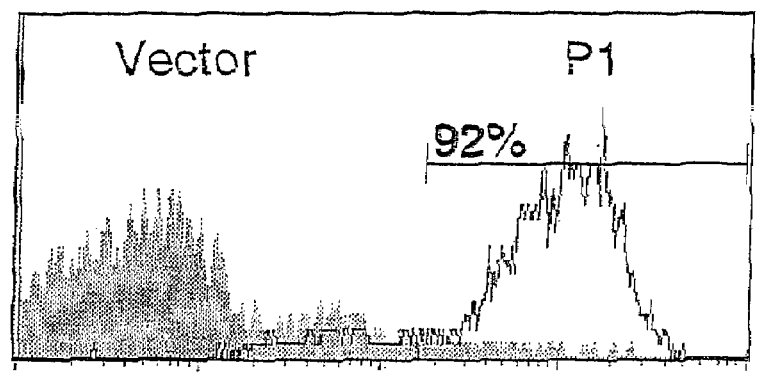
FIG. 5B is pair of histograms, which display experimental evidence that P1 and hsp65-P1 are processed intracellularly to yield the SYRGL octapeptide. 48 hr after transfection with mammalian expression vectors (VR1055 and pCINeo), containing sequences that encode P1 and hsp65-P1, respectively, EL4 cells were incubated for 18 hr with an equal number of naive 2C T cells. Histograms show the percentage of live, $2C^+CD8^+$ cells that were stimulated to upregulate the activation marker CD69. The responses of these naive T cells to control EL4 cells, transfected with the empty (vector) plasmids, are shown as shaded histograms.
Figure 5C:
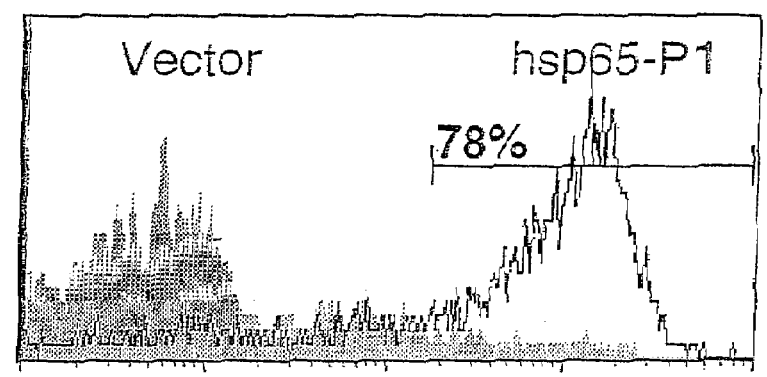
FIG. 5C is a graph which displays experimental evidence that normal C57BL/6 mice have T cells that can recognize the SYRGL-$K^b$ complex. A $CD8^+$ T cell line, derived from C57BL/6 mice immunized with the SYRGL peptide in adjuvant, specifically lysed T2-$K^b$ target cells in a peptide-dependent manner. A highly cytolytic long-term cultured 2C CTL clone (L3.100) is shown for comparison.

As shown in FIGS. 5A and 5B, the principal fusion protein used herein contains the polypeptide P1 fused to the C-terminus of hsp65. P1 includes the octapeptide, SYRGL, that behaves, in association with $K^b$, as a strong agonist for the TCR on 2C T cells (Sykulev, Y., et al., *Immunity*, 4:565-571 (1996)). The sequences that flank the octapeptide in P1 were chosen because they correspond to those known to be effectively cleaved intracellularly in two unrelated proteins: ovalbumin (Falk, K., et al., *Eur. J. Immunol.*, 22:1323-1326 (1992)) and α-ketoglutaraldehyde dehydrogenase (Udaka, K., et al., *Cell*, 69:989-998 (1992), see arrows, FIG. 5A). To determine if the P1 polypeptide, alone or linked as a fusion partner to hsp65, could be cleaved intracellularly to liberate the SYRGL octapeptide, we transfected plasmids containing sequences for P1 or hsp65-P1 were transfected into EL4 cells ($H-2^b$). Because relatively few of the transiently transfected cells were expected to express P1 or hsp65-P1, the transected cell population was not used in cytolytic assays as targets for 2C CTL. Instead, their ability to stimulate naive 2C T cells were examined. As shown in FIG. 5C, 80-90% of these naive T cells were stimulated to express the acute activation marker CD69 in response to EL4 cells transfected with either the P1 or hsp65-P1 plasmids, while virtually none of the naive T cells were activated by cells transfected with the empty plasmids (vector, shaded histograms, FIG. 5C). These results indicate that in these transfected cells P1 and hsp65-P1 can be cleaved to release the octapeptide, which is then presented by $K^b$.

C57BL/6 mice produce SYRGL-specific $CD8^+$ cytolytic T cells in response to hsp65-P1

Before immunizing mice with hsp65-P1, it was first ensured that CD8 T cells that can recognize the SYRGL octapeptide are present in normal C57BL/6 ($H-2^b$) mice. The mice were therefore injected with SYRGL peptide in adjuvant (TiterMaxGold), their spleen cells were maintained in culture for several weeks (see Methods) and subsequently tested in a standard cytotoxicity assay. As shown in FIG. 5D, the cell line's lysis of $K^{b+}$ target cells ($T2-K^b$) was SYRGL dependent, indicating the presence in these mice of T cells that can respond to $SYRGL-K^b$ complexes.

Figure 6A:
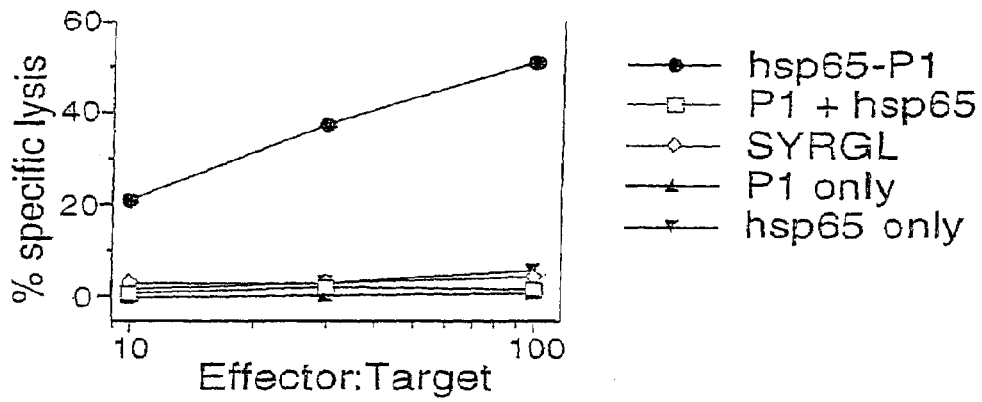
FIG. 6A is a graph showing $CD8^+$ CTL that recognize the SYRGL-$K^b$ complex are produced in C57BL/6 mice injected with hsp65-P1 in PBS but not in those injected similarly with equimolar amounts of various controls (a mixture of P1 and hsp65, the SYRGL octapeptide, the P1 polypeptide itself, or hsp65 itself; as noted further below, SYRGL is referred to as an "octapeptide" as it is an abbreviation of thesequence SIYRYYGL (SEQ ID NO.: 1)).
Figure 6B:
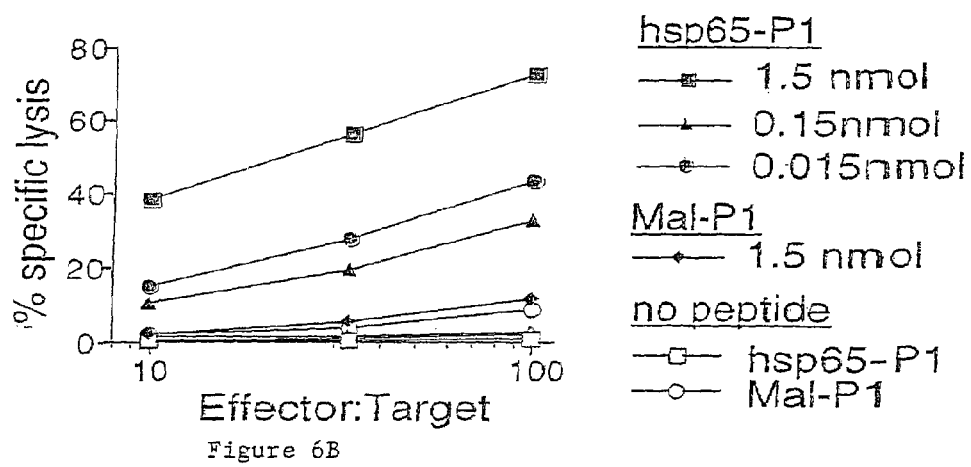
FIG. 6B is a graph illustrating the production of SYRGL-specific CTL in mice injected with various amounts of hsp65-P1, 0.015-1.5 nmoles (1-100 μg) or a control fusion protein in which P1 is linked to the C-terminus of a maltose-binding protein (Mal-P1, 80 μg); lysis of T2-$K^b$ target cells in the absence of added SYRGL peptide is indicated by unfilled symbols.
Figure 6C:
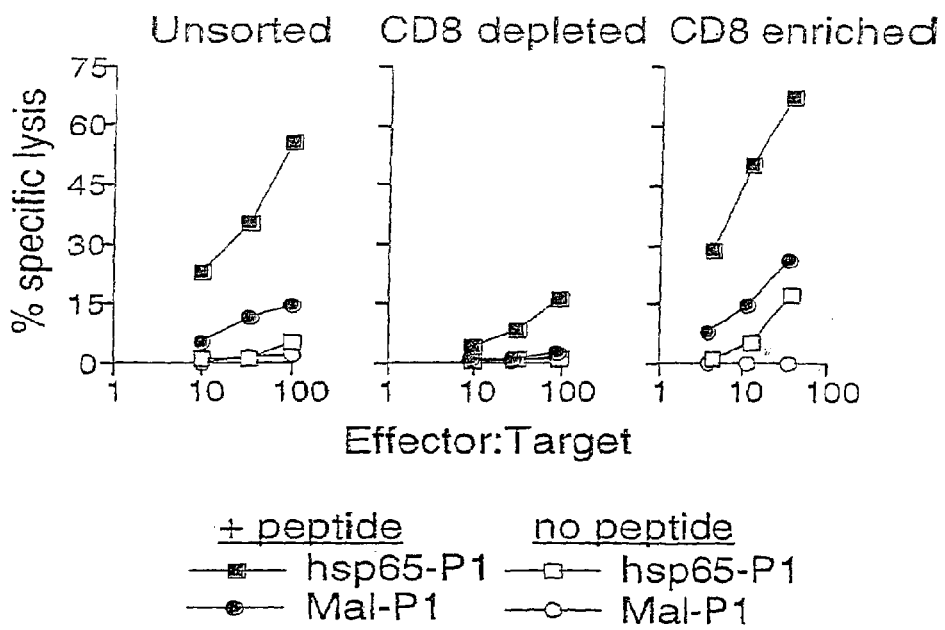
FIG. 6C are graphs showing depletion of $CD8^+$ T cells eliminates the SYRGL-specific CTL produced by mice injected with hsp65-P1. Lymph node and spleen cells from C57B1/6 mice immunized with 1.5 nmoles of hsp65-P1 or Mal-P1 were cultured for 6 days and then depleted of CD8 T cells by magnetic sorting. The untreated, CD8-depleted, and CD8-enriched populations (30%, 1%, 90%, $CD8^+$ T cells respectively) were analyzed in a 4 hr cytolytic assay; lysis of T2-$K^b$ target cells in the absence of added SYRGL peptide is indicated by unfilled symbols.

To determine if the hsp65-P1 fusion protein could stimulate ("prime") anti-SYGRL CTL in vivo, normal C57BL/6 mice were injected subcutaneously (s.c.) with the fusion protein in saline without added adjuvants. Each mouse received two injections, one wk apart. 7 days after the $2^{nd}$ injection cells from regional lymph nodes and spleen were restimulated in culture with SYRGL (1 µM) in the absence of exogenous cytokines, and tested after 6 days for CTL activity in a 4 hr cytolytic assay, using $^{51}$-Cr labeled $K^{b+}$ target cells ($T2-K^b$; see Methods). Of 40 injected mice, 35 produced CTL whose lysis of the $K^{b+}$ target cells was SYRGL-dependent (see FIG. 6A for a representative response). C57BL/6 mice treated in exactly the same way with equimolar amounts of various controls (hsp65, P1, or a mixture of hsp65 and P1, or SYRGL alone), all failed to yield SYRGL-specific CTL (FIG. 6A). As little as 1 µg (0.015 nmoles) of hsp65-P1 could elicit an anti-SYRGL CTL response. A control fusion protein, made by fusing the P1 sequence to the C-terminus of another bacterial protein chosen simply for ease of purification (the *E. coli* maltose binding protein), here called Mal-P1, was around 10-100 times less effective in these assays (FIG. 6B) and without any detectable effect in others (FIGS. 7, 8A-8C, 9A-9C, 10A-10C). Removal of CD8 T cells by magnetic sorting showed that the cytolytic response to hsp65-P1 was due to CD8 T cells (FIG. 6C). These results demonstrate that hsp65-P1, without added adjuvants, can elicit a CD8 T cell response to the fusion partner.

Dendritic Cells and Macrophages Differ in Ability to Serve as Antigen-presenting Cells for hsp65-P1

Figure 7:
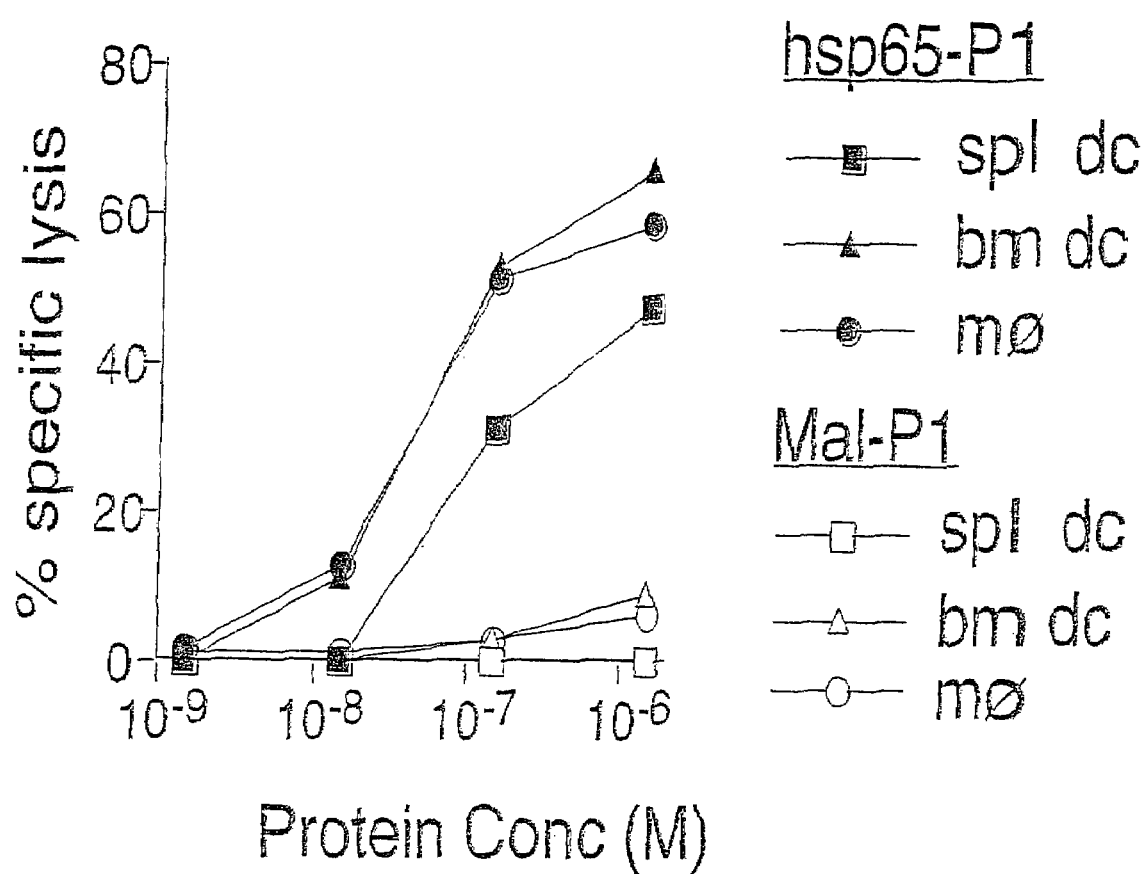
FIG. 7 is a graph showing $^{51}$Cr-labeled splenic dendritic cells (sp1 dc), bone-marrow derived dendritic cells (bm-dc), or purified macrophages (mø), isolated from peritoneal lavage, all from B6 (H-$2^b$) mice were incubated for 4 hr with a 2C CTL clone (L3.100: see FIG. 5D) and various concentrations of the SYRGL octapeptide. CTL target cell ratio (E:T)=5:1. Unfilled symbols show lysis when the control fusion protein (Mal-P1) was used in place of hsp65-P1.

To identify antigen presenting cells (APC) that mediate in vivo CD8 T cell responses, purified preparations of APC from C57BL/6 mice (dendritic cells from spleen or bone marrow, and macrophages from peritoneal lavage) were tested for ability to present processed hsp65-P1 and serve as target cells in cytolytic assays, using a well-established $SYRGL-K^b$ specific CTL clone (L3.100) as effectors. When dendritic cells and macrophages were $^{51}$Cr-labelled and incubated with hsp65-P1 for 4 hr, they were lysed effectively and to about the same extent (FIG. 7). No significant lysis was observed, however, when the control fusion protein Mal-P1 was used in place of hsp65-P1, suggesting that processing of hsp65-P1 by these APC was not due to indiscriminate extracellular proteolysis.

Figure 8A:
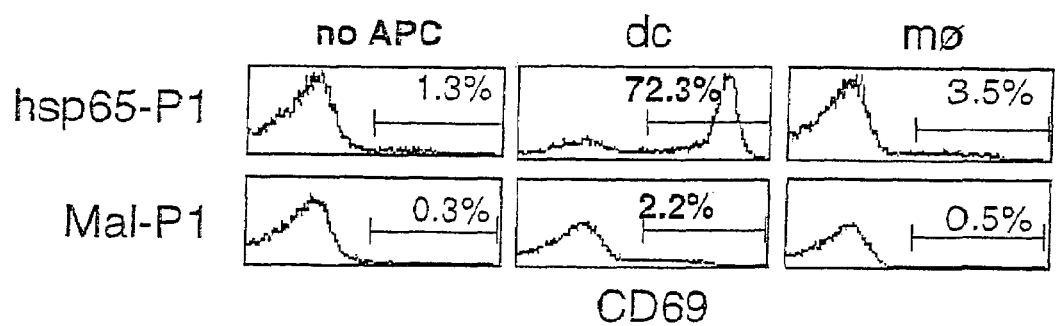
FIG. 8A illustrates that splenic dendritic cells and peritoneal lavage macrophages were purified by magnetic sorting and incubated for 18-24 hr with equimolar concentrations of hsp65-P1 or Mal-P1 before adding naive 2C T cells. Expression of the activation marker CD69, Hsp65-P1 or Mal-P1 were added to purified splenic dendritic cells, macrophages, or to media alone ("no APC") at 15 nM (~1 μg/ml). After 24 hr, purified naive 2C T cells were added (T cell:APC ratio of 1:1), and 18 hr later cells were analyzed for CD69, gating on propidium iodide-negative $2C^+CD8^+$ cells. The percentage of 2C T cells with increased expression of $CD69^+$ is indicated.
Figure 8B:
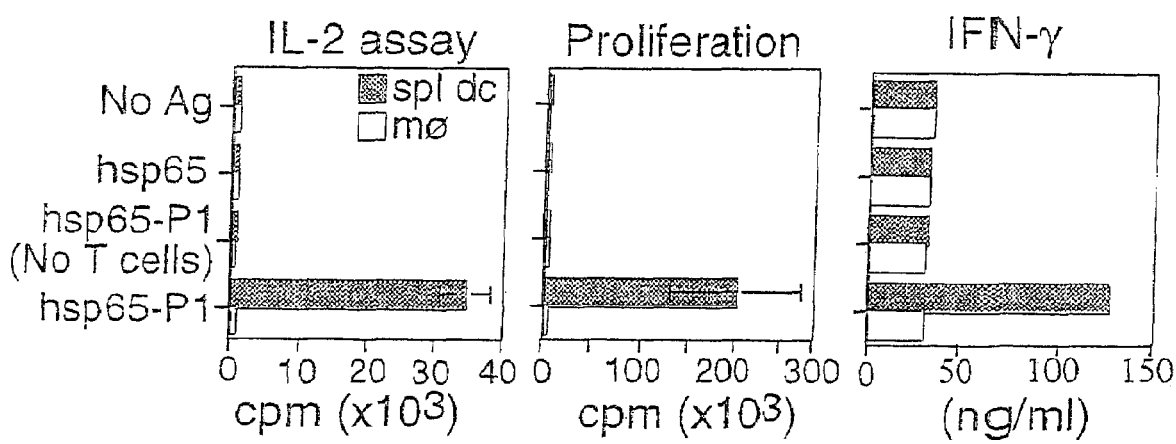
FIG. 8B illustrates that splenic dendritic cells and peritoneal lavage macrophages were purified by magnetic sorting and incubated for 18-24 hr with equimolar concentrations of hsp65-P1 or unmodified hsp65 before adding naive 2C T cells. Dendritic cells or macrophages were incubated with hsp65-P1 or hsp65 before adding the naive 2C T cells and incubation was continued for an additional 18 hr (IL-2 assay) or 60 hr (proliferation assay) or 48 hr (IFN-γ assay). "No Ag" means the dendritic cells and 2C T cells were present but hsp65-P1 and hsp65 were absent: "No T" cells means the hsp65-P1 was present but the 2C T cells were omitted.
Figure 8C:
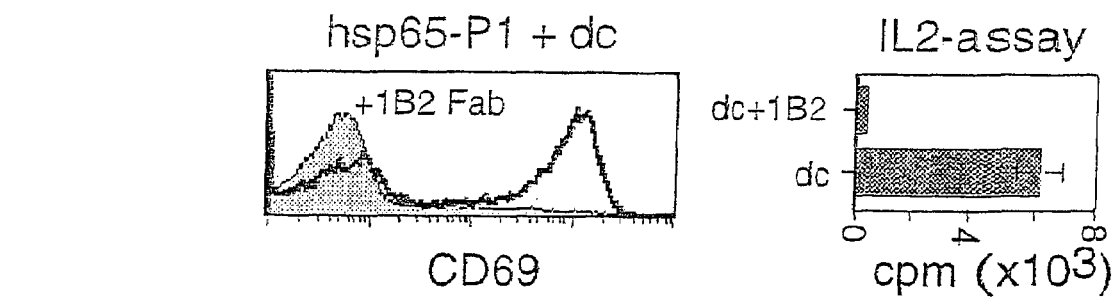
FIG. 8C is a graph illustrating inhibition of responses by a clonotypic monoclonal antibody to the 2C TCR (1B2). Bone marrow derived dendritic cells were incubated with 10 μg/ml hsp65-P1 overnight. Equal numbers of naive 2C T cells were then added in the presence or absence of 1B2 Fab fragments (25 μg/ml). After an additional 18 hr, cells and supernatants were analyzed, respectively, for CD69 expression (left panel) and IL-2 production (3H-thymidine incorporation by IL-2-responsive HT2 cells, right panel).

Cytolytic reactions with potent CTL clones, such as L3.100, can be exquisitely sensitive, detecting very few and probably as little as one cognate peptide-MHC complex per target cell, (Sykulev, Y., et al., *Immunity*, 4:565-571 (1996)). Therefore, a more discriminating assay in which dendritic cells and macrophages that had been incubated with hsp65-P1 were compared as APC for their ability to stimulate naive 2C T cells was used. As shown in FIG. 8A-8C, when the dendritic cells were incubated with hsp65-P1 overnight and then with naive 2C T cells, the naive T cells were stimulated to: i) express CD69, ii) proliferate, and iii) secrete IL-2 and IFN-γ. In contrast, the macrophage preparations stimulated none of these responses. (It may be that activated macrophages would have behaved differently, but we deliberately focused on non-activated macrophages and dendritic cells to stimulate conditions in the immunized animal were deliberately focused upon. The response elicited by dendritic cells could be inhibited by the clonotypic, anti-2C TCR, antibody (1B2; FIG. 8C), indicating that they were mediated by ligation of the 2C TCR. The requirement for the hsp65 moiety in the hsp65-P1 fusion protein is emphasized by the result that naive 2C T cells were stimulated to express CD69 by dendritic cells that had been incubated with hsp65-P1 but not by those that had been incubated with the control fusion protein Ma1-P1 (FIG. 8A).

Incubation of dendritic cells with various controls (P1 alone, hsp65 alone, or a mixture of hsp65+P1) in place of hsp65-P1 did not stimulate 2C T cells to secrete IFN-γ. However, of all the controls the P1 peptide was exceptional in that it exhibited some activity; with both dendritic cells and macrophages it stimulated CD69 expression and with dendritic cells, but not with macrophages, it induced proliferation and IL-2 secretion by the naive 2C T cells. It is likely that the P1 peptide itself is subject to proteolysis by these APC, particularly by dendritic cells, but whether extracellularly or in some intracellular compartment is not clear. Whatever the explanation, it should be noted that the P1 polypeptide did not stimulate CD8 CTL production in vivo under conditions where the hsp65-P1 fusion protein was consistently effective (FIG. 6A). In addition, as is shown later, P1 also failed to activate dendritic cells (see FIGS. 10A-10C).

Figure 9A:
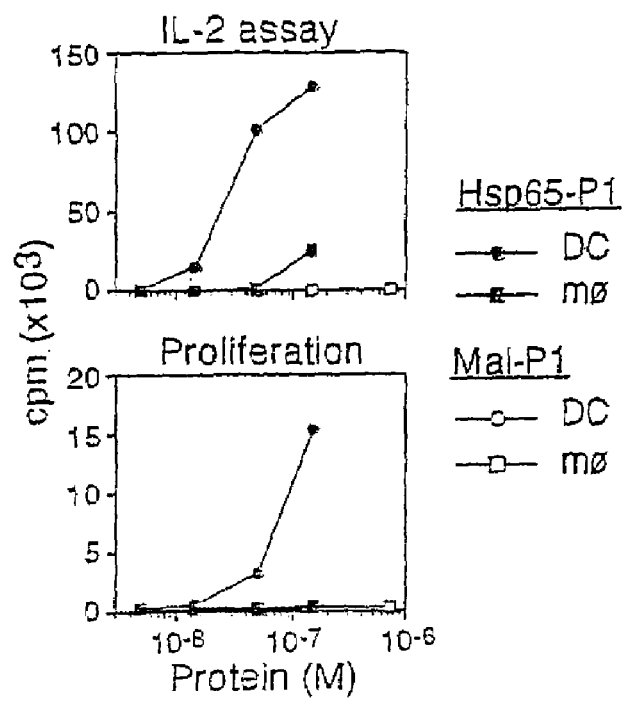
FIG. 9A is a pair of graphs comparing dendritic cells' and macrophages' ability to stimulate T cell responses at limiting antigen dose in vitro. Fresh splenic dendritic cells or macrophages were incubated with various concentrations of hsp65-P1 or Mal-P1 fusion proteins for about 18 hr before adding purified naive 2C T cells (see FIGS. 8A, 8B). Supernatants were sampled 18 hr later to determine IL-2 levels (upper panel). $^3$H-thymidine was added at 48 hr and cells were harvested after an additional 18 hr to assess T cell proliferation (lower panel).

To examine the difference between dendritic cells and macrophages more closely, these cells were incubated with various concentrations of the fusion proteins and then evaluated their ability to stimulate naive 2C T cells. As shown in FIG. 9A, the naive cells proliferated and produced substantial amounts of IL-2 in response to dendritic cells that had been incubated with concentrations of hsp65-P1 in the 0.1-0.01 μM range. In contrast, the responses by naive cells were negligible when macrophages were used in place of dendritic cells or when the Ma1-P1 control fusion protein was used at concentrations up to 1 μM (FIG. 9A). Togther, these data suggest that dendritic cells are more effective than macrophages in processing and presenting the octapeptide from hsp65-P1.

Heat Shock Fusion Proteins Stimulate Dendritic Cells Directly

The distinctive ability of hsp65-P1 to stimulate naive 2C (anti-SYRGL) T cells in vitro only in the presence of dendritic cells led to the examination of the effect of hsp65-P1 on dendritic cells directly. As shown in FIG. 10A, when immature bone-marrow derived dendritic cells (day 6 in culture) were incubated overnight with various concentrations of hsp65-P1 the dendritic cell surface level of an MHC class I molecule ($K^b$) was increased. The extent of the increase depended on the hsp65-P1 concentration, and no increase was seen when hsp65-P1 was replaced by a series of control proteins and peptides (hsp65 alone, P1 alone, SYRGL, Ma1-P1, or a monoclonal IgG antibody [anti-2,4,6, trinitrophenyl]).

Other hsp65 fusion proteins, having various fusion partners (influenza virus nucleoprotein or the E7 subunit of human papilloma virus) also elicited increased expression of $K^b$ on the dendritic cells (FIG. 10A). It is important to note, however, that unmodified hsp65 ("hsp65 only" in FIG. 10A, 10B) consistently failed to stimulate dendritic cell upregulation of $K^b$.

All of the fusion proteins as well as unmodified hsp65 were produced as recombinant proteins in *E. coli* and contained trace levels of endotoxin (lipopolysaccharide, LPS). An endotoxin standard by itself evoked a weak response at the highest concentration tested (5 EU/ml, FIG. 10B). Because of mol. wt. heterogeneity of LPS, conversion of endotoxin units into LPS weight and mole units is highly approximate. But, if one EU corresponds to about 5 ng LPS, and the "average" mol. wt. of LPS is taken to be approximately 10,000, LPS would appear to be somewhat more effective than hsp65 fusion proteins in activating dendritic cells. Nevertheless, the effects of the fusion proteins seemed clearly not to be due to endotoxin contaminants, because when hsp65-P1, hsp65, or Ma1-P1 were each added in amounts that resulted in addition of equivalent EU units to the dendritic cells, increased expression of $K^b$ was elicited only by hsp65-P1. Moreover, when the data from FIG. 10A were plotted against the EU concentrations attributable to the controls and fusion proteins, it was evident that each of the four hsp65 fusion protein preparations, but none of the controls, stimulated increased expression of MHC class I protein. Finally, all the hsp65 fusion proteins elicited increases in MHC class I expression on dendritic cells from C3H/HeJ mice, a strain known to be unresponsive to LPS (due to a mutation in the Toll4 receptor) (Poltorak, A., et al., *Science*, 282:2085-2088 (1998)). Taken together, the findings demonstrate that activation of the dendritic cells was due to the hsp65 fusion proteins, not to endotoxin contaminants. Besides stimulating the dendritic cells (bone marrow derived and maintained in culture with GM-CSF for 6 days) to express increased levels of MHC class I, the hsp fusion proteins stimulated increased expression of MHC class II and B7.2 (CD86) (the Table); the level of CD40 was, however, only marginally affected. Native hsp65 did not affect expression of MHC class II or B7.2, just as it failed to affect levels of MHC class I.

TABLE

Heat shock fusion proteins stimulate increased expression of MHC and costimulatory (B7.2) molecules on dendritic cells

|  | Nothing | unmodified hsp65 | P1 peptide | hsp65-NP | hsp65-P1 |
| --- | --- | --- | --- | --- | --- |
| MHC Class I | 100 | 105 | 96 | 257 | 151 |
| MHC Class II | 63 | 67 | 55 | 279 | 90 |
| B7.2 | 60 | 54 | 47 | 129 | 81 |
| CD40 | 45 | 45 | 47 | 76 | 51 |

Dendritic cells from bone marrow of C3H/HeJ mice were incubated for 18 hrs with $1.5 \times 10^{-6}$M of various heat shock proteins or the control P1 peptide prior to cell surface staining.

Activated Dendritic Cells in Vivo

Figure 9B:
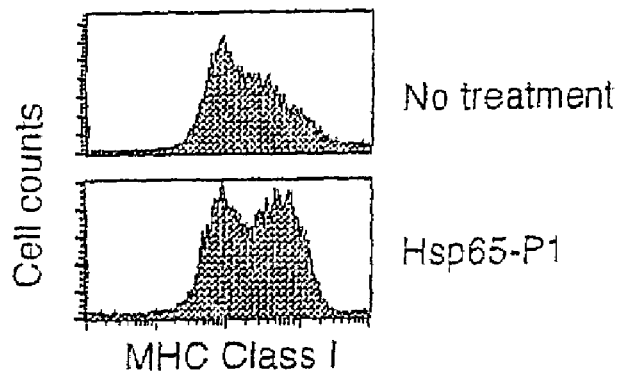
FIG. 9B is a pair of graphs illustrating the behavior of hsp65 fusion protein-activated dendritic cells in vivo. Myeloid dendritic cells from lymph nodes draining a subcutaneous site where hsp65-P1 was injected 24 hr previously show increased expression of MHC-1 ($K^b$) (lower panel) compared to myeloid dendritic cells from lymph nodes draining an uninjected site ("no treatment", upper panel).

That the dendritic cell changes could also be elicited in vivo was indicated by the finding that 24 hrs after injecting hsp65-P1 (in saline) subcutaneously into mice, myeloid dendritic cells (but not lymphoid dendritic cells) from lymph nodes draining the site of injection showed increased expression of $K^b$ (FIG. 9B).

Figure 9C:
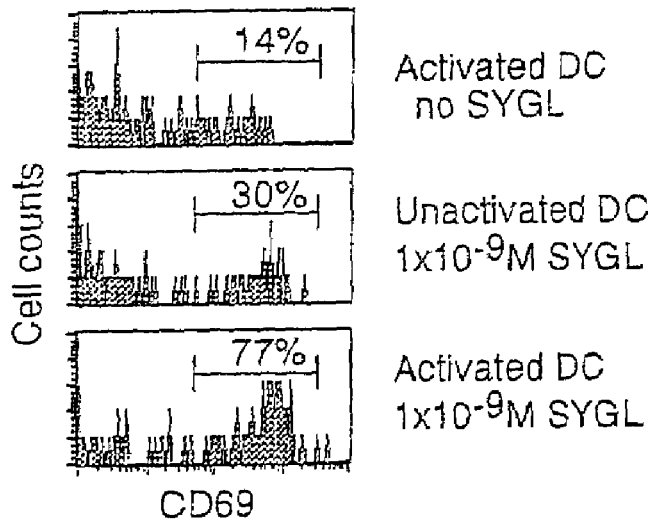
FIG. 9C is a trio of graphs illustrating the behavior of hsp65 fusion protein-activated dendritic cells in vivo. Dendritic cells activated with a noncognate hsp fusion protein (hsp65-NP) and pulsed with $10^{-9}$ M SYRGL peptide are more effective than nonactivated, similarly pulsed dendritic cells in stimulating naive T cells in vivo. $8\times10^5$ dendritic cells were injected into a hind footpad of normal B6 mice that had been injected (iv) with 2×10⁶ naive 2C TCR+ cells (from 2C TCR transgenic mice RAG-deficient mice). 24 hrs after the footpad injection, 2C CD8⁺ T cells in the draining popliteal lymph node were examined for CD69 expression. Frequency of CD69⁺ 2C CD8⁺ T cells in a lymph node draining the site where activated (control) dendritic cells (not pulsed with peptide) were injected (upper panel), or where SYRGL peptide-pulsed (1×10⁻⁹M) unactivated dendritic cells or activated dendritic cells were injected (middle panel and lower panel, respectively). Percentages of CD69⁺ 2C cells are shown. Geometric means fluorescence values for MHC-1 ($K^b$) on dendritic cells that had been incubated, prior to footpad injection, with or without hsp65-NP were 379 and 97, respectively.

To determine if activated DC were especially effective in vivo, normal B6 mice were adoptively transferred with $2 \times 10^6$ naive 2C cells (from 2C TCR transgenic mice, see Cho, B., et al., *Proc. Natl. Acad. Sci. USA*, 96:2976-2981 (1999)) and the next day the recipients were injected in a hind footpad with $8 \times 10^5$ dendritic cells. The dendritic cells had been incubated overnight with or without hsp65-NP (to generate activated or nonactivated dendritic cells, respectively), and then incubated for 2 hrs with SYRGL peptide at various concentrations (0, $10^{-6}$, $10^{-31.7}$, $10^{-8}$, $10^{-9}$M) and washed just before the cells were injected. 24 hrs later 2C CD8$^+$ T cells from the draining popliteal lymph nodes were examined for CD69 expression as evidence of having been antigenically stimulated. As shown in FIG. 9C, when the peptide concentration was $10^{-9}$M, the activated dendritic cells were considerably more effective than the nonactivated dendritic cells in stimulating the naive 2C T cells to express CD69. When pulsed with the peptide at 10-1000-times higher concentrations activated and nonactivated dendritic cells were about equally effective, stimulating CD69 responses of the 2C CD8$^+$ cells at about the level seen in FIG. 9C, bottom panel.

Stimulation of CD8 CTL Production in vivo by the hsp65-P1 Fusion Protein Does Not Require the Participation of CD4 T Cells The ability of the hsp fusion proteins to directly stimulate dendritic cells suggested that CD4 T cells might not be necessary for the CD8 T cell response elicited in vivo by the fusion proteins. To test this possibility, CD4 knockout mice (CD4$^{-/-}$) were immunized using the same regimen as before (FIG. 6A-6C) and their ability to produce SYRGL-specific CTL was assessed. As seen in a representative response in FIG. 10C, the CD4$^{-/-}$ mice produced CTL in response to hsp65-P1 but not in response to the control Ma1-P1. While the cytolytic activity elicited in the CD4$^{-/-}$ mice (n=6) was unambiguous, it appeared to be somewhat less than was generally elicited in normal C57BL/6 mice. In other experiments C57/BL6 mice that had been extensively depleted of CD4 cells by repeated injections or an anti-CD4 mAb (GK1.5) also responded to the standard immunization protocol with hsp65-P1 about as well as untreated normal mice (data not shown). All of these results show that in stimulating CD8 CTL production in mice hsp65-P1 does not require the participation of CD4 T cells.

Discussion

As shown herein, mycobacterial hsp65 fused to the P1 polypeptide activates dendritic cells and stimulates, in the absence of CD4$^+$ T cells, the production of CD8$^+$ CTL that recognize a short peptide derived from P1. The findings extend the number and diversity of hsp fusion proteins that can elicit CD8 T cell responses and suggest a potential mechanism by which the fusion proteins exert their effects in the absence of added adjuvants, a prominent feature of the in vivo responses to all hsp fusion proteins. Generally, where CD4 T cell help and adjuvants are required for CD8 T cell responses, it is likely that they function by activating dendritic cells (Bennett, S., et al., Eur. J. Immunol., Nature, 393:478-480 (1998); Ridge, J., et al., Nature, 393:474-478 (1998) and Schoenberger, S., et al., Nature, 393:480-483 (1998)). It is reasonable to expect that the capacity of heat shock fusion proteins to directly activate dendritic cells accounts for their ability to bypass the requirements for CD4 T cells and added adjuvants.

HSP Fusion Proteins Activate Dendritic Cells Directly

Using CTL to detect polypeptide processing by APC, previous studies pointed to macrophages, or equally to macrophage and dendritic cells, as being responsible for processing protein immunogens that elicit CD8 T cell responses (Kovacsovics-Bankowski, M., et al., Science, 267:243-245 (1995); Rock, K., Today, 17:131-137 (1996); Suto, R. and Srivastava, P. K., Science, 269:1585-1588 (1995)). As shown herein, when macrophages and dendritic cells were incubated with hsp65-P1 they become equally susceptible to lysis by peptide-specific CTL in a standard 4 hr cytolytic assays, indicating that both types of APC could generate small peptides from the hsp fusion protein and load them on the MHC class I molecules. However, when these cells were evaluated for their ability to stimulate naive CD8 T cells to proliferate and produce IL-2 and IFN-γ, the dendritic cells, but not the macrophages, proved to be effective. A step towards understanding this difference comes form the present finding that hsp65-P1, as well as each of the other hsp65 fusion proteins tested, is capable of directly stimulating dendritic cells to increase their surface expression of MHC class I and II and costimulatory (B7.2) molecules.

Dendritic cells infected with mycobacteria, including BCG, or streptococci, or Leishmania have been shown to upregulate MHC and costimulatory molecules B7.1 and B7.2 and, in addition, to secrete IL-12 (Demangel, C., et al., Eur. J. Immunol., 29:1972-1979 (1999); Henderson, R., et al., J. Immunol., 159:635-643 (1997); Konecny, P., et al., Eur. J. Immunol., 29:1803-1811 (1999); Rescigno, M., et al., Proc. Natl. Acad. Sci. USA, 95:5229-5234 (1998)). It may be that microbial cell hsp molecules are responsible for these effects. If so, the findings described herein (of a difference between hsp65 fusion proteins and unmodified hsp65) indicate that upregulation of these activation molecules are due to the hsp in a modified form, resembling perhaps the hsp65 fusion proteins studied here, rather than naive hsp molecules.

Dendritic cells infected with certain viruses, e.g., influenza virus (Ridge, J., et al., Nature, 393:474-478 (1998)), likewise become activated. However, the hsp fusion proteins appear, so far, to be the only soluble immunogenic proteins that directly activate dendritic cells, in vitro and in vivo, to upregulate expression of MHC and costimulatory molecules. The experimental system described herein is useful for investigating the pathways by which hsp fusion proteins are processed and presented by dendritic cells and the mechanisms by which MHC and costimulatory molecules are up-regulated.

Hsp Fusion Protein Stimulation of CD8 T Cell Production Does Not Depend Upon CD4 T Cells Prior to the present study one way to account for the ability of hsp fusion proteins to stimulate CD8 T cell production was to invoke a key role for CD4 T cells. Thus, a vigorous CD4 T cell response to peptides from the hsp moiety could activate dendritic cells and amplify an otherwise marginal CD8 T cell response to peptides from the fusion partner (Bennett, S., et al. Nature, 393:478-480 (1998); Ridge, J., et al., Nature, 393:474-478 (1998); Schoenberger, S., et al., Nature, 393:480-483 (1998)). This possibility is supported by older evidence that hsp65 can serve as an effective carrier molecule in the classic sense: i.e., when chemically coupled to nonimmunogenic hapten-like molecules (polysaccharides, a malarial peptide) the conjugates elicited IgG antibodies to the adducts in responses that were presumably T-cell dependent (Barrios, C., et al., Eur. J. Immunol., 22:1365-1372 (1992)). This mechanism is clearly not essential, because CD4$^{-/-}$ mice injected with hsp65-P1 produced cytolytic CD8 T cells to the fusion partner's peptide. Nevertheless, it is entirely possible that in normal animals the response may be enhanced by CD4 T cells specific for peptides derived from the hsp moiety.

Previous efforts to determine whether CD4 T cells are essential for CD8 T cell responses to various immunogens and immunization strategies have yielded diverse results. With some epitopes, e.g., minor histocompatibility antigens, CD8 T cell responses could not be elicited in CD4$^{-/-}$ mice (DiRosa, F. and Matzinger, P., *J. Exp. Med.*, 183:2153-2163 (1996)), but with more potent immunogens, (e.g., lymphocytic choriomeningitis virus or a murine herpes virus), or high doses of particulate antigens, CD8 CTL responses in CD4$^{-/-}$ mice were virtually the same as in normal mice (Rahemtulla, A., et al., *Nature*, 353:180-184 (1991); Rock, K. and Clark, K., *J. Immunol.*, 156:3721-3726 (1996); Stevenson, P., et al., *Proc. Natl. Acad. Sci. USA*, 95:15565-15570 (1998)). That CD4 T cells are not required for the CD8 T cell response to hsp65-P1 indicates that hsp fusion proteins are relatively potent immunogens for CD8 T cells.

The hsp Moiety in hsp Fusion Proteins

In the several hsp fusion proteins examined here the only common element is hsp65. The question arises as to how the hsp moiety can directly activate dendritic cells (and thereby elicit CD8 CTL production), regardless of wide variations in length and sequence of the fusion partners. It is particularly notable, in contrast, that unmodified ("native") hsp65 lacks this critical activity. It may be that in the fusion proteins the hsp moiety adopts a particular conformation or displays a linear sequence or peptide motif or pattern that is i) necessary for eliciting the dendritic cell response, ii) retained despite wide variations in the fusion partner sequences, and iii) absent or masked in unmodified ("native") hsp65.

The intensity of current interest in CD8 vaccines for HIV-1 and other persistent intracellular pathogens, as well as for cancer cells, is reflected in recent studies of diverse genetic vaccines and of several bacterial toxins fused to antigenic peptides or polypeptides as stimulators of CD8 CTL production. For example, nonapeptide sequences inserted into a truncated subunit of anthrax toxin or pertussis toxin, could elicit CD8 CTL in vivo (Ballard, J., et al., *Proc. Natl. Acad. Sci. USA*, 93:12531-12534 (1996) and render target cells susceptible to lysis by cognate CD8 CTL in vitro (Goletz, T., et al., *Proc. Natl. Acad. Sci. USA*, 94:12059-12064 (1997); Carbonetti, N., et al., *Infect. Immun.*, 67:602-607 (1999)). These and other bacterial toxins have evidently acquired through evolution the capacity to cross mammalian cell membranes and gain access to the cell cytosol, where they exert their lethal effects. While the judicious linkage of small peptides allows these toxin subunits to retain their ability to traverse membranes, the need to preserve this special property may limit the size and sequence diversity of the fusion elements that can be accommodated. For the hsp fusion proteins, in contrast, there appear so far to be no constraints to their effectiveness as CD8 immunogens by the length or sequence of the fusion partners. Because large fusion partners, e.g., the equivalent of a typical protein domain, are likely to encompass many potential epitopes for diverse MHC class I molecules, the hsp fusion proteins as a class are candidate vaccines for use with populations of MHC-disparate individuals.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inducing an immune response in an individual, the method comprising administering to the individual a portion of a heat shock protein (hsp) adenosinetriphosphate (ATP) binding domain consisting of about the C-terminal half of the ATP binding domain joined to a heterologous protein that contains at least one T-cell epitope, in a physiologically acceptable formulation and in an amount effective to elicit a $CD8^+$ cytotoxic T lymphocyte (CTL) response.

2. The method of claim 1, wherein the individual has a deficiency of $CD4^+$ T cells.

3. The method of claim 1, wherein the hsp is a bacterial, mycobacterial, fungal, parasitic, or mammalian hsp.

4. The method of claim 3, wherein the hsp is a mycobacterial hsp.

5. The method of claim 4, wherein the mycobacterial hsp is a *Mycobacterium bovis* (*M. bovis*), *Mycobacterium leprae* (*M. leprae*), or *Mycobacterium tuberculosis* (*M. tuberculosis*) hsp.

6. The method of claim 5, wherein the mycobacterial hsp is an *M. bovis* hsp.

7. The method of claim 6, wherein the *M. bovis* hsp is an *M. bovis* BCG hsp65.

8. The method of claim 1, wherein the hsp is an hsp65, hsp70, or hsp90.

9. The method of claim 8, wherein the hsp is an hsp65.

10. The method of claim 1, wherein the portion of the hsp ATP binding domain comprises amino acid residues 161-370 of *M. tuberculosis* hsp70.

11. The method of claim 1, wherein the portion of the hsp ATP binding domain comprises a portion of an hsp65 that is homologous to amino acid residues 161-370 of *M. tuberculosis* hsp70.

12. The method of claim 1, wherein the portion of the hsp ATP binding domain consists of amino acid residues 161-370 of *M. tuberculosis* hsp70.

13. The method of claim 1, wherein the portion of the hsp ATP binding domain consists of a portion of an hsp65 that is homologous to amino acid residues 161-370 of *M. tuberculosis* hsp70.

14. The method of claim 1, wherein the heterologous protein is a glycoprotein.

15. The method of claim 1, wherein the heterologous protein is a toxin, a bacterial antigen, a parasitic antigen, or a cancer cell-associated antigen.

16. The method of claim 1, wherein the heterologous protein is a viral antigen.

17. The method of claim 16, wherein the viral antigen is an antigen of an influenza virus, a human papilloma virus (HPV) or a herpes virus.

18. The method of claim 16, wherein the viral antigen is a human immunodeficiency virus (HIV) antigen.

19. The method of claim 16, wherein the viral antigen is HIV p24 or gp41, the influenza virus nucleoprotein, or HPV E7.

20. The method of claim 1, wherein the portion of the hsp ATP binding domain is joined to the heterologous protein by chemical conjugation.

21. The method of claim 1, wherein the portion of the hsp ATP binding domain is joined to the heterologous protein by a covalent bond.

22. The method of claim 21, wherein the covalent bond is a peptide bond.

23. The method of claim 1, wherein the composition further comprises a liposome.

24. The method of claim 1 wherein the $CD8^+$ cytotoxic T lymphocyte (CTL) response that is elicited is greater than the response elicited by administration of the heterologous protein alone.

* * * * *

UNITED STATES PATENT AND TRADEMARK OFFICE
CERTIFICATE OF CORRECTION

| | |
|---|---|
| PATENT NO. | : 7,501,125 B2 |
| APPLICATION NO. | : 10/885523 |
| DATED | : March 10, 2009 |
| INVENTOR(S) | : Huang et al. |

Page 1 of 1

It is certified that error appears in the above-identified patent and that said Letters Patent is hereby corrected as shown below:

On the title page
Field 54, Line 1, before "VIVO" insert the word --IN--.

In Column 1
Line 1, before "VIVO" insert the word --IN--.

In Column 50
Claim 19, Line 19, before "influenza" delete the word "the".

Signed and Sealed this

Second Day of June, 2009

JOHN DOLL
*Acting Director of the United States Patent and Trademark Office*